United States Patent
Liang et al.

(10) Patent No.: US 12,304,917 B1
(45) Date of Patent: May 20, 2025

(54) PLEUROMUTILIN DERIVATIVE CONTAINING A THIAZOLO[5,4-C]PYRIDINE SIDE CHAIN, AND A PREPARATION METHOD AND APPLICATION THEREOF

(71) Applicant: SHAANXI UNIVERSITY OF SCIENCE AND TECHNOLOGY, Shaanxi (CN)

(72) Inventors: Chengyuan Liang, Shaanxi (CN); Yanzi Wang, Shaanxi (CN); Bingxing Zhang, Shaanxi (CN); Wen Wang, Shaanxi (CN); Yunfei Zhang, Shaanxi (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 18/951,543

(22) Filed: Nov. 18, 2024

(30) Foreign Application Priority Data

May 15, 2024 (CN) .......... 202410603855.7

(51) Int. Cl.
C07D 513/04 (2006.01)
A61K 31/437 (2006.01)
A61P 31/04 (2006.01)
C07C 303/28 (2006.01)

(52) U.S. Cl.
CPC .......... *C07D 513/04* (2013.01); *A61K 31/437* (2013.01); *A61P 31/04* (2018.01); *C07C 303/28* (2013.01); C07C 2603/82 (2017.05)

(58) Field of Classification Search
CPC ..... A61K 31/437; A61P 31/04; C07C 303/28; C07C 2603/82; C07D 513/04
See application file for complete search history.

(56) References Cited

PUBLICATIONS

Shang et al., Efficient Antibacterial Agents: A Review of the Synthesis, Biological Evaluation and Mechanism of Pleuromutilin Derivatives, Current Topics in Medicinal Chemistry, 2013, 13, pp. 1-13 (Year: 2013).*

* cited by examiner

Primary Examiner — Savitha M Rao
Assistant Examiner — Andrew P Lee

(57) ABSTRACT

A compound of formula I, a pharmaceutically acceptable salt thereof, or a solvent compound, an enantiomer, a diastereomer or a tautomer of the compound or a pharmaceutically acceptable salt thereof is disclosed, wherein R is a phenyl substituted with an electron withdrawing group or a phenyl substituted with an electron donating group. The pleuromutilin derivative containing a thiazolo[5,4-C]pyridine side chain in the present invention exhibits good in vitro antibacterial activity and improves the problem of poor solubility of pleuromutilin derivatives.

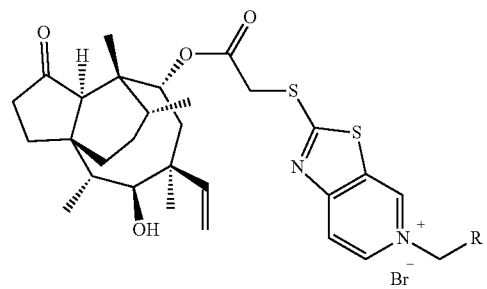

Formula I

11 Claims, 30 Drawing Sheets

PLEUROMUTILIN DERIVATIVE CONTAINING A THIAZOLO[5,4-C]PYRIDINE SIDE CHAIN, AND A PREPARATION METHOD AND APPLICATION THEREOF

This application claims priority to Chinese Patent Application No. 202410603855.7, filed on May 15, 2024, which is incorporated by reference for all purposes as if fully set forth herein.

TECHNICAL FIELD

The present invention belongs to the technical field of medicinal chemistry, and specifically relates to a class of pleuromutilin derivatives containing thiazolo[5,4-C]pyridine side chains, and a preparation method and application thereof.

BACKGROUND TECHNIQUE

In recent years, the overuse of antibiotics has led to the emergence of an increasing number of drug-resistant bacteria, making bacterial resistance an increasingly serious issue. A variety of drug-resistant "super bacteria" have begun to spread around the world, posing a great threat to human health. In response to the growing number, broader range, and higher degree of drug resistance, as well as the continuous emergence of multidrug-resistant bacteria, it is of great significance to explore drugs with novel antibacterial mechanisms, good bioavailability and low toxicity.

Pleuromutilin is a diterpenoid compound with a rigid 5-6-8 tricyclic carbon skeleton isolated from two natural basidiomycetes (Pleurotusmutilus and Pleurotuspasseckerianus). It exhibits strong antibacterial activity against Gram-positive bacteria and mycoplasmas. Pleuromutilin primarily exerts its antibacterial effect by interacting with the peptidyl transferase center (PTC) of bacterial ribosomes to interfere with the binding of tRNA to the P site and the A site, thereby inhibiting protein synthesis. Due to the high conservatism of PTC, pleuromutilin exhibits a relatively low rate of drug resistance. Pleuromutilin has a different antibacterial mechanism from existing antibiotics on the market. It provides a new idea for finding safe and effective drugs and has become one of the hot spots in antibiotic research. However, the existing pleuromutilin drugs have poor water solubility, resulting in low drug utilization.

SUMMARY OF THE INVENTION

In one embodiment, the present application discloses compound of formula I, a pharmaceutically acceptable salt, a diastereomer, or a tautomer thereof:

Formula I

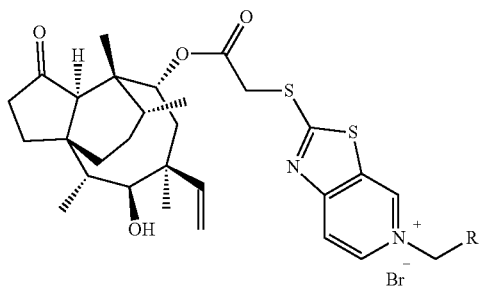

R is a phenyl group substituted with an electron withdrawing group or a phenyl group substituted with an electron donating group.

In another embodiment, the compound is selected from the group consisting of:

I-1

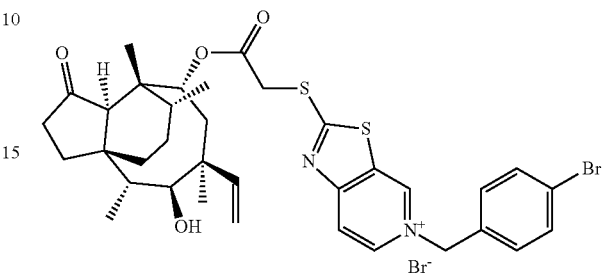

I-2

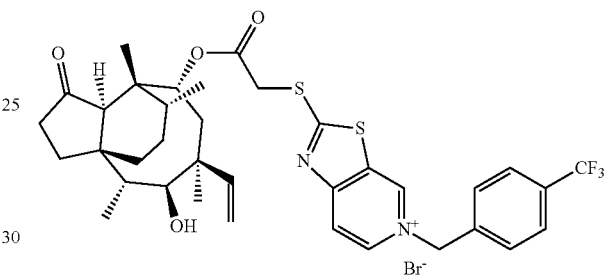

I-3

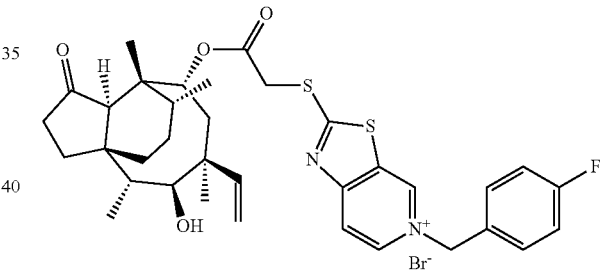

I-4

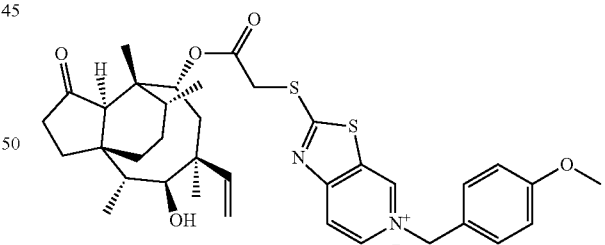

I-5

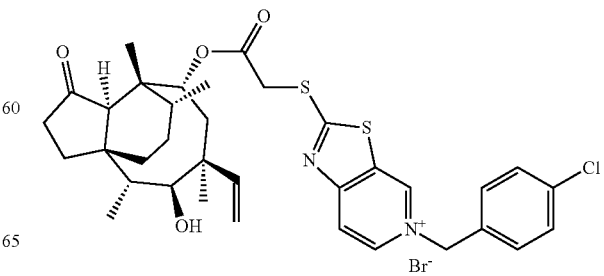

I-6
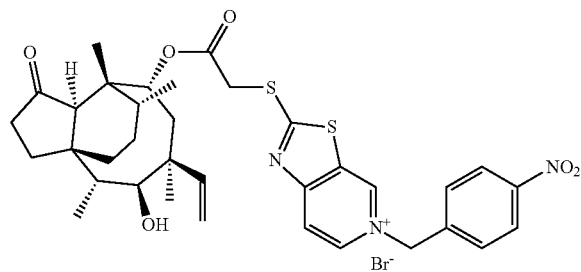

I-7
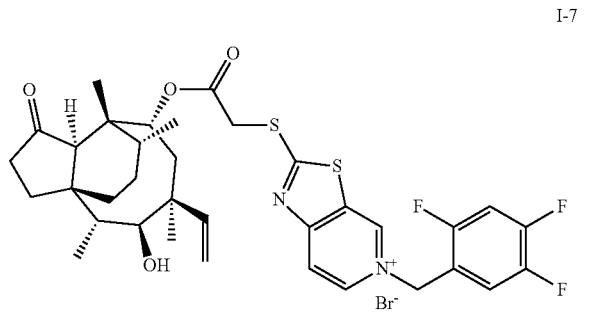

I-8
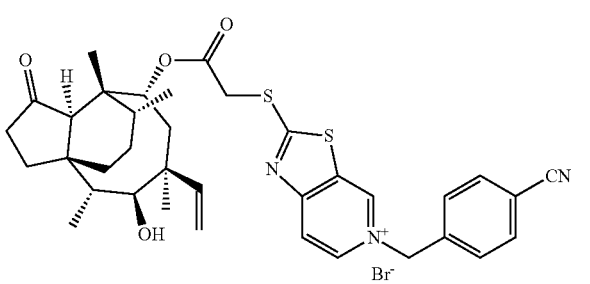

I-9
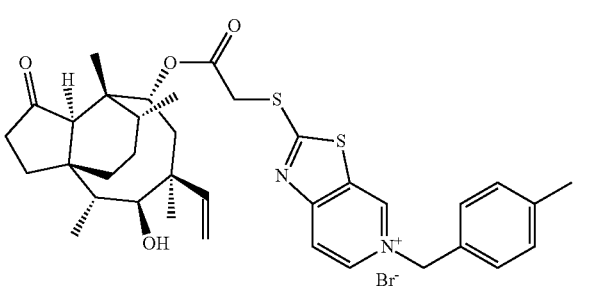

I-10
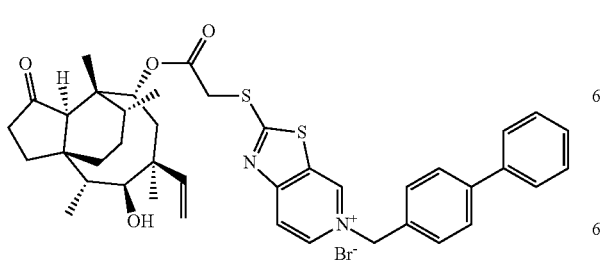

I-11
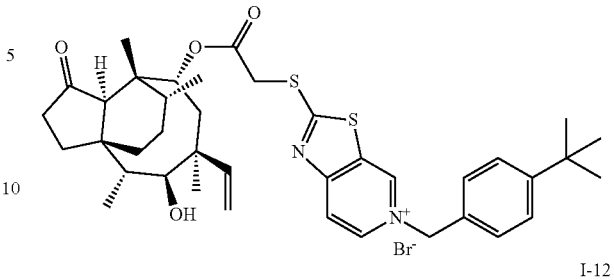

I-12
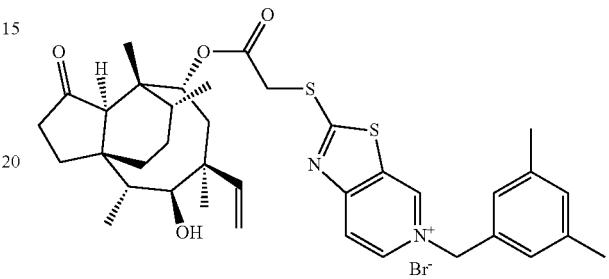

I-13
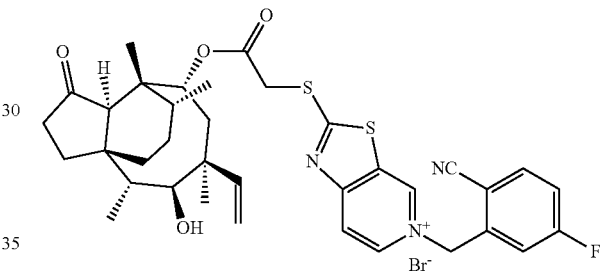

I-14
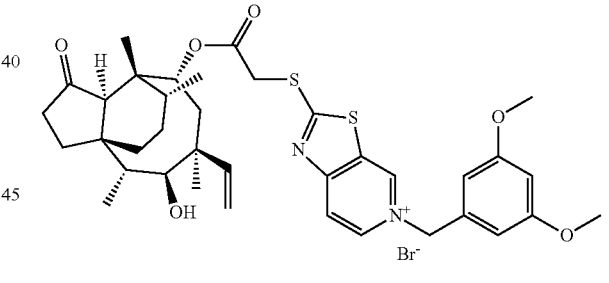

In another embodiment, the pharmaceutically acceptable salts include one selected from the group consisting of hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid or aspartic acid.

In another embodiment, the present application discloses the use of the compound in the preparation of a drug for treating infectious diseases caused by pathogenic microorganisms, wherein the pathogenic microorganisms are Gram-positive bacteria, Gram-negative bacteria, drug-resistant bacteria or *mycoplasma*.

Compared with the prior art, the present invention has the following beneficial effects:

The present invention structurally transforms pleuromutilin by using a quaternary ammonium salt compound to modify it, thereby obtaining a pleuromutilin onium salt derivative containing a thiazolo[5,4-C]pyridine side chain. Quaternary ammonium salts are compounds formed by replacing all four hydrogen atoms in ammonium ions with hydrocarbon groups, which dissociate in water to form quaternary ammonium cations. Quaternary ammonium salt drugs contact the bacterial surface through electrostatic interaction and then pass through the cell wall. The nonpolar tail of the quaternary ammonium salt drug will insert into the bacterial cell membrane, promote pore formation, lead to loss of cell integrity, thereby destroying the cell membrane, and ultimately leading to bacterial death. In vitro antibacterial activity assays demonstrate that the compounds of the present invention can inhibit different bacterial strains, and most of the compounds have stronger inhibitory effects on drug-resistant bacteria than marketed drugs valnemulin and retapamulin. Water solubility statistics show that the water solubility of most target compounds has been significantly improved, and is better than tiamulin and valnemulin. The quaternization modification strategy has a positive effect on improving the water solubility of pleuromutilin onium salt derivatives. The safety evaluation experiments further revealed that the compounds of the present invention showed lower toxicity to the test cells compared with the positive control drugs retapamulin and valnemulin. In summary, the pleuromutilin derivatives containing thiazolo[5,4-C]pyridine side chains of the present invention exhibit strong in vitro antibacterial activity and improve the problem of poor solubility of pleuromutilin derivatives.

The method for preparing the pleuromutilin derivatives containing thiazolo[5,4-C]pyridine side chains of the present invention utilizes readily available raw materials, ensures high operation safety, involves mild reaction conditions and offers low production costs, and achieves a high yield ranging from 72% and 92%. This method is suitable for industrial production.

The pleuromutilin derivatives containing thiazolo[5,4-C] pyridine side chains of the present invention can be used to prevent and treat infectious diseases caused by Gram-positive bacteria, Gram-negative bacteria, drug-resistant bacteria or *mycoplasma*, and possess significant potential for medical development.

DETAILED DESCRIPTION OF EMBODIMENTS

Figure 1:
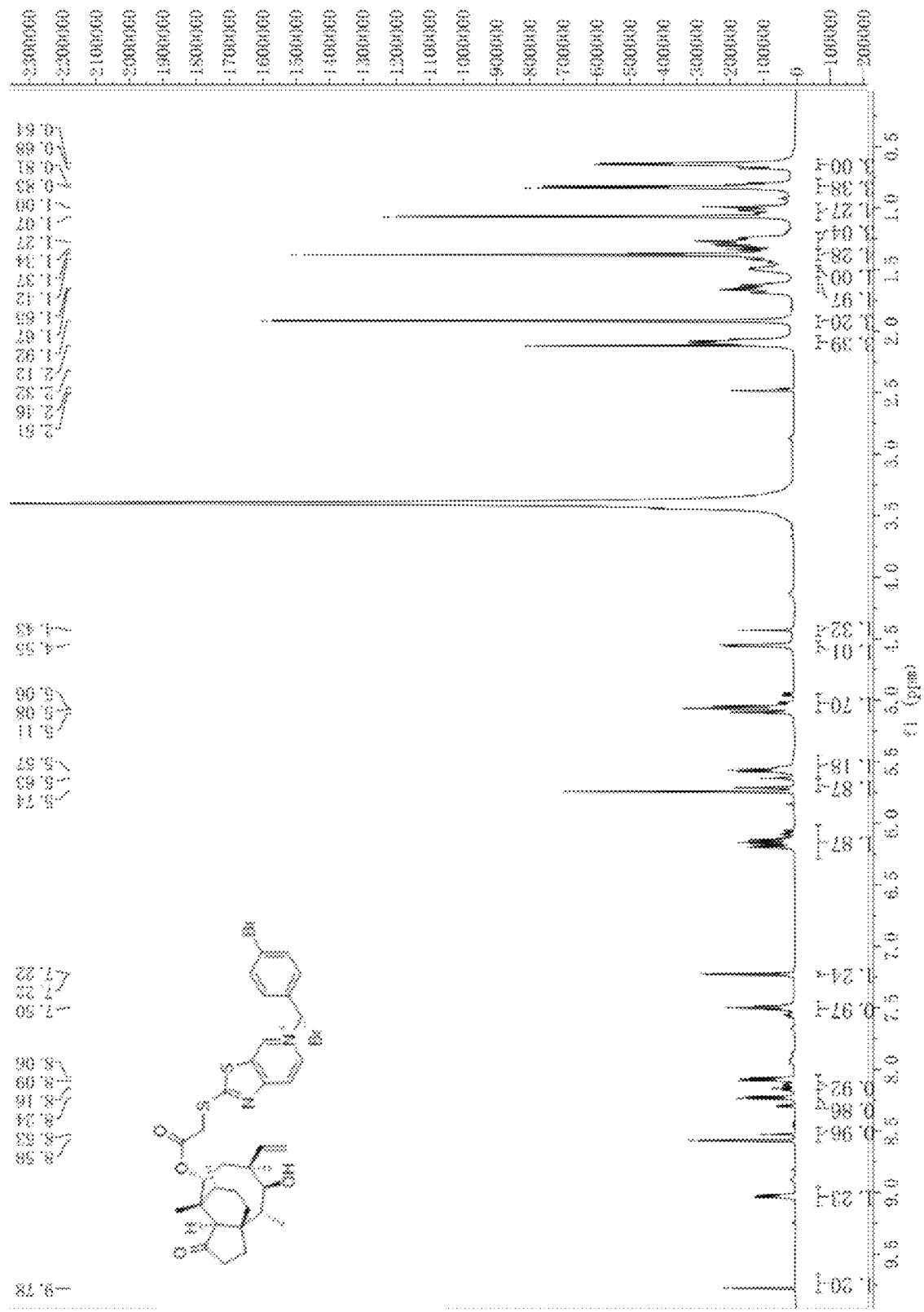
FIG. 1 is a $^1$H NMR spectrum of Compound I-1 of the present invention in deuterated DMSO.

The following specific examples illustrate the embodiments of the present invention, and those skilled in the art can easily understand other advantages and effects of the present invention from the contents disclosed in this specification. The present invention can also be implemented or applied through other different specific embodiments, and the details in this specification can also be modified or changed in various ways based on different viewpoints and applications without departing from the spirit of the present invention.

The pleuromutilin derivatives containing thiazolo[5,4-C] pyridine side chains of the present invention are compounds having a structural formula as shown in Formula I, or pharmaceutically acceptable salts thereof, or solvent compounds, enantiomers, diastereomers, tautomers or mixtures thereof in any proportion, including racemic mixtures, of the compounds shown in Formula I or pharmaceutically acceptable salts thereof.

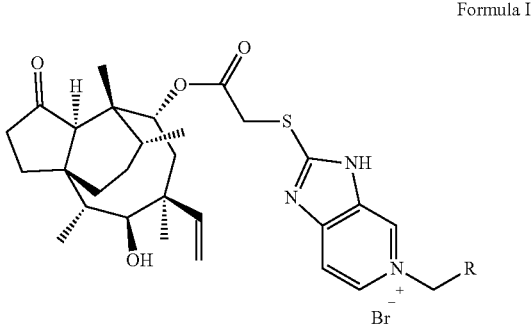

Formula I

Wherein, R is a phenyl group substituted with an electron-withdrawing group or a phenyl group substituted with an electron-donating group.

The pharmaceutically acceptable salts include a salt selected from the group consisting of hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid, or aspartic acid.

The compounds of the present application can be synthesized by a method that includes the following operation steps:

(1) Pleuromutilin is reacted with tosyl chloride to obtain intermediate I, wherein, intermediate I is

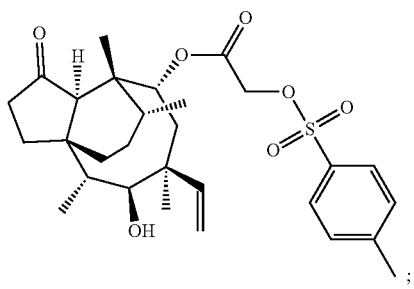 [SMILES: C=C[C@]1(C)C[C@@H](OC(=O)COS(=O)(=O)c2ccc(C)cc2)[C@]2(C)[C@H](C)CC[C@]3(CCC(=O)[C@H]32)[C@@H](C)[C@@H]1O]

(2) 4-amino-3-fluoropyridine is reacted with potassium ethyl xanthate to obtain intermediate II; wherein, Intermediate II is

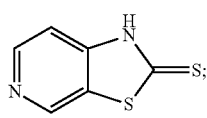

(3) Intermediate I is reacted with intermediate II under alkaline conditions to obtain intermediate III; wherein, basic catalysts are potassium carbonate and potassium iodide, and intermediate III is

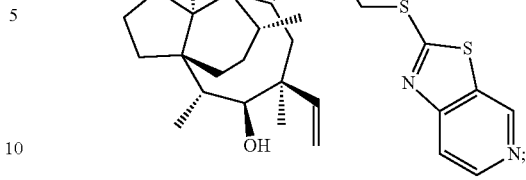

(4) Intermediate III is reacted with a benzene ring compound containing a substituent to obtain a pleuromutilin derivative shown in general formula I.

In a specific embodiment of the present invention, in step (1), the molar ratio of pleuromutilin to tosyl chloride is 1:1.2; in step (2), the molar ratio of 4-amino-3-fluoropyridine to potassium ethyl xanthate is 1:1.2; in step (3), the molar ratio of intermediate I to intermediate II is 1:1.2; in step (4), the molar ratio of intermediate III to the substituted benzene ring compound is 1:3.

In a specific embodiment of the present invention, the reaction described in step (1) uses dichloromethane as a solvent, with triethylamine and 4-dimethylaminopyridine as catalysts, and the reaction temperature is room temperature; the reaction described in step (2) uses N,N-dimethylformamide as a solvent; the reaction described in step (3) uses N,N-dimethylformamide as a solvent, and the reaction conditions are under alkaline catalyst conditions, and the alkaline catalyst is potassium carbonate or potassium iodide; the reaction described in step (4) uses acetonitrile, acetone or toluene as a solvent, the reaction temperature is room temperature, and the reaction time is 8 to 12 hours.

The pleuromutilin derivatives containing thiazolo[5,4-C] pyridine side chains of the present invention have antimicrobial activity and can be used for the preparation of drugs for treating infectious diseases caused by pathogenic microorganisms.

Wherein, the pathogenic microorganism are Gram-positive bacteria, Gram-negative bacteria, drug-resistant bacteria or *mycoplasma*.

Wherein, the Gram-positive bacteria are: Methicillin-resistant *S. aureus* ATCC 33591, Methicillin-resistant *S. aureus* ATCC 43300, *S. aureus* ATCC 29213 or Methicillin-resistant *S. epidermidis* ATCC 51625; the Gram-negative bacteria are *A. baumannii* ATCC 19606, *S. enterica* ATCC14028, *E. coli* ATCC 25922 or *E. coli* CMCC 44103.

Wherein, the drug-resistant bacteria are MRSA-171, MRSA-575, MRSA-206, MRSA-222, MRSA-596, VRE-80, MDR-PA-126, MDR-KP-893 or CR-AB-882.

Wherein, the mycoplasmas are *M. hyopneumoniae* J (NCTC10110), *M. hyopneumoniae* LH (clinical isolate), *M. hyorhinis* BTS-7 (NCTC10130), *M. gallisepticum* (NCTC10115), *M. synoviae* WVU1853 (NCTC10124), *M. pneumoniae* M129 (ATCC29342), *C. pneumoniae* AR39 (ATCC53592), *C. pneumoniae* CWL-029 (VR-1310), *C. pneumoniae* TW183 (VR-2282), *M. hominis* PG-21 (ATCC23114), *M. genitalium* G37 (ATCC33530).

The present invention also provides an antibiotic drug, which contains an effective amount of the aforementioned pleuromutilin derivative of the thiazolo[5,4-C]pyridine side chain, and the remainder is a pharmaceutical excipient or other compatible drugs, wherein, the pharmaceutical excipient is a pharmaceutically acceptable carrier, excipient or diluent.

Synthesis examples of the compounds are given below.

Example 1

Preparation of Compound I-1:5-(4-bromobenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8] cyclo-5-yl)oxy)-2-oxoethyl)thio)thiazolo[5,4-c]pyridin-5-ium (1) Preparation of Compound Intermediate I

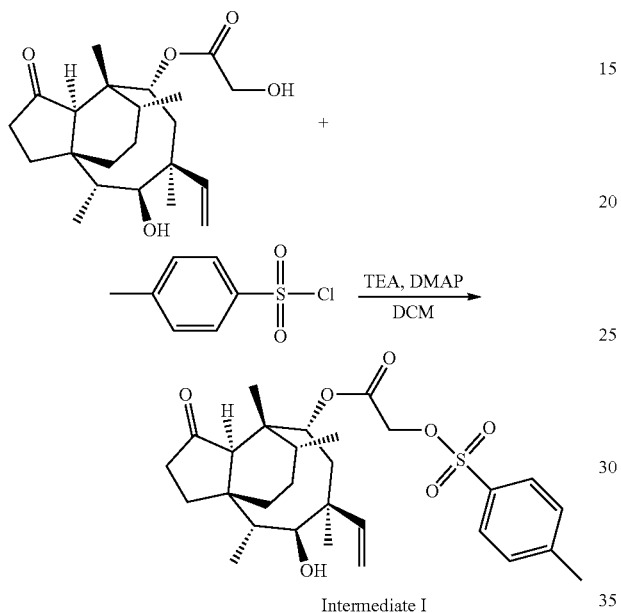

Intermediate I

Pleuromutilin (7.57 g, 20 mmol), tosyl chloride (4.58 g, 24 mmol) and 4-dimethylaminopyridine (0.25 g, 2 mmol) were added to dichloromethane (100 mL) as the solvent and stirred to dissolve. Triethylamine (8.35 mL, 60 mmol) was then added, and the reaction was stirred at room temperature for 8 hours. After the reaction was completed, the reaction solution was concentrated, then washed with a saturated $NaHCO_3$ aqueous solution, and finally vacuum dried to obtain intermediate I with a yield of 96%.

(2) Preparation of Compound Intermediate II

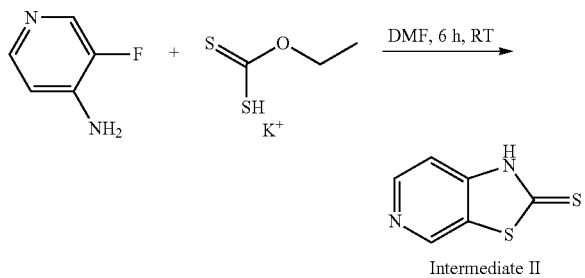

Intermediate II

4-Amino-3-fluoropyridine (401 mg, 10 mmol) and potassium ethyl xanthate (1.3 g, 12 mmol) were added to the solvent N,N dimethylformamide (2.3 mL). After the reaction was completed, the mixture was cooled to room temperature. $H_2O$ (10 mL) and 1M HCl aqueous solution (20 mL) were added to the reaction mixture to form a precipitated solid. The mixture was stirred 30 minutes, then filtered, and the solid was washed with water. The obtained filter cake was dissolved in ethyl acetate to adjust the pH to 4.0. The solution was dried with $MgSO_4$ and concentrate under reduced pressure to obtain a solid, which is Intermediate II, with a yield of 90%.

(3) Preparation of Compound Intermediate III

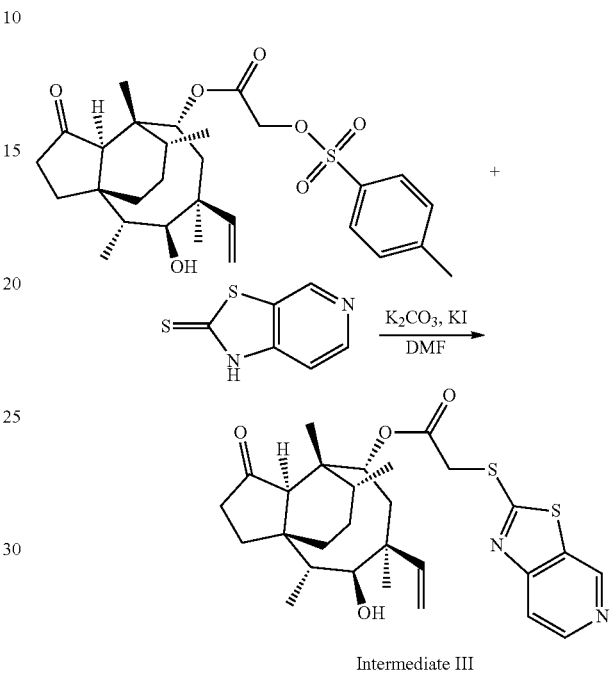

Intermediate III

Intermediate I (5.33 g, 10 mmol), intermediate II (2.02 g, 12 mmol), potassium carbonate (2.77 g, 20 mmol) and potassium iodide (0.16 g, 1 mmol) were added to 50 mL of N,N-dimethylformamide as the solvent and dissolved. The mixture was heated to 60° C. and reacted for 6 hours. After the reaction was completed, 200 mL of saturated ammonium chloride aqueous solution was added to the reaction solution, followed by extraction with ethyl acetate. The ethyl acetate phase was then concentrated and separated by column chromatography to obtain intermediate III. The eluent used for column chromatography was a dichloromethane-methanol mixture with a volume ratio of 18:1, and the yield was 85%.

(4) Preparation of Compound I-1

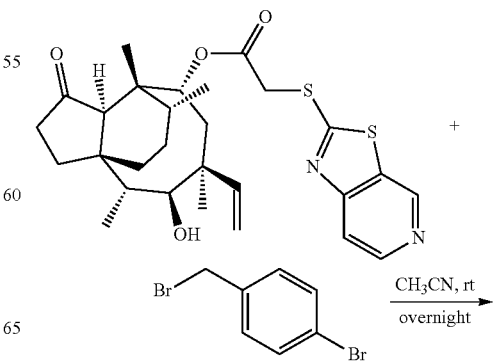

11

-continued

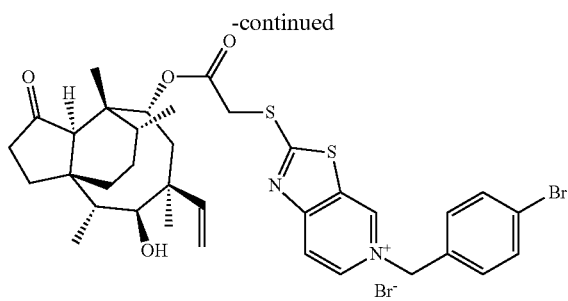

12

-continued

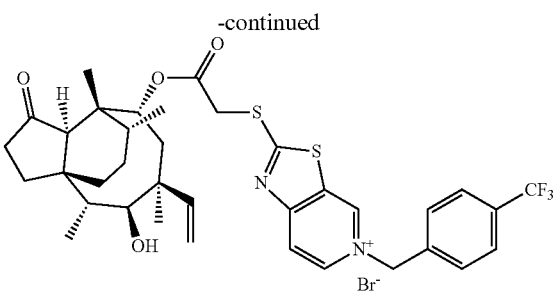

Figure 2:
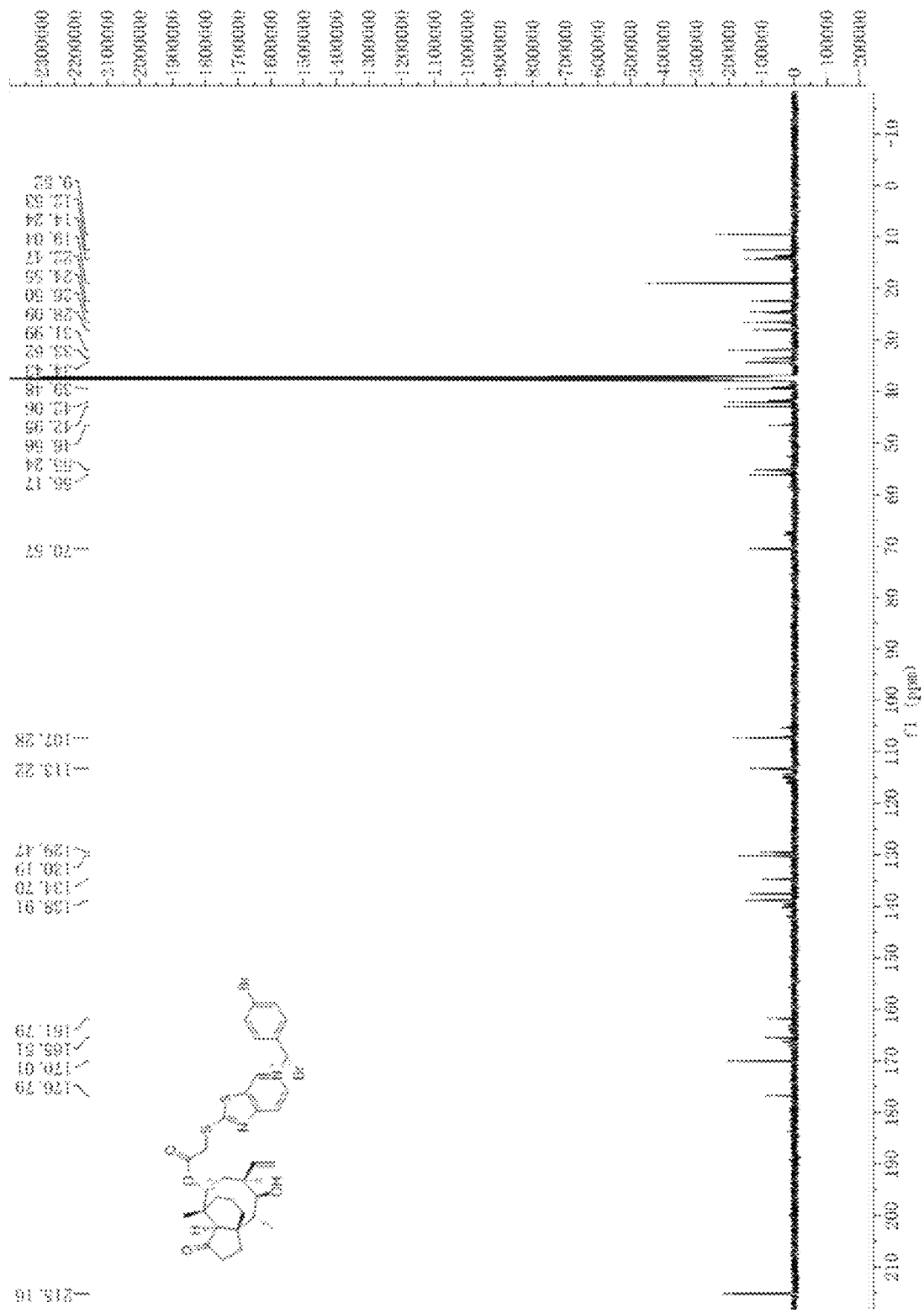
FIG. 2 is a $^{13}$C NMR spectrum of Compound I-1 of the present invention in deuterated DMSO.

Intermediate III (0.264 g, 0.5 mmol) and 4-bromobenzyl bromide (0.375 g, 1.5 mmol) were dissolved in acetonitrile (5 mL), and reacted at room temperature for 12 hours. The solvent was removed by concentration under reduced pressure, and the resulting mixture was purified by column chromatography to obtain compound I-1. The eluent for column chromatography was a mixture of dichloromethane and methanol (12~8:1 by volume), with a yield of 72%. The $^1$H NMR spectrum of compound I-1 in deuterated DMSO is shown in FIG. 1, and the $^{13}$C NMR spectrum in deuterated DMSO is shown in FIG. 2.

$^1$H NMR (600 MHZ, DMSO-d6) δ 9.78 (d, J=1.5 Hz, 1H), 9.03 (d, J=1.6 Hz, 1H), 8.58 (d, J=6.4 Hz, 1H), 8.24-8.16 (s, 1H), 8.09-8.06 (d, J=1.2 Hz, 1H), 7.50 (s, 1H), 7.22 (d, J=1.5 Hz, 1H), 5.74 (d, J=1.6 Hz, 1H), 5.63 (d, J=1.8 Hz, 2H), 5.57 (s, 1H), 5.11-5.06 (d, J=1.2 Hz, 2H)), 4.55 (d, J=6.0 Hz, 1H), 4.43 (s, 1H), 2.11-2.06 (d, J=4.7 Hz, 3H), 2.02-1.92 (d, J=2.4 Hz, 3H), 1.67-1.65 (m, 2H), 1.42 (d, J=1.6 Hz, 1H), 1.37-1.34 (d, J=2.8 Hz, 4H), 1.27-1.07 (d, J=2.8 Hz, 3H), 0.83 (dd, J=1.6 Hz, 4H), 0.81-0.68 (dd, J=1.2 Hz, 3H), 0.64 (d, J=7.3 Hz, 3H).

$^{13}$C NMR (151 MHZ, DMSO-d6) δ 215.16, 176.79, 170.01, 165.51, 161.79, 138.91, 134.70, 130.19, 129.47, 113.22, 107.28, 70.57, 56.17, 55.24, 46.56, 42.95, 42.06, 39.48, 34.43, 33.62, 31.99, 28.09, 26.50, 24.55, 22.47, 19.04, 14.24, 12.53, 9.52.

Example 2

Preparation of Compound I-2:5-(4-trifluoromethyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8] cyclo-5-yl)oxy)-2-oxoethyl)thio)thiazolo[5,4-c]pyridin-5-ium

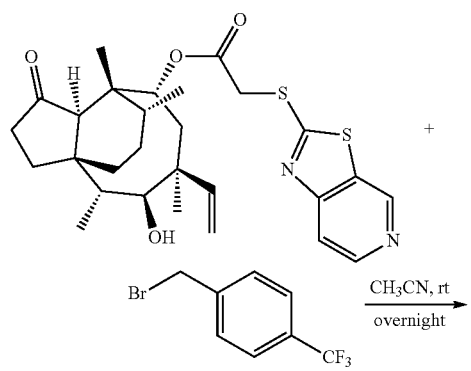

Figure 3:
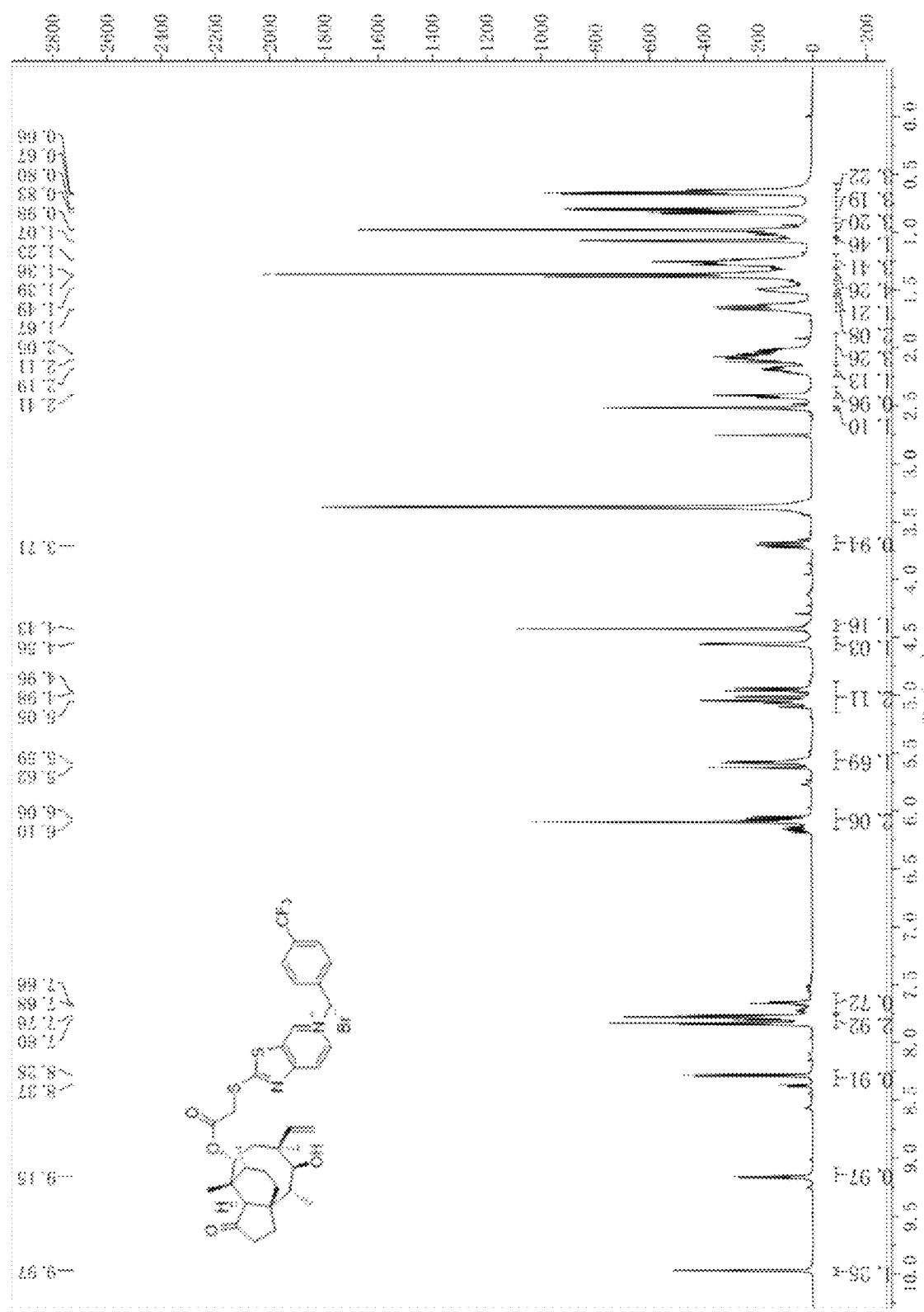
FIG. 3 is a $^1$H NMR spectrum of Compound I-2 of the present invention in deuterated DMSO.
Figure 4:
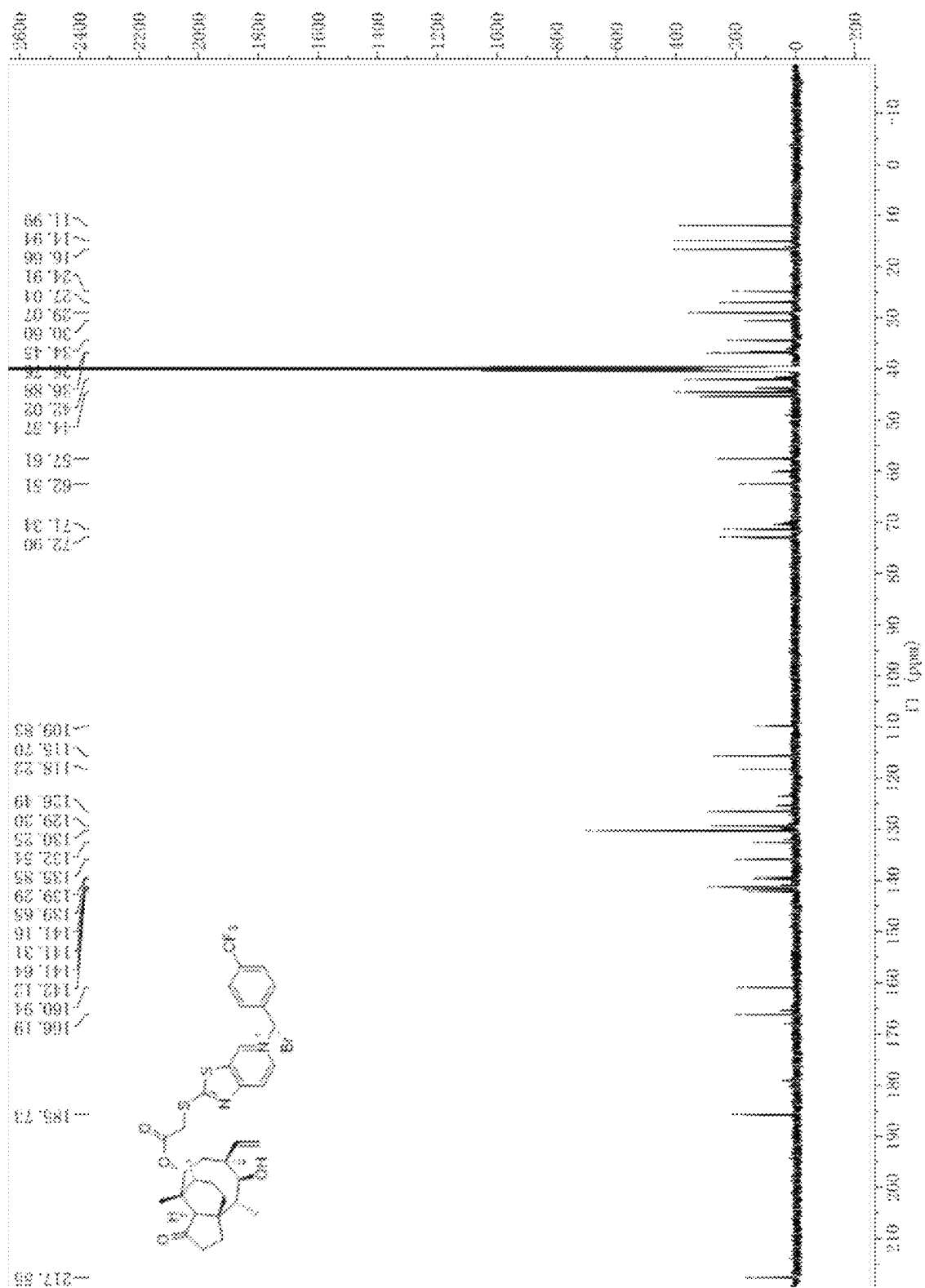
FIG. 4 is a $^{13}$C NMR spectrum of Compound I-2 of the present invention in deuterated DMSO.

The preparation method was as described in Example 1, except that the corresponding raw materials were replaced. Yield of Compound I-2 obtained: 83%. The $^1$H NMR spectrum of compound I-2 in deuterated DMSO is shown in FIG. 3, and the $^{13}$C NMR spectrum in deuterated DMSO is shown in FIG. 4.

$^1$H NMR (600 MHZ, DMSO-d6) δ 9.97 (d, J=1.6 Hz, 1H), 9.16 (dd, J=7.0, 1.6 Hz, 1H), 8.37-8.24 (m, 1H), 7.94-7.69 (m, 3H), 7.56-7.49 (m, 1H), 6.16-5.98 (m, 2H), 5.64-5.48 (m, 2H), 5.15-4.88 (m, 2H), 4.56 (dd, J=6.1, 2.5 Hz, 1H), 4.43 (s, 1H), 3.74-3.62 (m, 1H), 2.54-2.49 (m, 1H), 2.44-2.32 (m, 1H), 2.24-2.19 (m, 1H), 2.11-1.82 (dt, J=18.7, 8.7 Hz, 3H), 1.67-1.62 (m, 2H), 1.60-1.52 (m, 1H), 1.46-1.31 (m, 4H), 1.23-0.95 (m, 3H), 1.22-1.16 (m, 1H), 1.09-0.86 (m, 3H), 0.82 (dd, J=18.0, 6.9 Hz, 3H), 0.65 (dd, J=12.2, 7.2 Hz, 3H).

$^{13}$C NMR (151 MHZ, DMSO-d6) δ 217.55, 185.73, 166.19, 160.94, 142.12, 141.64, 141.31, 141.16, 139.65, 139.29, 135.85, 132.54, 130.25, 129.30, 126.49, 118.22, 115.70, 109.83, 72.90, 71.34, 62.51, 57.61, 44.57, 42.02, 36.88, 36.76, 34.45, 30.60, 29.07, 27.04, 24.91, 16.66, 14.94, 11.99.

Example 3

Preparation of Compound I-3:5-(4-fluorobenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8] cyclo-5-yl)oxy)-2-oxoethyl)thio)thiazolo[5,4-c]pyridin-5-ium

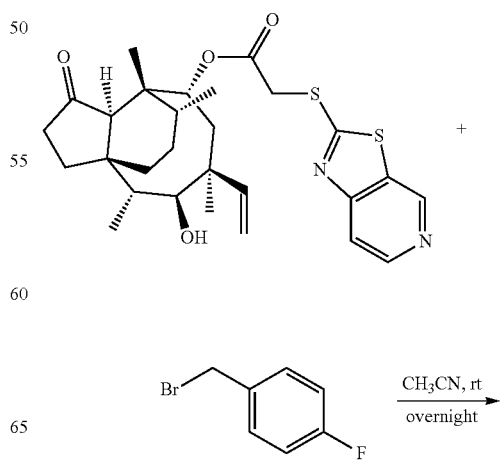

-continued

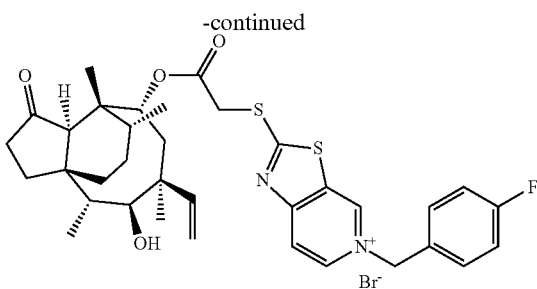

Figure 5:
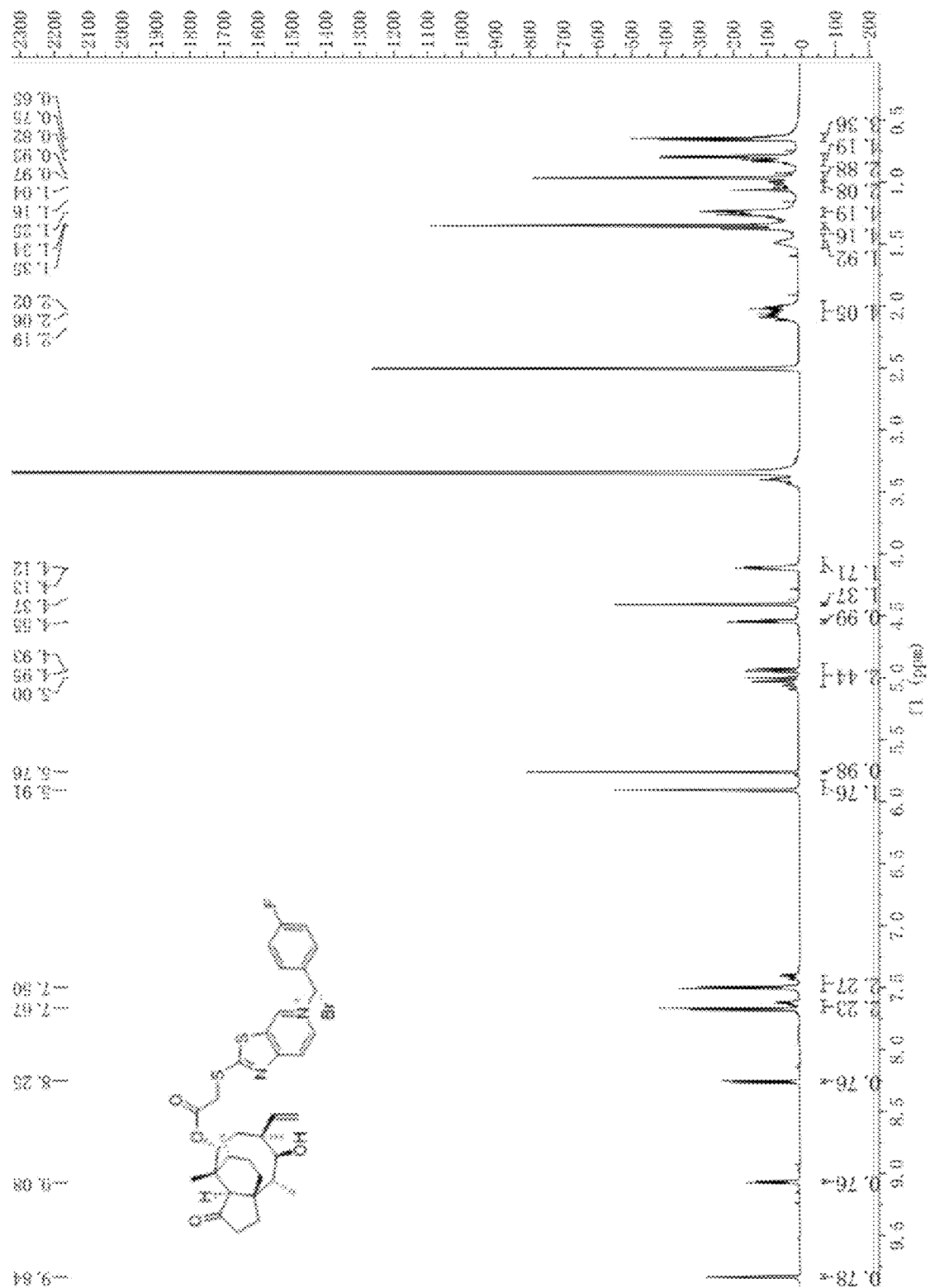
FIG. 5 is a $^1$H NMR spectrum of Compound I-3 of the present invention in deuterated DMSO.
Figure 6:
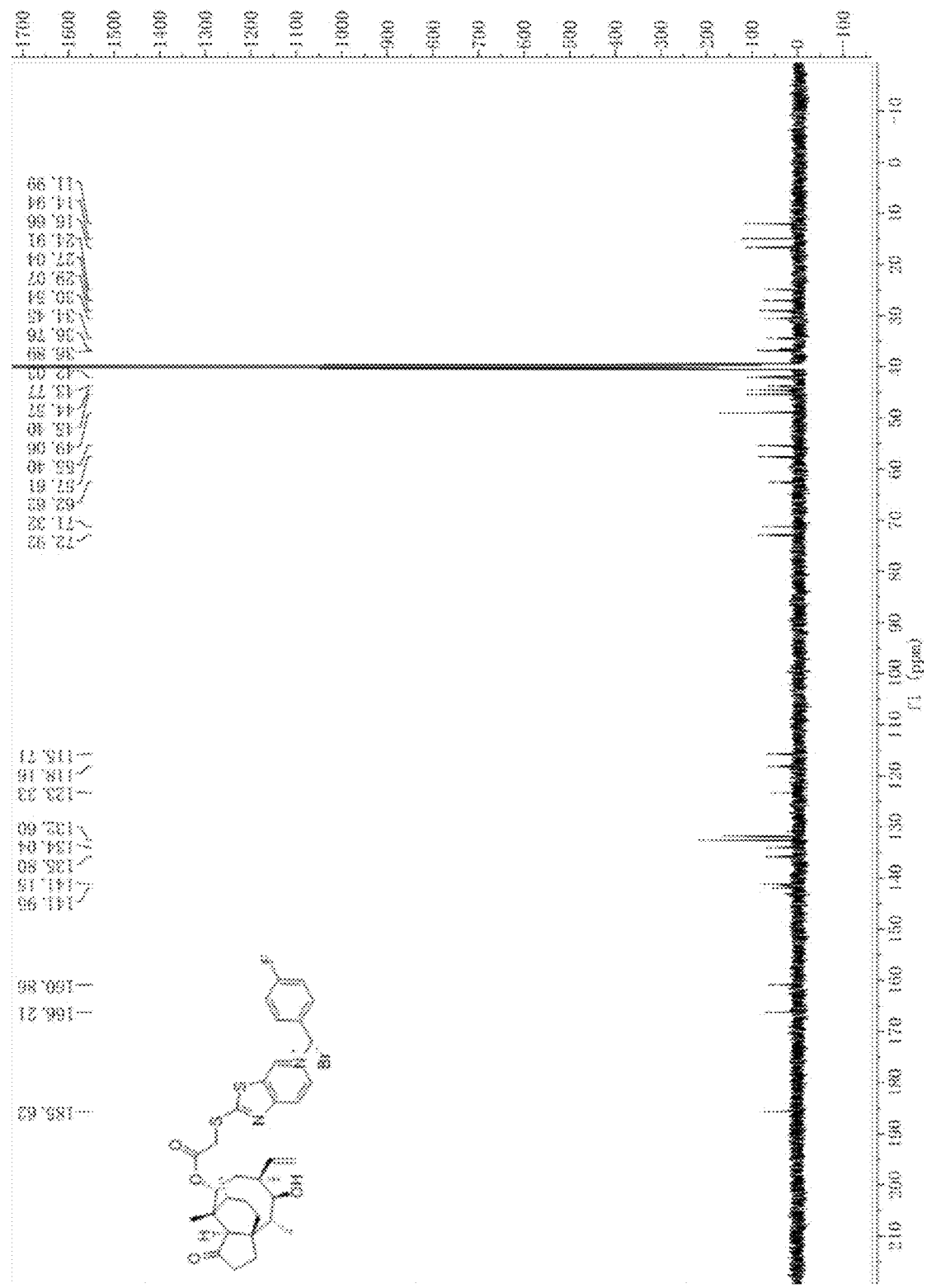
FIG. 6 is a $^{13}$C NMR spectrum of Compound I-3 of the present invention in deuterated DMSO.

The preparation method was as described in Example 1, except that the corresponding raw materials were replaced. Yield of Compound I-3 obtained: 81%. The ¹H NMR spectrum of compound I-3 in deuterated DMSO is shown in FIG. 5, and the ¹³C NMR spectrum in deuterated DMSO is shown in FIG. 6.

¹H NMR (600 MHZ, DMSO-d6) δ 9.84 (d, J=1.5 Hz, 1H), 9.08 (dd, J=6.8, 1.6 Hz, 1H), 8.25 (d, J=6.9 Hz, 1H), 7.69-7.66 (m, 2H), 7.52-7.48 (m, 2H), 5.91 (s, 2H), 5.76 (s, 1H), 5.00-4.92 (d, J=6.8 Hz, 2H), 4.55 (d, J=6.0 Hz, 1H), 4.41 (s, 1H), 4.11 (q, J=5.3 Hz, 2H), 2.19-2.02 (d, J=4.2 Hz, 4H), 1.57-1.41 (d, J=4.7 Hz, 2H), 1.37-1.31 (d, J=4.7 Hz, 4H), 1.25 (d, J=15.9 Hz, 4H), 1.18-1.12 (m, 2H), 0.97 (s, 3H), 0.81 (dd, J=18.2, 6.9 Hz, 4H), 0.65 (d, J=7.3 Hz, 3H).

¹³C NMR (151 MHZ, DMSO-d6) δ 185.62, 166.21, 160.86, 141.95, 141.15, 135.80, 134.04, 132.60, 123.33, 118.16, 115.71, 72.92, 71.32, 62.62, 57.61, 55.40, 49.06, 45.40, 44.57, 43.77, 42.03, 36.89, 36.76, 34.45, 30.54, 29.07, 27.04, 24.91, 16.66, 14.94, 11.99.

Example 4

Preparation of Compound I-4:5-(4-methoxybenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8] cyclo-5-yl)oxy)-2-oxoethyl)thio)thiazolo[5,4-c]pyridin-5-ium

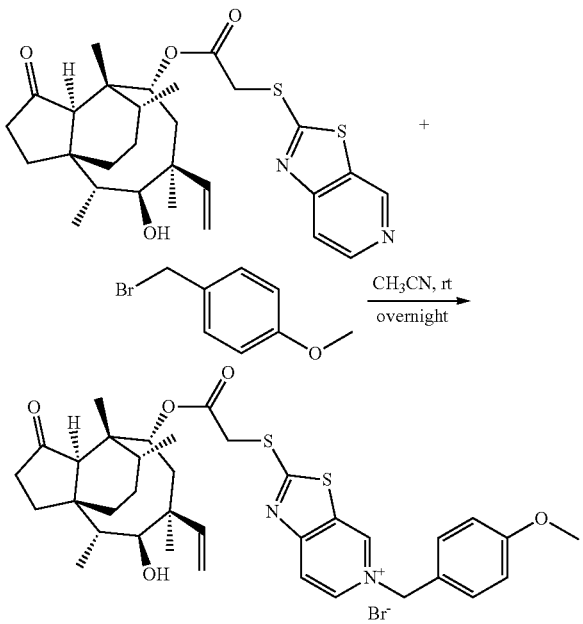

Figure 7:
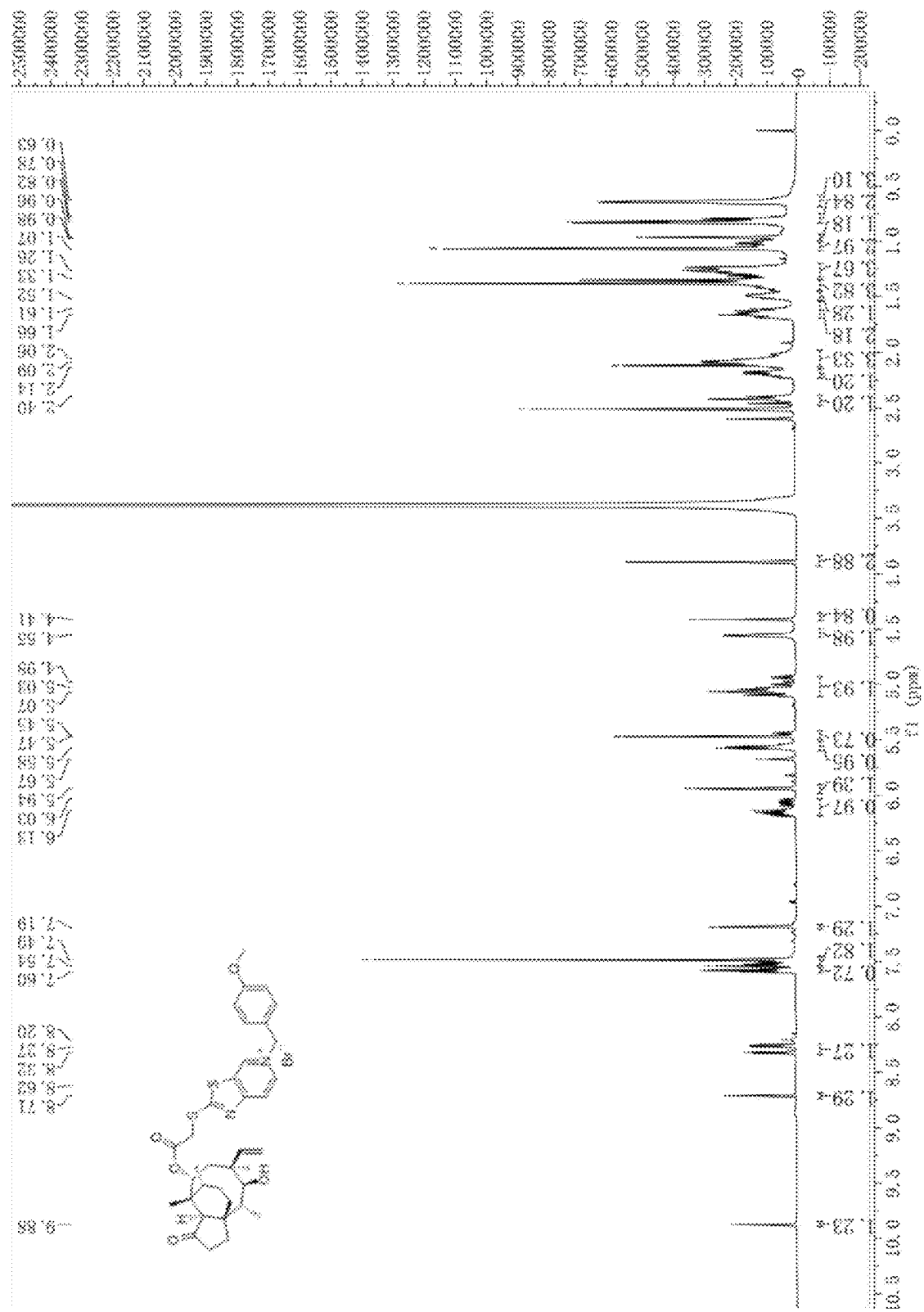
FIG. 7 is a $^1$H NMR spectrum of Compound I-4 of the present invention in deuterated DMSO.
Figure 8:
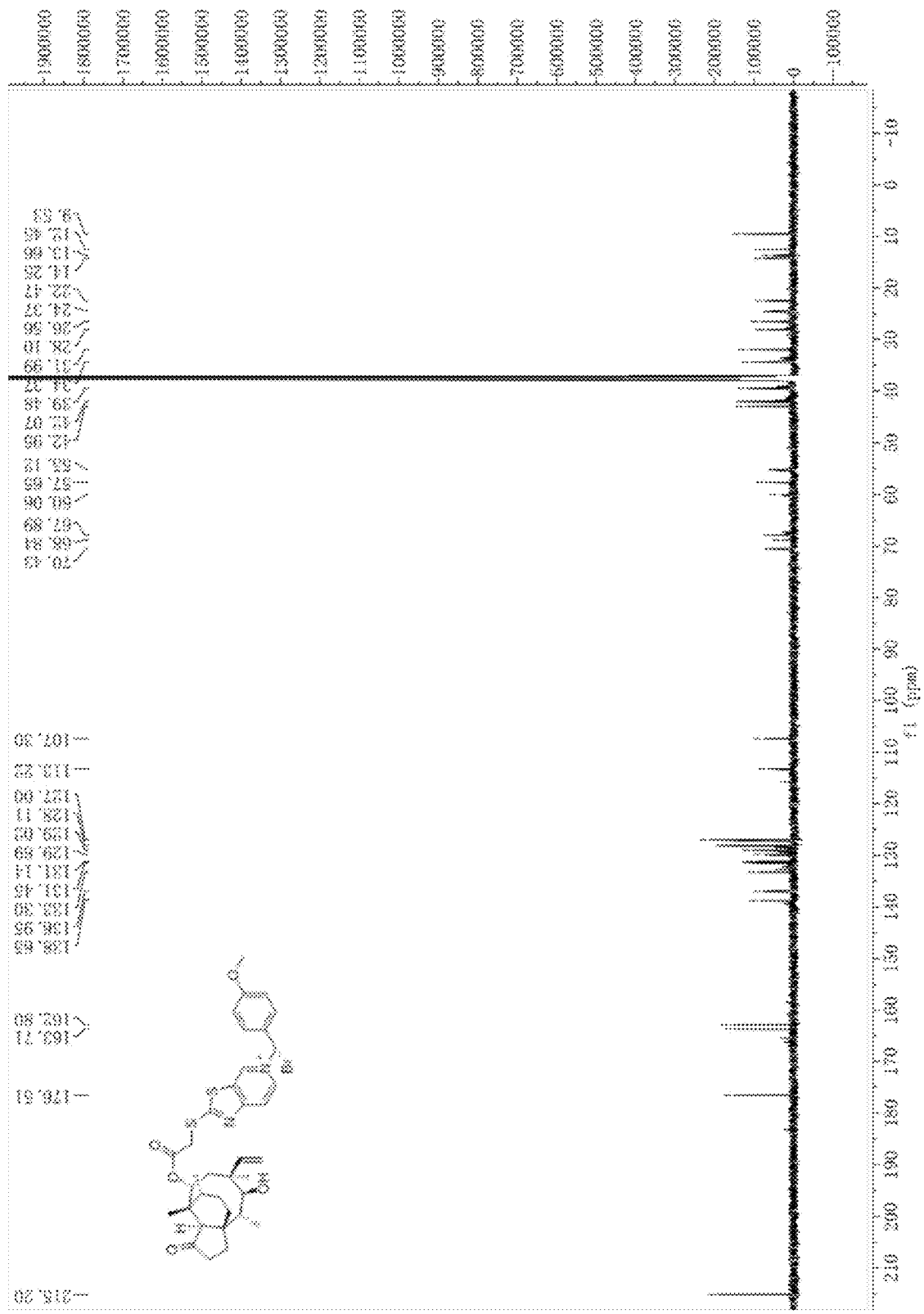
FIG. 8 is a $^{13}$C NMR spectrum of Compound I-4 of the present invention in deuterated DMSO.

The preparation method was as described in Example 1, except that the corresponding raw materials were replaced. Yield of Compound I-4 obtained: 87%. The ¹H NMR spectrum of compound I-4 in deuterated DMSO is shown in FIG. 7, and the ¹³C NMR spectrum in deuterated DMSO is shown in FIG. 8.

¹H NMR (600 MHZ, DMSO-d6) δ 9.88 (s, 1H), 8.79-8.70 (m, 1H), 8.67-8.60 (m, 1H), 8.34-8.24 (m, 1H), 7.60-7.56 (m, 2H), 7.54-7.46 (m, 2H), 6.18-6.13 (m, 1H), 6.05-6.01 (m, 1H), 5.56 (dd, J=14.7, 8.2 Hz, 1H), 5.45 (d, J=8.4 Hz, 1H), 5.07 (dd, J=13.4, 6.6, 1.8 Hz, 2H), 4.57-4.49 (m, 2H), 4.45-4.39 (m, 1H), 3.88 (s, 3H), 2.46-2.39 (m, 1H), 2.28-2.26 (m, 1H), 2.20 (dd, J=18.9, 10.6 Hz, 3H), 2.13-1.98 (m, 2H), 1.69-1.55 (m, 1H), 1.49 (d, J=7.9, 4.0 Hz, 4H), 1.44-1.35 (m, 4H), 1.35-1.15 (m, 3H), 1.10-0.88 (m, 1H), 0.81 (dd, J=18.8, 7.0 Hz, 3H), 0.64 (d, J=10.0, 5.0 Hz, 3H).

¹³C NMR (151 MHz, DMSO-d6) δ 215.20, 176.51, 163.71, 162.80, 138.65, 136.95, 133.30, 131.45, 131.14, 129.89, 129.02, 128.11, 127.00, 113.22, 107.30, 70.43, 68.84, 67.89, 60.06, 57.65, 55.12, 42.95, 42.07, 39.48, 34.37, 31.99, 28.10, 26.56, 24.37, 22.47, 14.25, 13.66, 12.45, 9.53.

Example 5

Preparation of Compound I-5:5-(4-chlorobenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8] cyclo-5-yl)oxy)-2-oxoethyl)thio)thiazolo[5,4-c]pyridin-5-ium

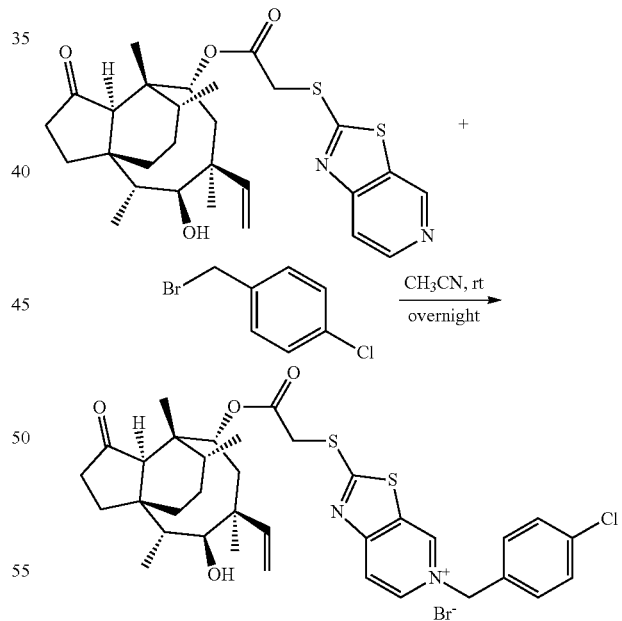

Figure 9:
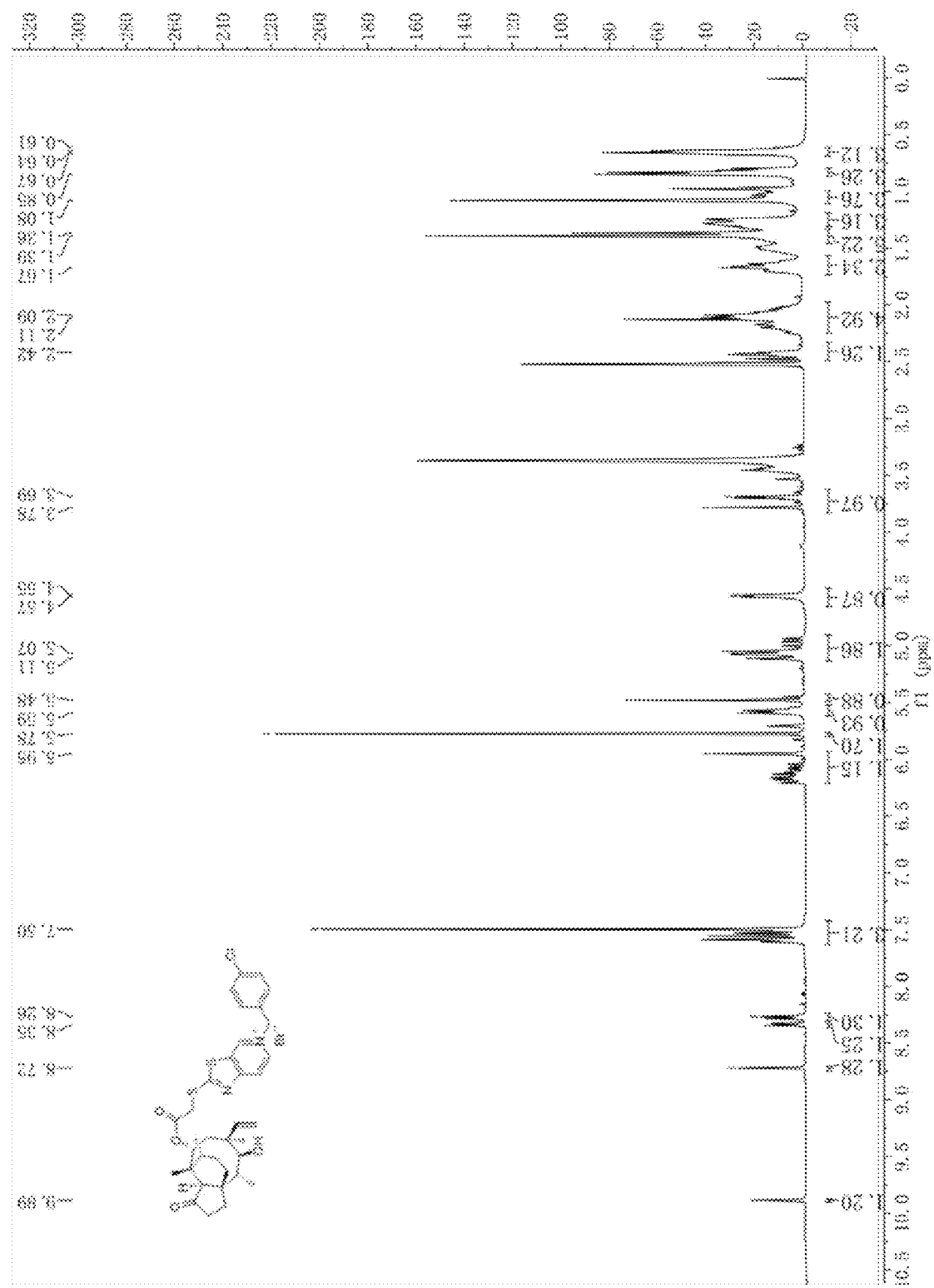
FIG. 9 is a $^1$H NMR spectrum of Compound I-5 of the present invention in deuterated DMSO.
Figure 10:
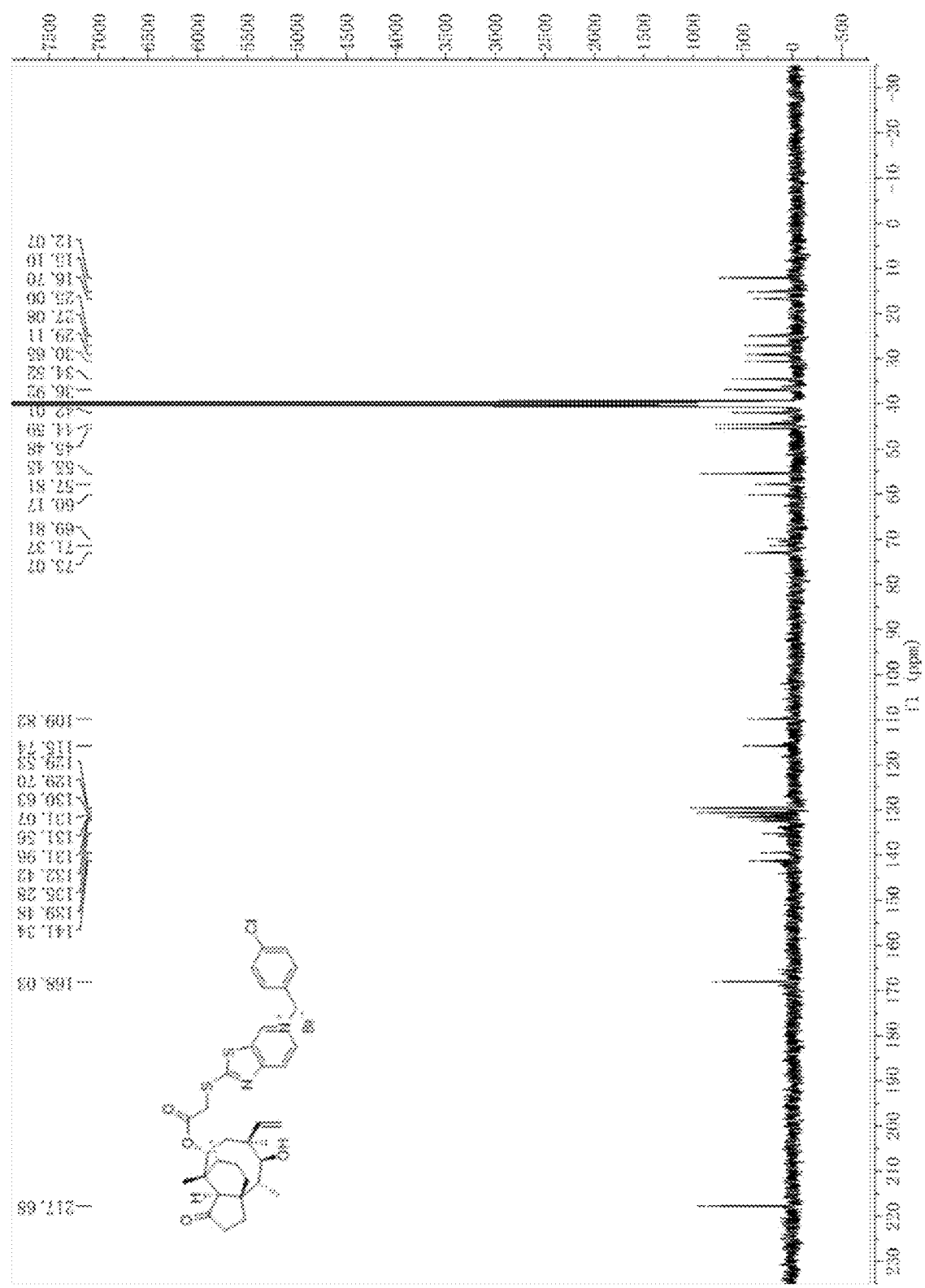
FIG. 10 is a $^{13}$C NMR spectrum of Compound I-5 of the present invention in deuterated DMSO.

The preparation method was as described in Example 1, except that the corresponding raw materials were replaced. Yield of Compound I-5 obtained: 74%. The ¹H NMR spectrum of compound I-2 in deuterated DMSO is shown in FIG. 9, and the ¹³C NMR spectrum in deuterated DMSO is shown in FIG. 10.

¹H NMR (600 MHZ, DMSO-d6) δ 9.89 (s, 1H), 8.72 (s, 1H), 8.35 (s, 1H), 8.26 (s, 1H), 7.50 (d, J=7.2 Hz, 3H), 5.95 (d, J=6.0 Hz, 1H), 5.78 (m, 2H), 5.59 (s, 1H), 5.48 (s, 1H), 5.09 (d, J=7.8 Hz, 2H), 4.56 (d, J=5.8 Hz, 1H), 3.79-3.65 (m, 1H), 2.39 (s, 1H), 2.10 (d, J=9.0 Hz, 5H), 1.67 (s, 2H), 1.45 (d, J=8.2 Hz, 5H), 1.38 (d, J=8.6 Hz, 3H), 1.08 (m, 4H), 0.85 (m, 3H), 0.65 (d, J=9.5 Hz, 3H).

$^{13}$C NMR (151 MHz, DMSO-d6) δ 217.68, 168.03, 141.34, 139.48, 135.28, 132.42, 131.96, 131.56, 131.07, 130.63, 129.70, 129.53, 115.74, 109.82, 73.07, 71.37, 69.81, 60.17, 57.81, 55.45, 45.48, 44.59, 42.01, 36.92, 34.52, 30.65, 29.11, 27.08, 25.00, 16.70, 15.10, 12.07.

Example 6

Preparation of Compound I-6:5-(4-nitrobenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8] cyclo-5-yl)oxy)-2-oxoethyl)thio)thiazolo[5,4-c]pyridin-5-ium

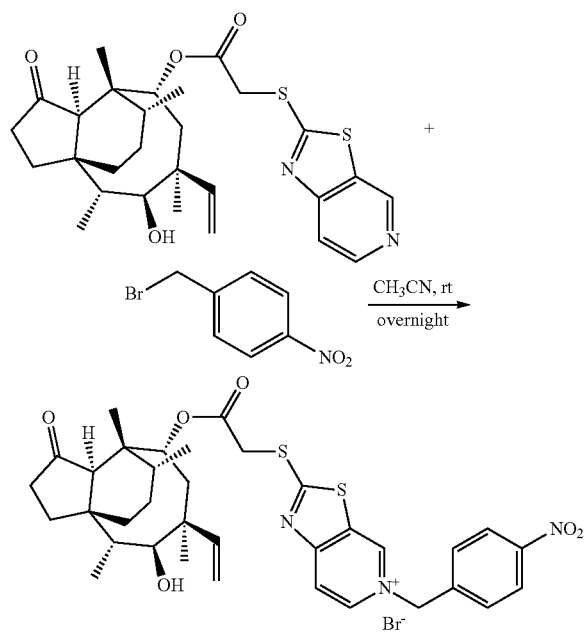

Figure 11:
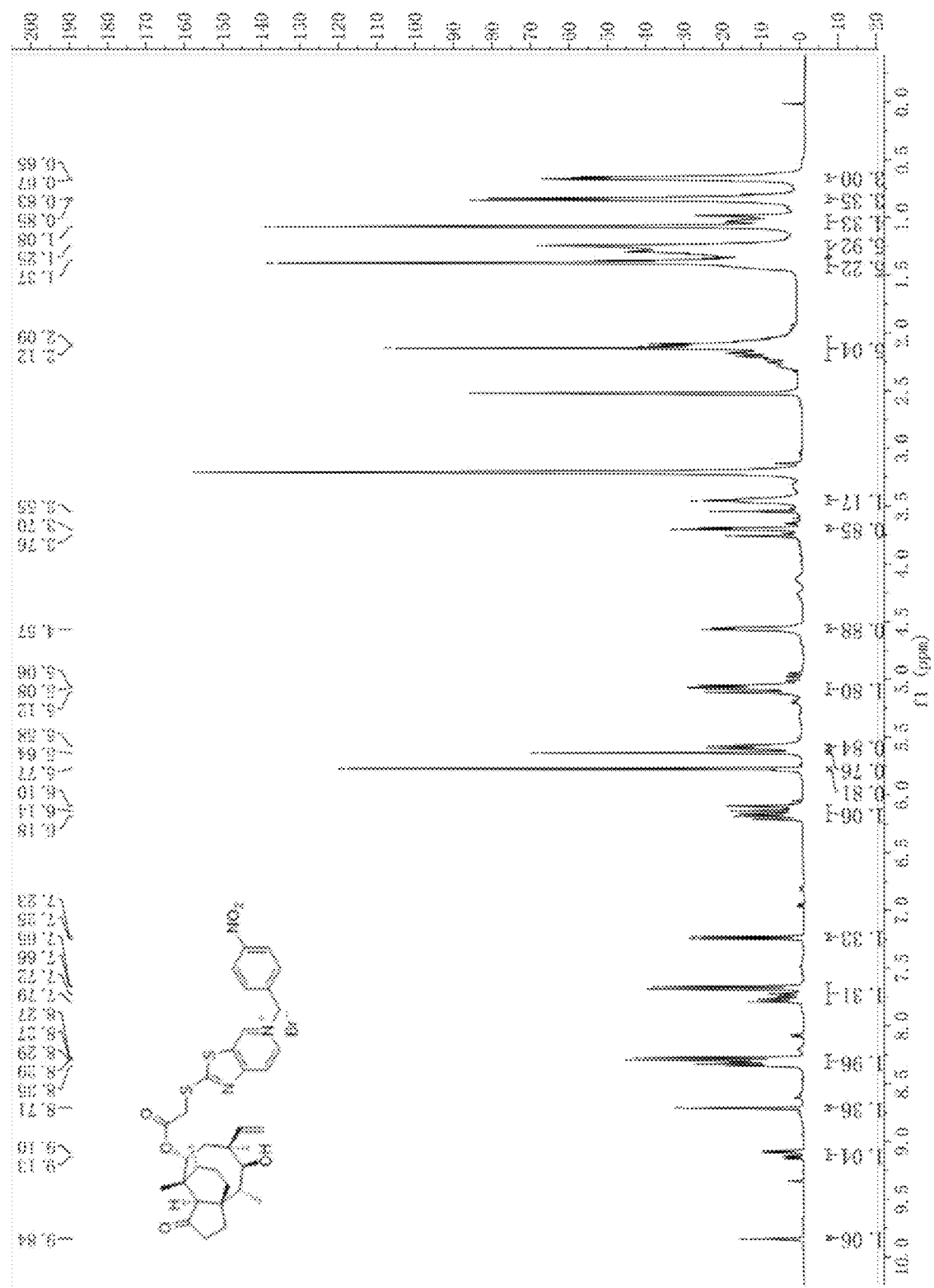
FIG. 11 is a $^1$H NMR spectrum of Compound I-6 of the present invention in deuterated DMSO.
Figure 12:
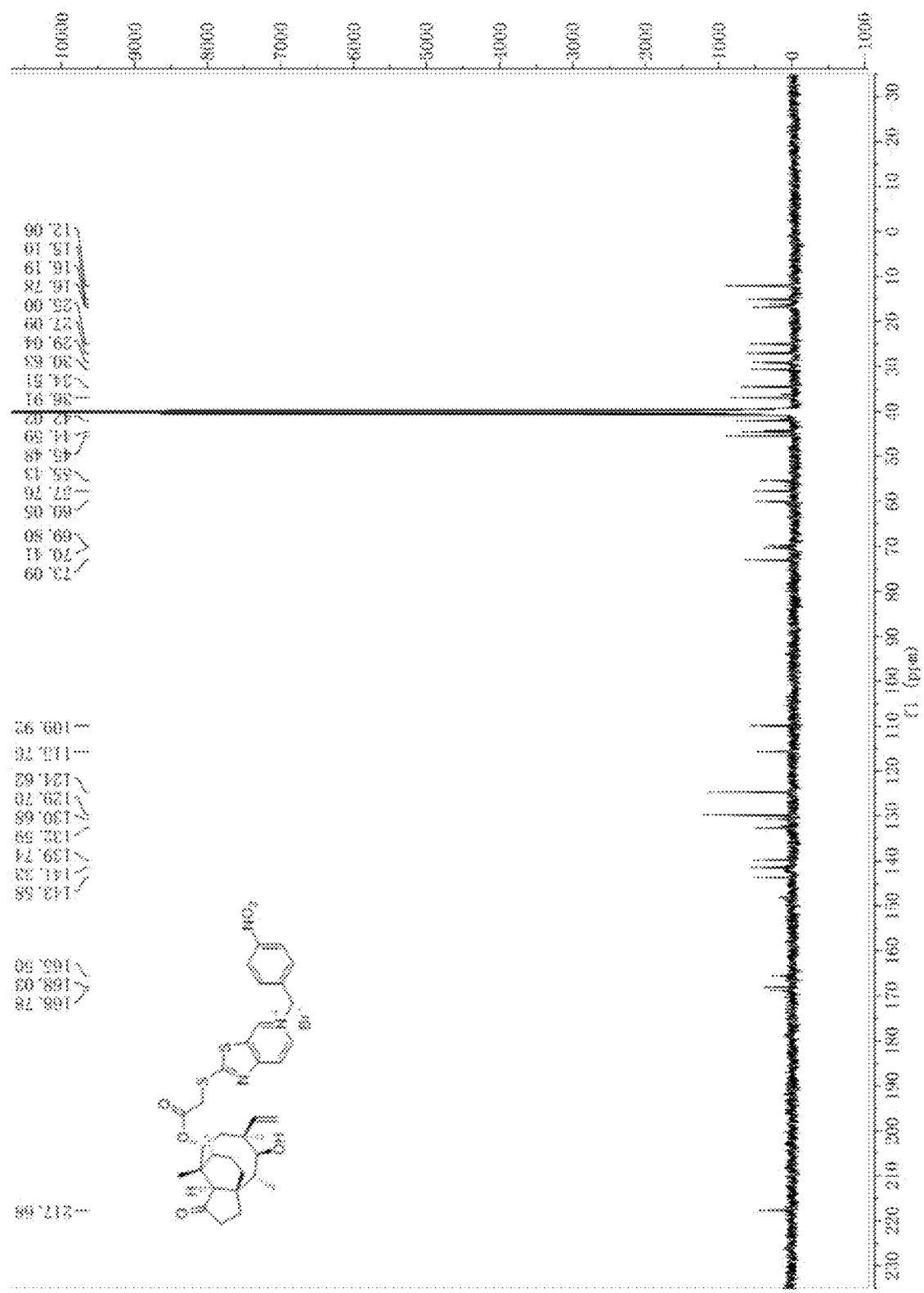
FIG. 12 is a $^{13}$C NMR spectrum of Compound I-6 of the present invention in deuterated DMSO.

The preparation method was as described in Example 1, except that the corresponding raw materials were replaced. Yield of Compound I-6 obtained: 86%. The $^1$H NMR spectrum of compound I-6 in deuterated DMSO is shown in FIG. 11, and the $^{13}$C NMR spectrum in deuterated DMSO is shown in FIG. 12.

$^1$H NMR (600 MHZ, DMSO-d6) δ 9.84 (d, J=1.6 Hz, 1H), 8.71 (d, J=1.7 Hz, 1H), 8.28 (d, J=8.8 Hz, 1H), 7.81-7.70 (m, 2H), 7.66-7.65 (m, 1H) 7.24 (d, J=7.0 Hz, 1H), 6.23-6.03 (m, 1H), 5.77-5.58 (m, 1H), 5.47-5.41 (m, 1H), 5.14-5.02 (m, 2H), 4.59-4.52 (m, 1H), 3.55 (s, 1H), 3.45 (q, J=6.8 Hz, 1H), 2.19-1.99 (m, 5H), 1.39 (d, J=1.8 Hz, 5H), 1.32-1.24 (m, 6H), 1.03 (d, J=7.8 Hz, 4H), 0.83 (dd, J=6.8 Hz, 3H), 0.73-0.60 (m, 3H).

$^{13}$C NMR (151 MHZ, DMSO-d6) δ 217.68, 168.78, 168.03, 165.50, 143.58, 141.33, 139.74, 132.59, 130.68, 129.70, 124.62, 115.76, 109.92, 73.09, 70.41, 69.80, 60.05, 57.76, 55.43, 45.48, 44.59, 42.02, 36.91, 34.51, 30.63, 29.04, 27.09, 25.00, 16.78, 16.19, 15.10, 12.06.

Example 7

Preparation of Compound I-7:5-(2,4,5-trifluorobenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8] cyclo-5-yl)oxy)-2-oxoethyl)thio)thiazolo[5,4-c]pyridin-5-ium

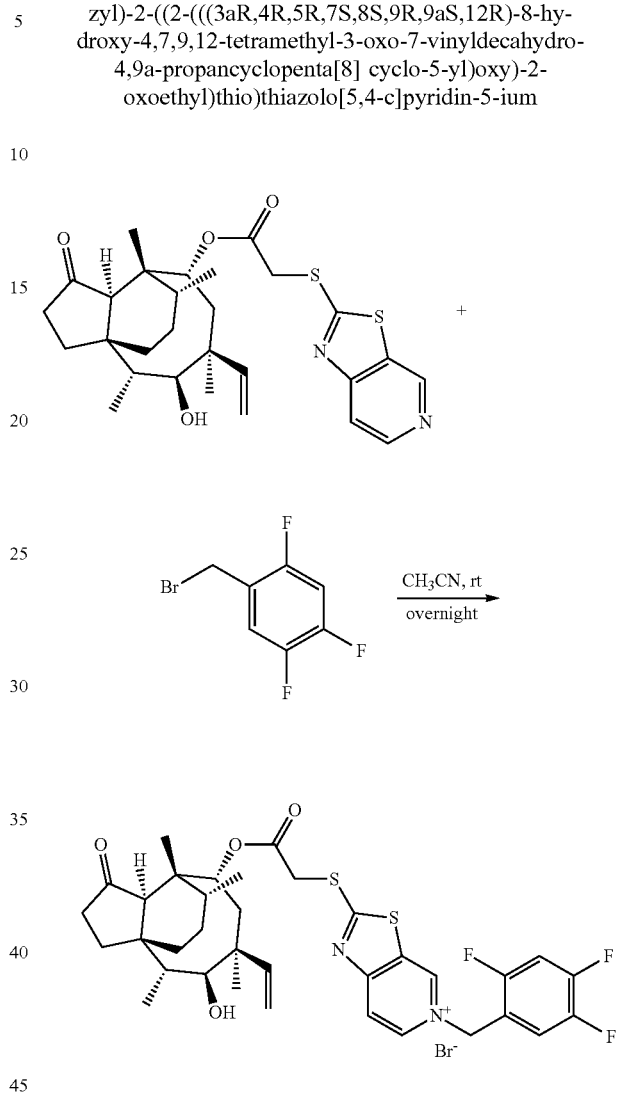

Figure 13:
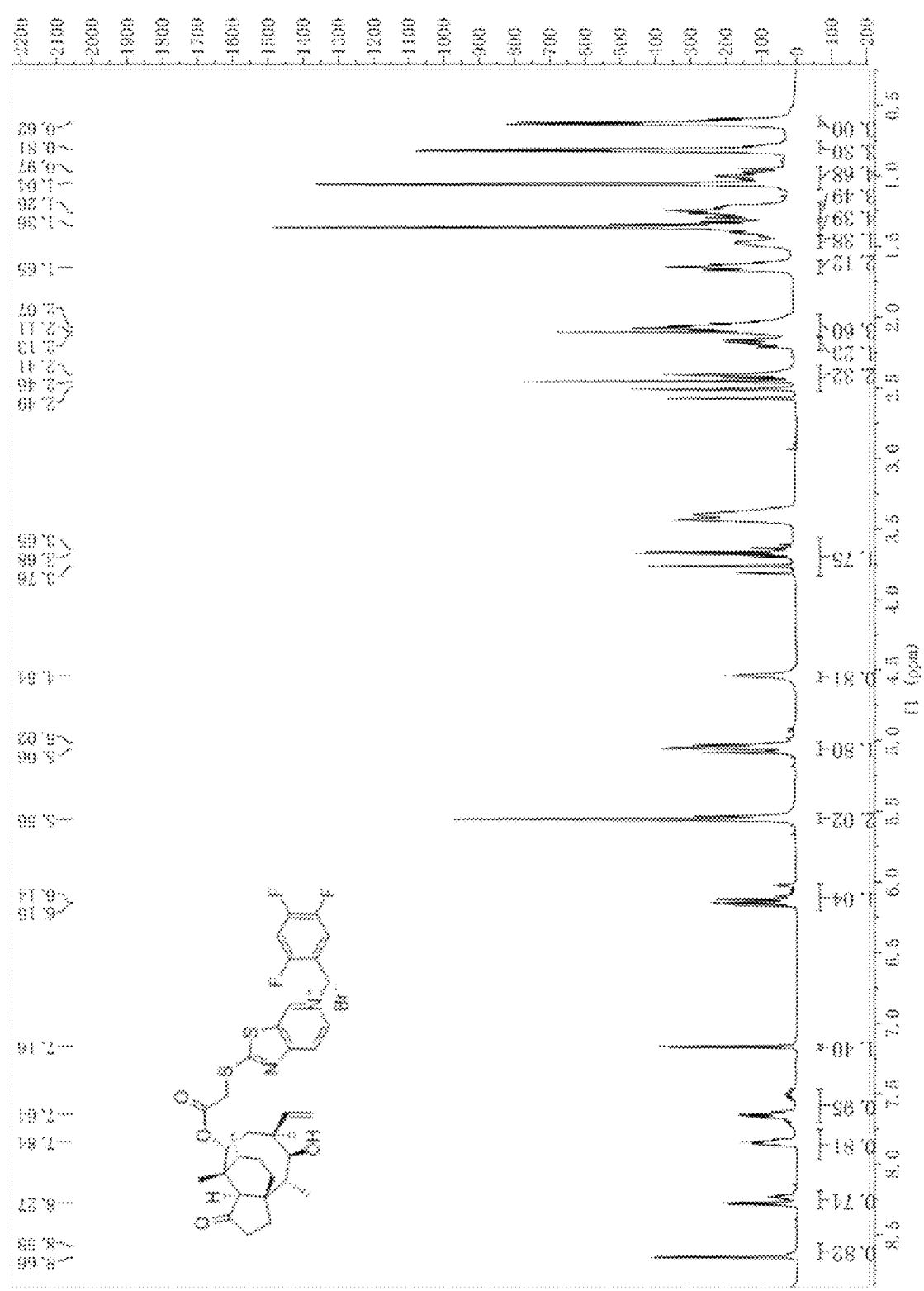
FIG. 13 is a $^1$H NMR spectrum of Compound I-7 of the present invention in deuterated DMSO.
Figure 14:
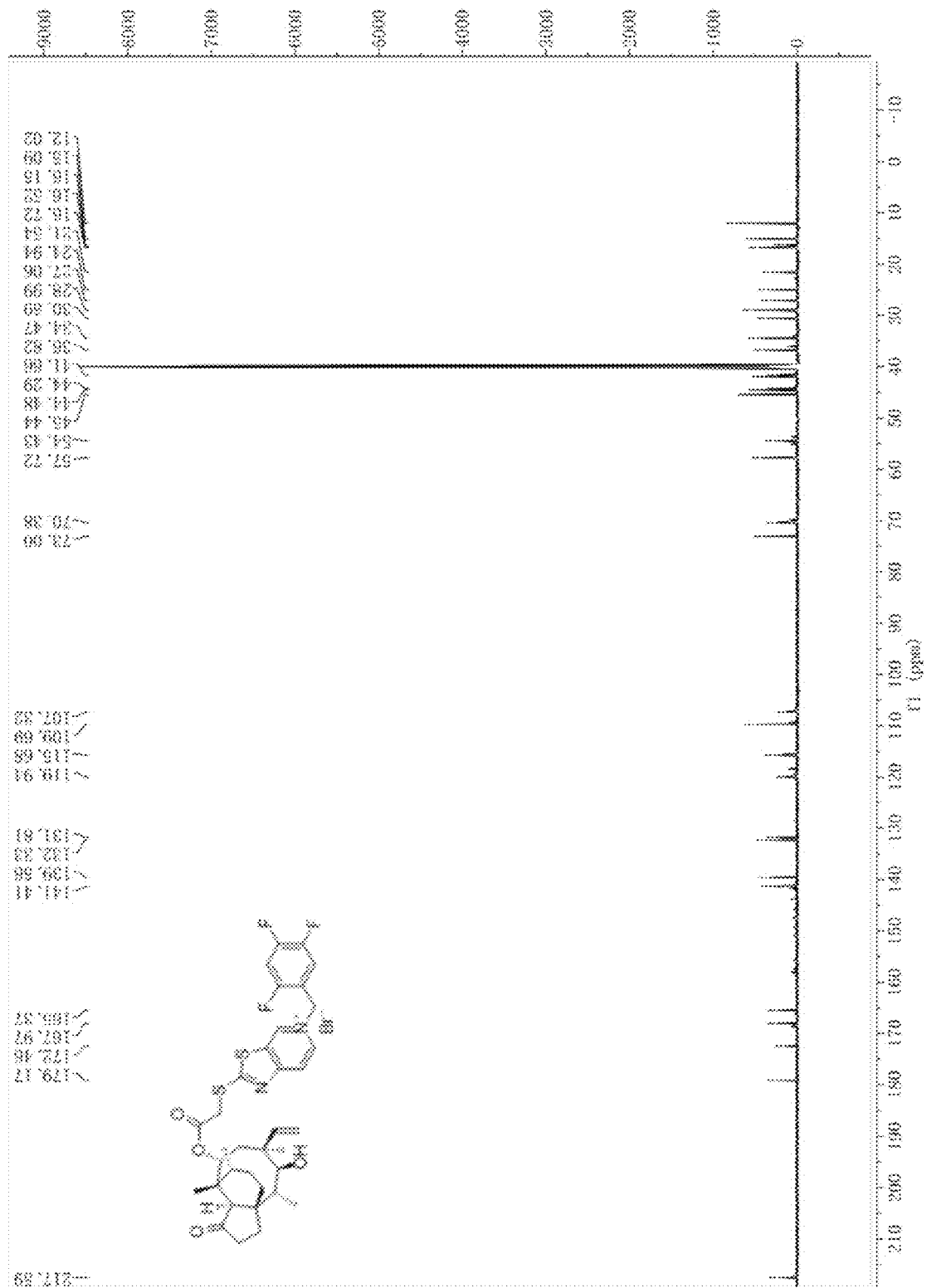
FIG. 14 is a $^{13}$C NMR spectrum of Compound I-7 of the present invention in deuterated DMSO.

The preparation method was as described in Example 1, except that the corresponding raw materials were replaced. Yield of Compound I-7 obtained: 80%. The $^1$H NMR spectrum of compound I-7 in deuterated DMSO is shown in FIG. 13, and the $^{13}$C NMR spectrum in deuterated DMSO is shown in FIG. 14.

$^1$H NMR (600 MHZ, DMSO-d6) δ 8.62 (dd, J=8.0, 1.7 Hz, 1H), 8.31-8.19 (m, 1H), 7.91-7.79 (m, 1H), 7.71-7.62 (m, 1H), 7.18-7.09 (m, 1H), 6.20-5.78 (m, 1H), 5.54 (d, J=12.6 Hz, 2H), 5.06 (dd, J=8.4, 11.5, 4.5, 2.4 Hz, 2H), 4.58-4.52 (m, 1H), 3.83-3.56 (m, 2H), 2.43 (d, J=28.5 Hz, 2H), 2.34-2.28 (m, 1H), 2.24-1.98 (m, 4H), 1.69-1.60 (m, 2H), 1.58-1.49 (m, 1H), 1.43-1.32 (m, 4H), 1.31-1.19 (m, 3H), 1.09-0.93 (m, 5H), 0.82 (d, J=6.9 Hz, 3H), 0.65-0.58 (m, 3H).

$^{13}$C NMR (151 MHZ, DMSO-d6) δ 217.59, 179.17, 172.46, 167.97, 165.37, 141.41, 139.56, 132.33, 131.81, 119.94, 115.68, 109.69, 107.32, 73.00, 70.38, 57.72, 54.43, 45.44, 44.48, 44.29, 41.66, 36.82, 34.47, 30.59, 28.99, 27.06, 24.94, 21.54, 16.72, 16.52, 16.15, 15.09, 12.02.

Example 8

Preparation of Compound I-8:5-(4-cyanobenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8] cyclo-5-yl)oxy)-2-oxoethyl)thio)thiazolo[5,4-c]pyridin-5-ium

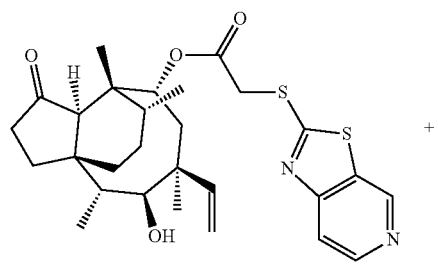

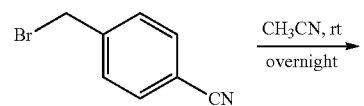

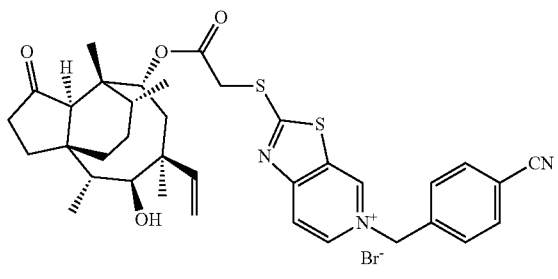

Figure 15:
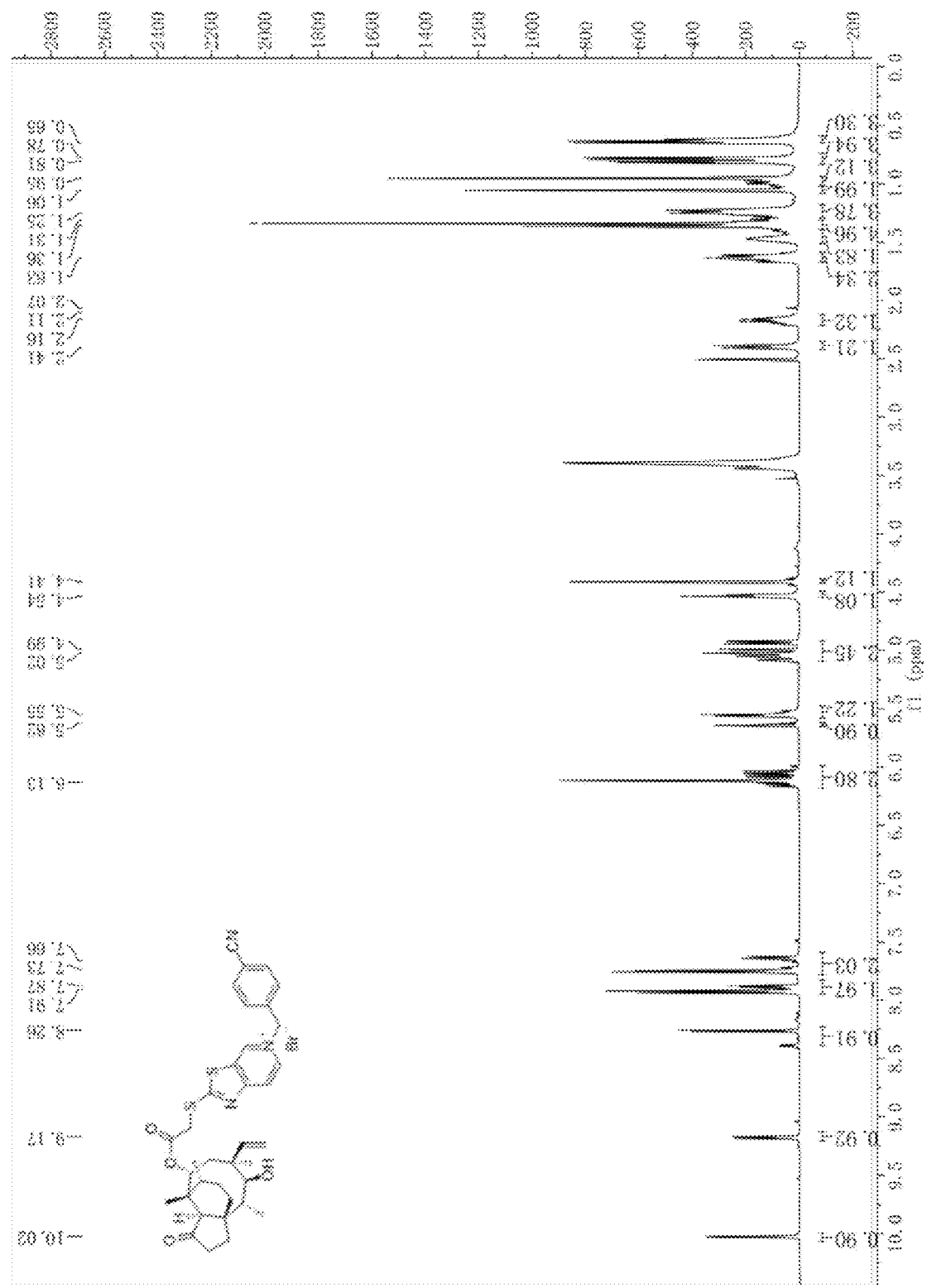
FIG. 15 is a $^1$H NMR spectrum of Compound I-8 of the present invention in deuterated DMSO.
Figure 16:
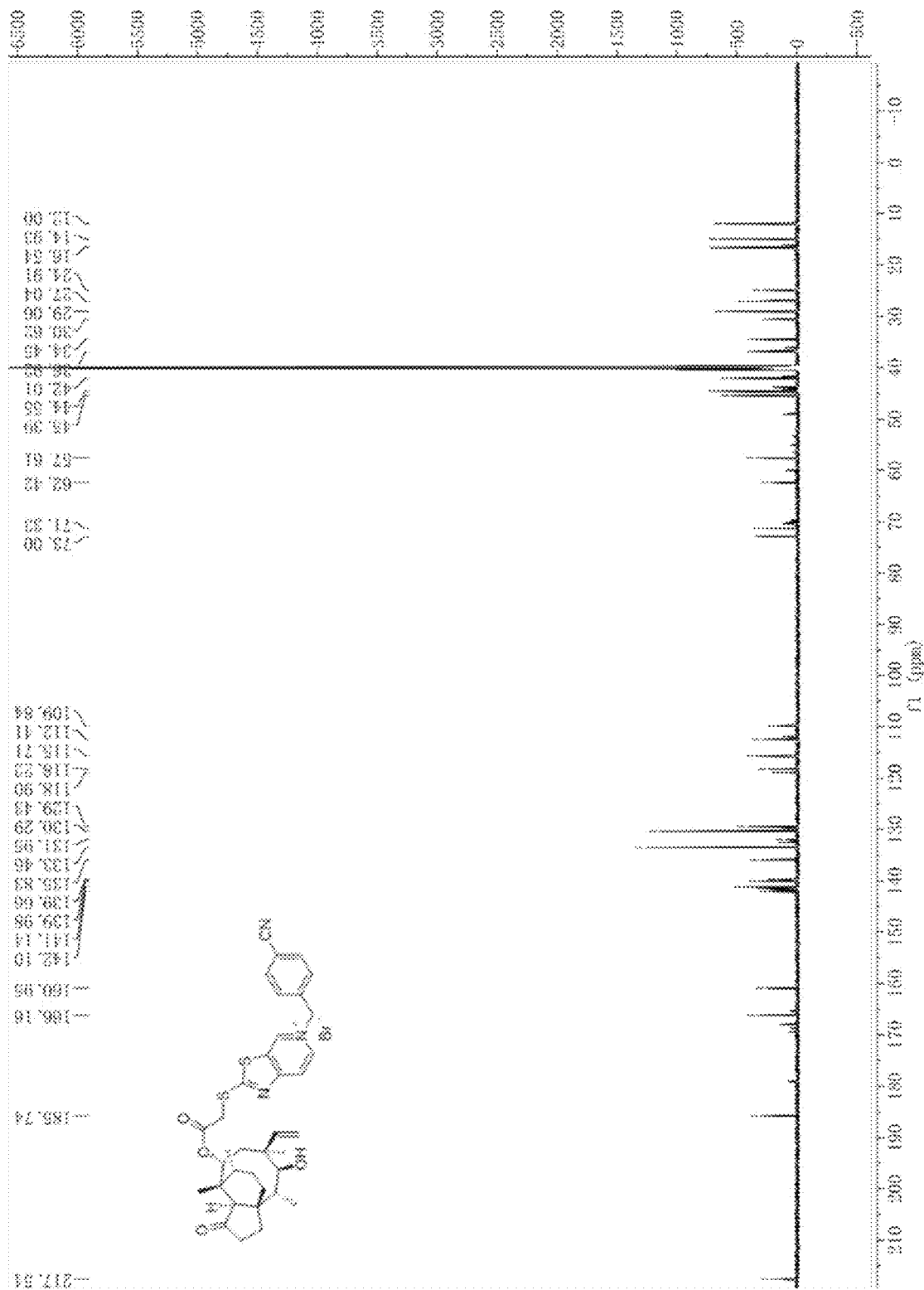
FIG. 16 is a $^{13}$C NMR spectrum of Compound I-8 of the present invention in deuterated DMSO.

The preparation method was as described in Example 1, except that the corresponding raw materials were replaced. Yield of Compound I-8 obtained: 88%. The $^1$H NMR spectrum of compound I-8 in deuterated DMSO is shown in FIG. 15, and the $^{13}$C NMR spectrum in deuterated DMSO is shown in FIG. 16.

$^1$H NMR (600 MHZ, DMSO-d6) δ 10.03 (t, J=2.1 Hz, 1H), 9.18 (d, J=2.4 Hz, 1H), 8.39-8.23 (m, 1H), 7.95-7.82 (m, 2H), 7.78-7.59 (m, 2H), 6.18-6.01 (m, 3H), 5.72 (d, J=6.2 Hz, 1H), 5.54 (dd, J=8.2 Hz, 1H), 5.09-4.88 (m, 2H), 4.53 (d, J=6.2 Hz, 1H), 4.42-4.39 (m, 1H), 2.40 (d, J=8.0 Hz, 1H), 2.18 (dd, J=17.6, 12.5, 7.5 Hz, 1H), 1.68-1.57 (m, 2H), 1.47 (dd, J=10.3, 5.5 Hz, 2H), 1.37-1.31 (m, 5H), 1.24 (dd, J=6.4 Hz, 4H), 1.09-1.03 (m, 2H), 1.01-0.92 (m, 3H), 0.80 (dd, J=18.4, 6.8 Hz, 4H), 0.66-0.60 (m, 3H).

$^{13}$C NMR (151 MHZ, DMSO-d6) δ 217.54, 185.74, 166.16, 160.95, 142.10, 141.14, 139.98, 139.66, 135.83, 133.46, 131.95, 130.29, 129.43, 118.90, 118.22, 115.71, 112.41, 109.84, 73.00, 71.33, 62.42, 57.61, 45.39, 44.55, 42.01, 36.92, 34.45, 30.62, 29.06, 27.04, 24.91, 16.54, 14.93, 12.00.

Example 9

Preparation of Compound I-9:5-(4-methylbenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8] cyclo-5-yl)oxy)-2-oxoethyl)thio)thiazolo[5,4-c]pyridin-5-ium

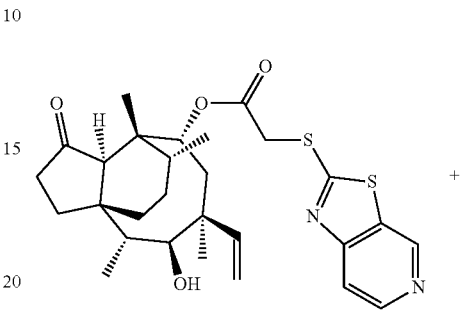

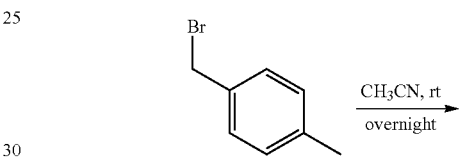

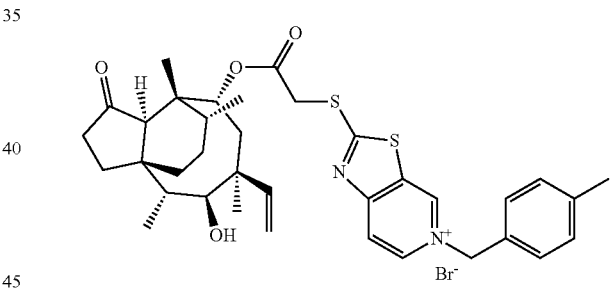

Figure 17:
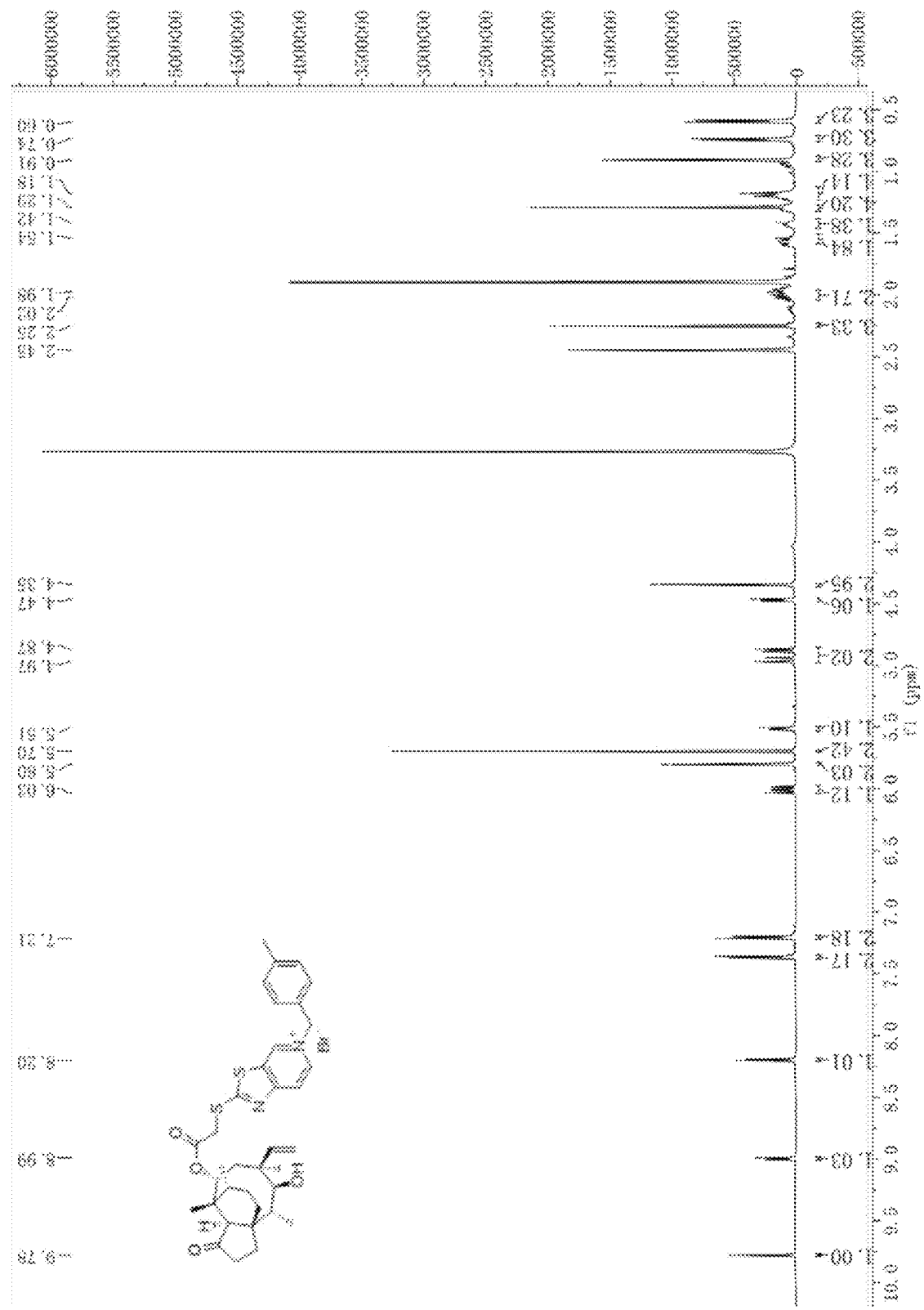
FIG. 17 is a $^1$H NMR spectrum of Compound I-9 of the present invention in deuterated DMSO.
Figure 18:
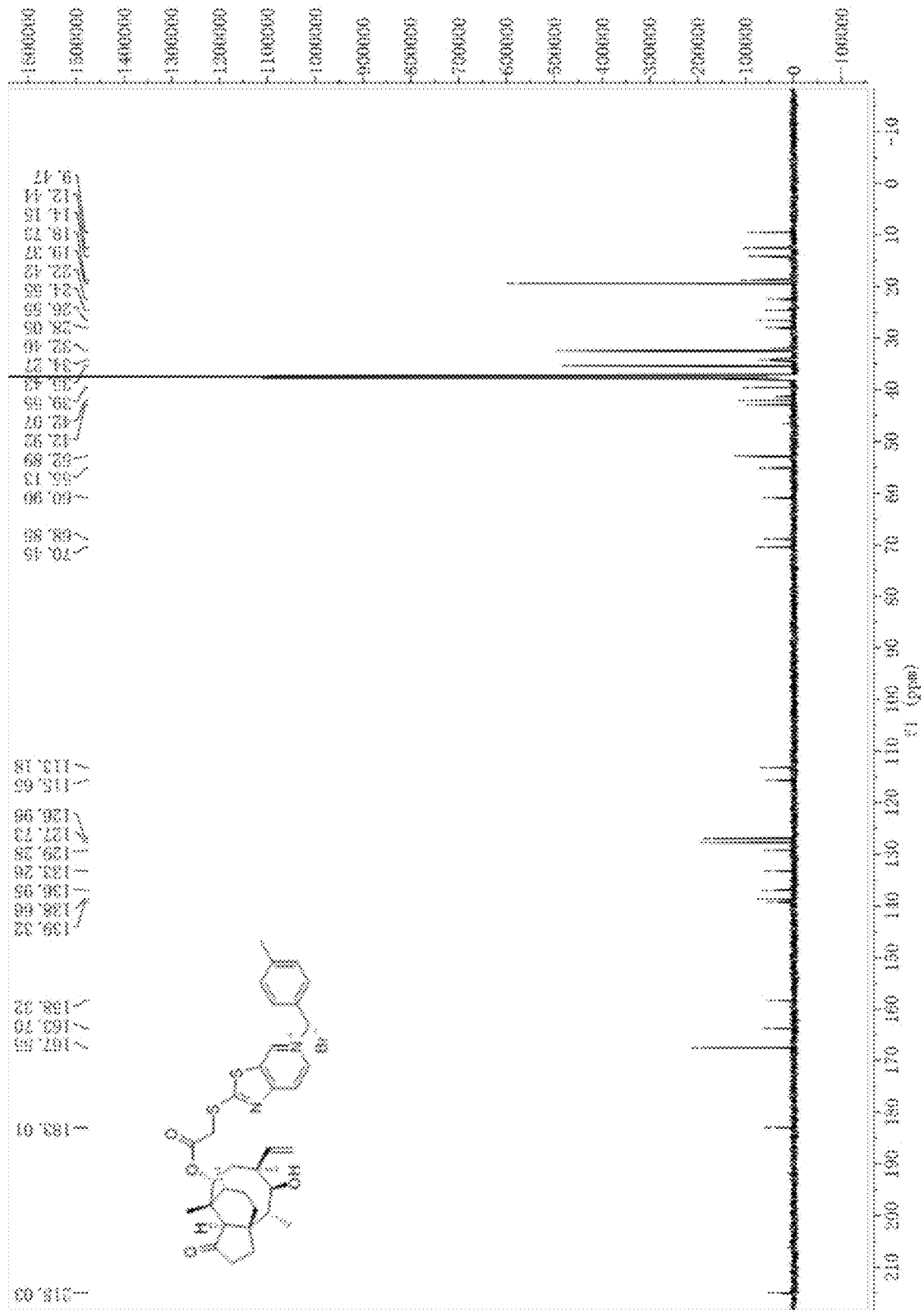
FIG. 18 is a $^{13}$C NMR spectrum of Compound I-9 of the present invention in deuterated DMSO.

The preparation method was as described in Example 1, except that the corresponding raw materials were replaced. Yield of Compound I-9 obtained: 84%. The $^1$H NMR spectrum of compound I-9 in deuterated DMSO is shown in FIG. 17, and the $^{13}$C NMR spectrum in deuterated DMSO is shown in FIG. 18.

$^1$H NMR (600 MHZ, DMSO-d6) δ 9.78 (d, J=1.5 Hz, 1H), 9.00 (dd, J=6.9, 1.5 Hz, 1H), 8.19 (d, J=6.9 Hz, 1H), 7.38-7.34 (m, 2H), 7.21 (d, J=8.0 Hz, 2H), 6.01 (dd, J=11.2 Hz, 1H), 5.80 (s, 2H), 5.70 (s, 2H), 5.51 (d, J=8.4 Hz, 1H), 4.98-4.86 (m, 2H), 4.47 (d, J=6.0 Hz, 1H), 4.35 (s, 3H), 2.25 (p, J=1.8 Hz, 3H), 2.02 (s, 3H), 1.57 (tdd, J=13.0, 10.5, 5.2 Hz, 2H), 1.47 (m, 1H), 1.29 (s, 4H), 1.23-1.13 (m, 4H), 0.91 (s, 3H), 0.74 (d, J=7.0 Hz, 3H), 0.59 (d, J=7.1 Hz, 3H).

$^{13}$C NMR (151 MHZ, DMSO-d6) δ 215.03, 183.01, 167.55, 163.70, 158.32, 139.32, 138.66, 136.95, 133.26, 129.28, 127.73, 126.96, 115.65, 113.18, 70.45, 68.85, 60.90, 55.13, 52.89, 42.92, 42.07, 39.55, 35.43, 34.27, 32.46, 28.05, 26.55, 24.55, 22.42, 19.37, 18.73, 14.15, 12.44, 9.47.

Example 10

Preparation of Compound I-10:5-([1,1'-biphenyl]-4-ylmethyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8] cyclo-5-yl)oxy)-2-oxoethyl)thio)thiazolo[5,4-c]pyridin-5-ium

Example 11

Preparation of Compound I-11:5-(4-(tert-butyl)benzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8] cyclo-5-yl)oxy)-2-oxoethyl)thio)thiazolo[5,4-c]pyridin-5-ium

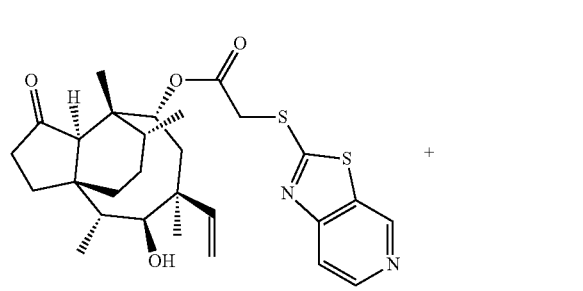

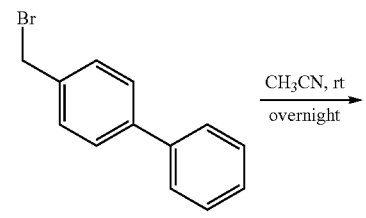

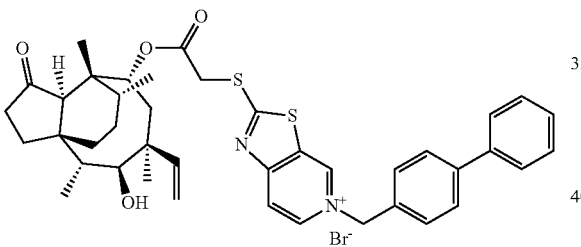

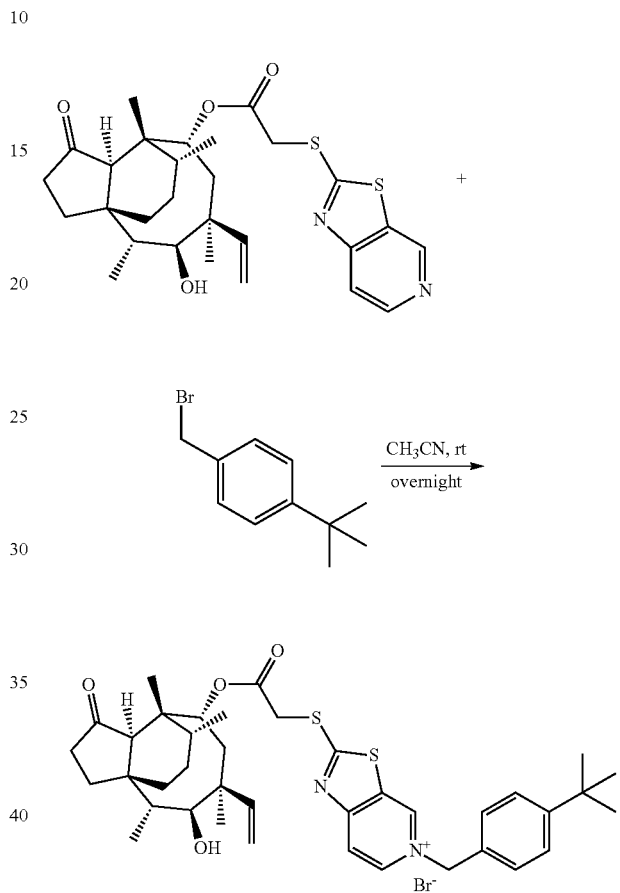

Figure 19:
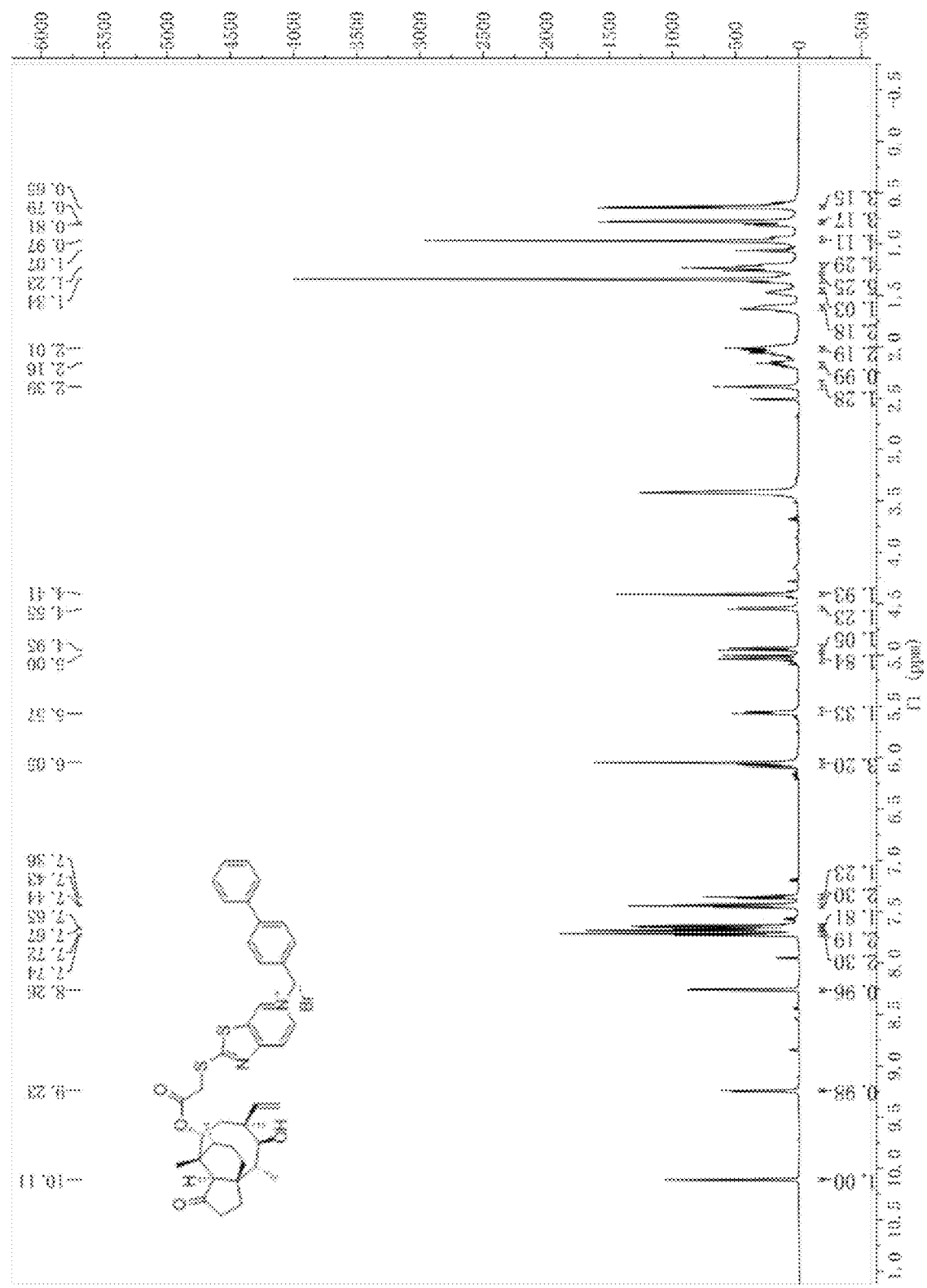
FIG. 19 is a $^1$H NMR spectrum of Compound I-10 of the present invention in deuterated DMSO.
Figure 20:
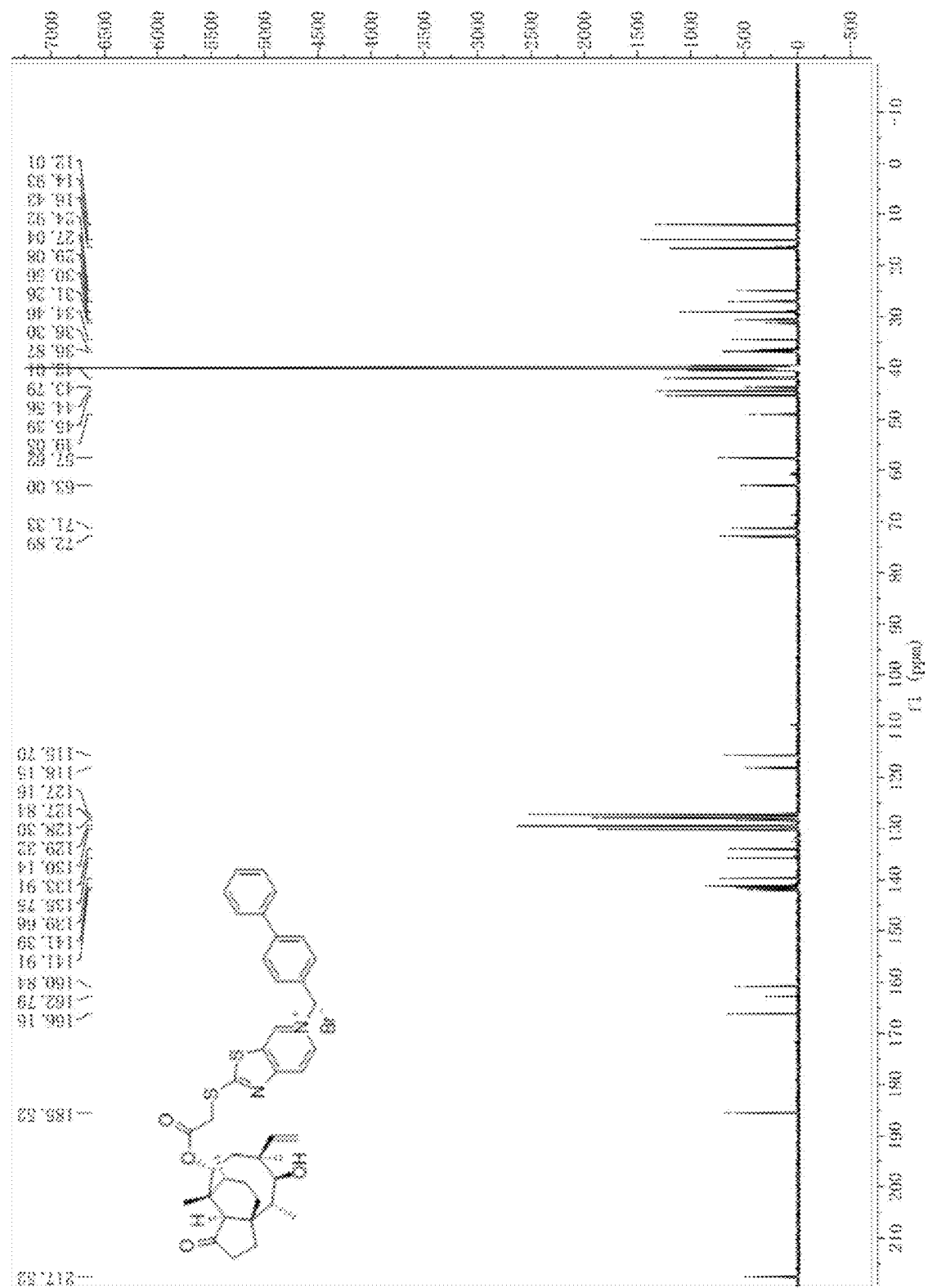
FIG. 20 is a $^{13}$C NMR spectrum of Compound I-10 of the present invention in deuterated DMSO.

The preparation method was as described in Example 1, except that the corresponding raw materials were replaced. Yield of Compound I-10 obtained: 84%. The $^1$H NMR spectrum of compound I-10 in deuterated DMSO is shown in FIG. 19, and the $^{13}$C NMR spectrum in deuterated DMSO is shown in FIG. 20.

$^1$H NMR (600 MHZ, DMSO-d6) δ 10.11 (d, J=1.5 Hz, 1H), 9.24 (dd, J=7.0, 1.6 Hz, 1H), 8.26 (d, J=6.9 Hz, 1H), 7.74-7.69 (m, 2H), 7.69-7.66 (m, 2H), 7.65-7.62 (m, 2H), 7.44 (dd, J=8.4, 7.1 Hz, 2H), 7.38-7.33 (m, 1H), 6.10-6.01 (m, 3H), 5.59-5.52 (m, 1H), 5.03 (td, J=17.2, 2.8 Hz, 2H), 4.94 (dd, J=11.2, 1.7 Hz, 1H), 4.55 (d, J=6.1 Hz, 1H), 4.43-4.38 (m, 2H), 2.39 (s, 1H), 2.19-2.12 (m, 1H), 2.09-1.94 (m, 2H), 1.72-1.60 (m, 2H), 1.53-1.46 (m, 1H), 1.38-1.30 (m, 5H), 1.28-1.19 (m, 4H), 0.99-0.93 (m, 4H), 0.78 (d, J=6.9 Hz, 3H), 0.64 (d, J=7.1 Hz, 3H).

$^{13}$C NMR (151 MHZ, DMSO-d6) δ 217.52, 185.52, 166.16, 162.79, 160.84, 141.91, 141.39, 139.66, 135.75, 133.91, 130.14, 129.32, 128.30, 127.84, 127.16, 118.15, 115.70, 72.89, 71.33, 63.00, 57.62, 49.05, 45.39, 44.56, 43.79, 42.01, 36.87, 36.30, 34.46, 31.26, 30.56, 29.08, 27.04, 24.92, 16.43, 14.93, 12.01.

Figure 21:
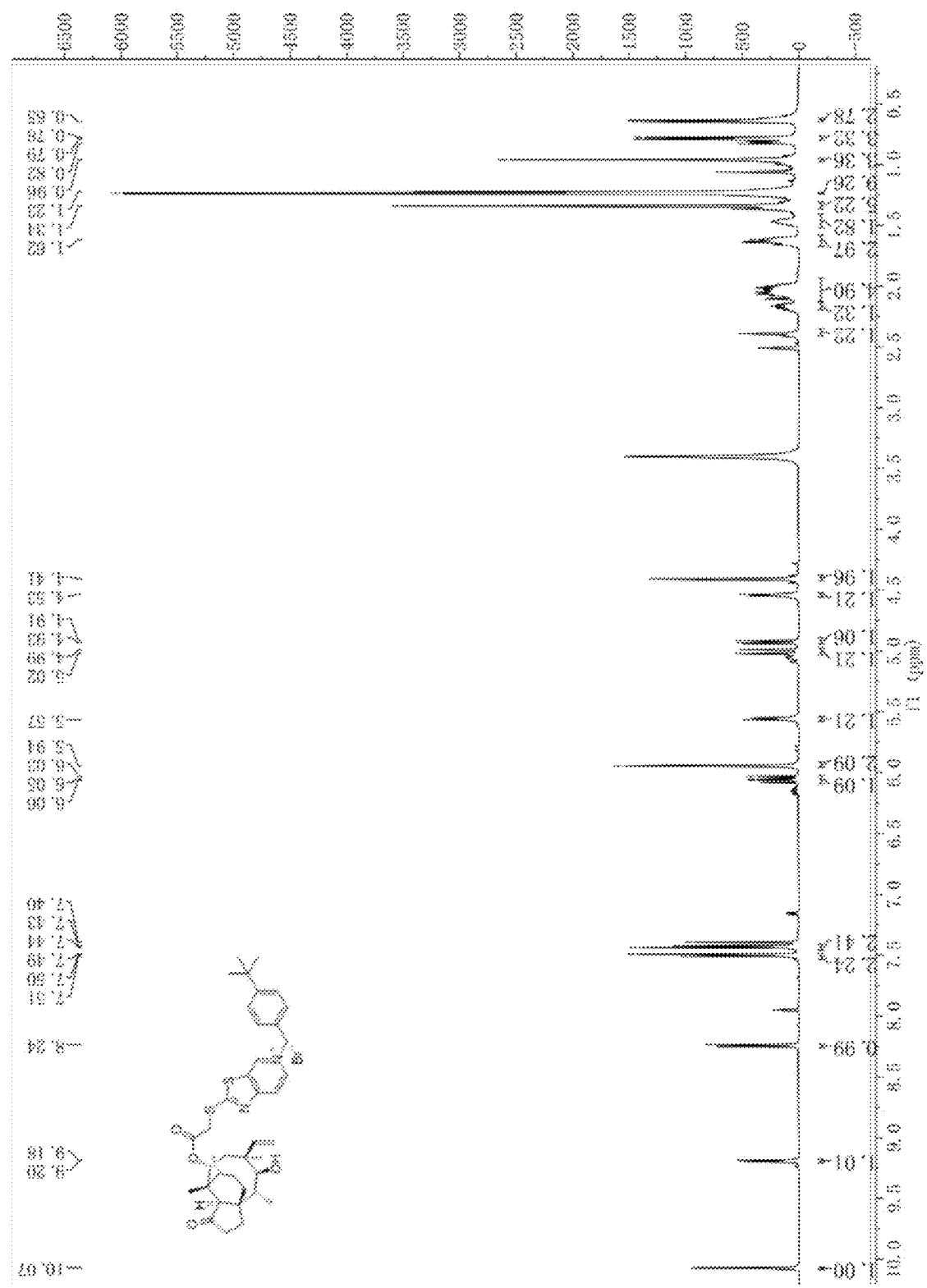
FIG. 21 is a $^1$H NMR spectrum of Compound I-11 of the present invention in deuterated DMSO.
Figure 22:
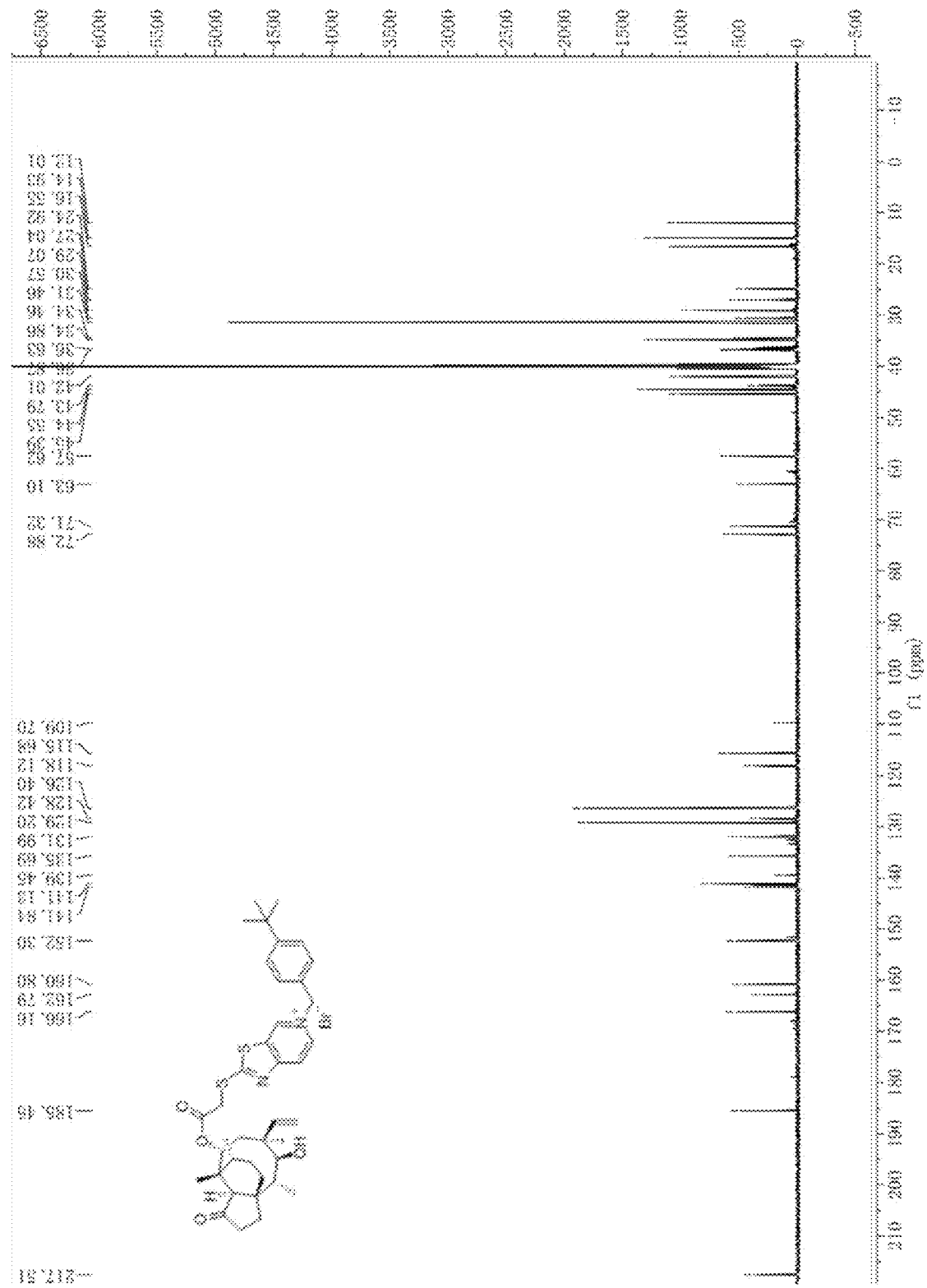
FIG. 22 is a $^{13}$C NMR spectrum of Compound I-11 of the present invention in deuterated DMSO.

The preparation method was as described in Example 1, except that the corresponding raw materials were replaced. Yield of Compound I-11 obtained: 75%. The $^1$H NMR spectrum of compound I-11 in deuterated DMSO is shown in FIG. 21, and the $^{13}$C NMR spectrum in deuterated DMSO is shown in FIG. 22.

$^1$H NMR (600 MHZ, DMSO-d6) δ 10.07 (d, J=1.5 Hz, 1H), 9.19 (dd, J=6.9, 1.5 Hz, 1H), 8.24 (d, J=6.8 Hz, 1H), 7.54-7.49 (m, 2H), 7.46-7.41 (m, 2H), 6.19-6.02 (m, 1H), 5.94 (s, 2H), 5.56 (d, J=8.4 Hz, 1H), 5.09-4.97 (m, 1H), 4.92 (dd, J=11.2, 1.7 Hz, 1H), 4.54 (d, J=6.1 Hz, 1H), 4.42-4.37 (m, 2H), 2.49-2.46 (m, 1H), 2.41-2.32 (m, 1H), 2.18-1.88 (m, 5H), 1.78-1.69 (m, 2H), 1.67-1.58 (m, 2H), 1.37-1.31 (m, 5H), 1.23 (d, J=5.7 Hz, 9H), 0.96 (s, 3H), 0.78 (d, J=7.0 Hz, 3H), 0.63 (d, J=6.6 Hz, 3H).

$^{13}$C NMR (151 MHz, DMSO-d6) δ 217.51, 185.45, 166.16, 162.79, 160.80, 152.30, 141.84, 141.13, 139.45, 135.69, 131.99, 129.20, 128.42, 126.40, 118.12, 115.68, 109.70, 72.88, 71.32, 63.10, 57.62, 45.39, 44.55, 43.79, 42.01, 36.87, 36.63, 34.86, 34.46, 31.46, 30.57, 29.07, 27.04, 24.92, 16.55, 14.93, 12.01.

Example 12

Preparation of Compound I-12:5-(3,5-dimethylbenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8] cyclo-5-yl)oxy)-2-oxoethyl)thio)thiazolo[5,4-c]pyridin-5-ium

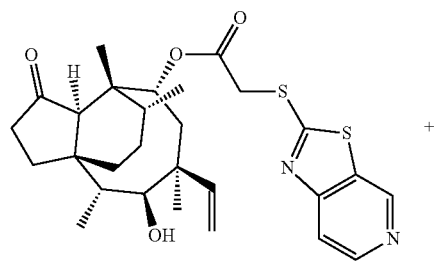

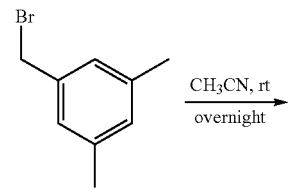

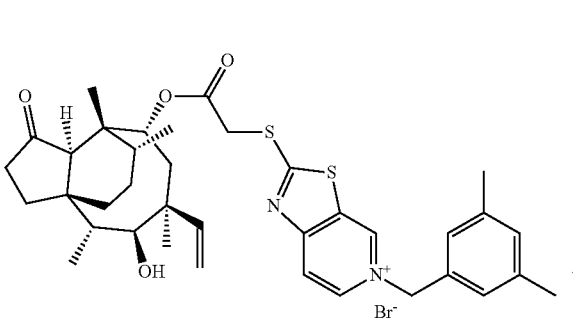

Figure 23:
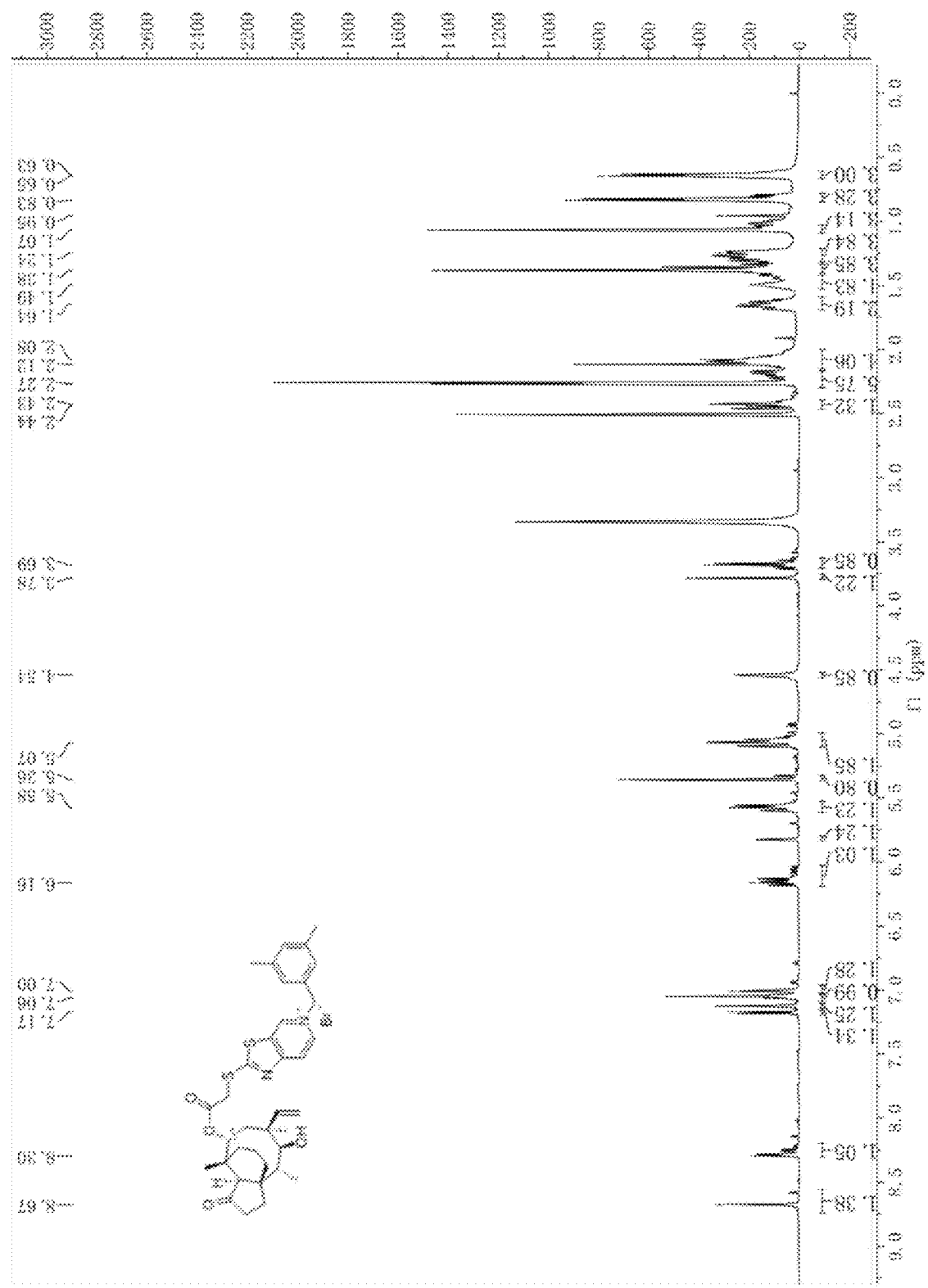
FIG. 23 is a $^1$H NMR spectrum of Compound I-12 of the present invention in deuterated DMSO.
Figure 24:
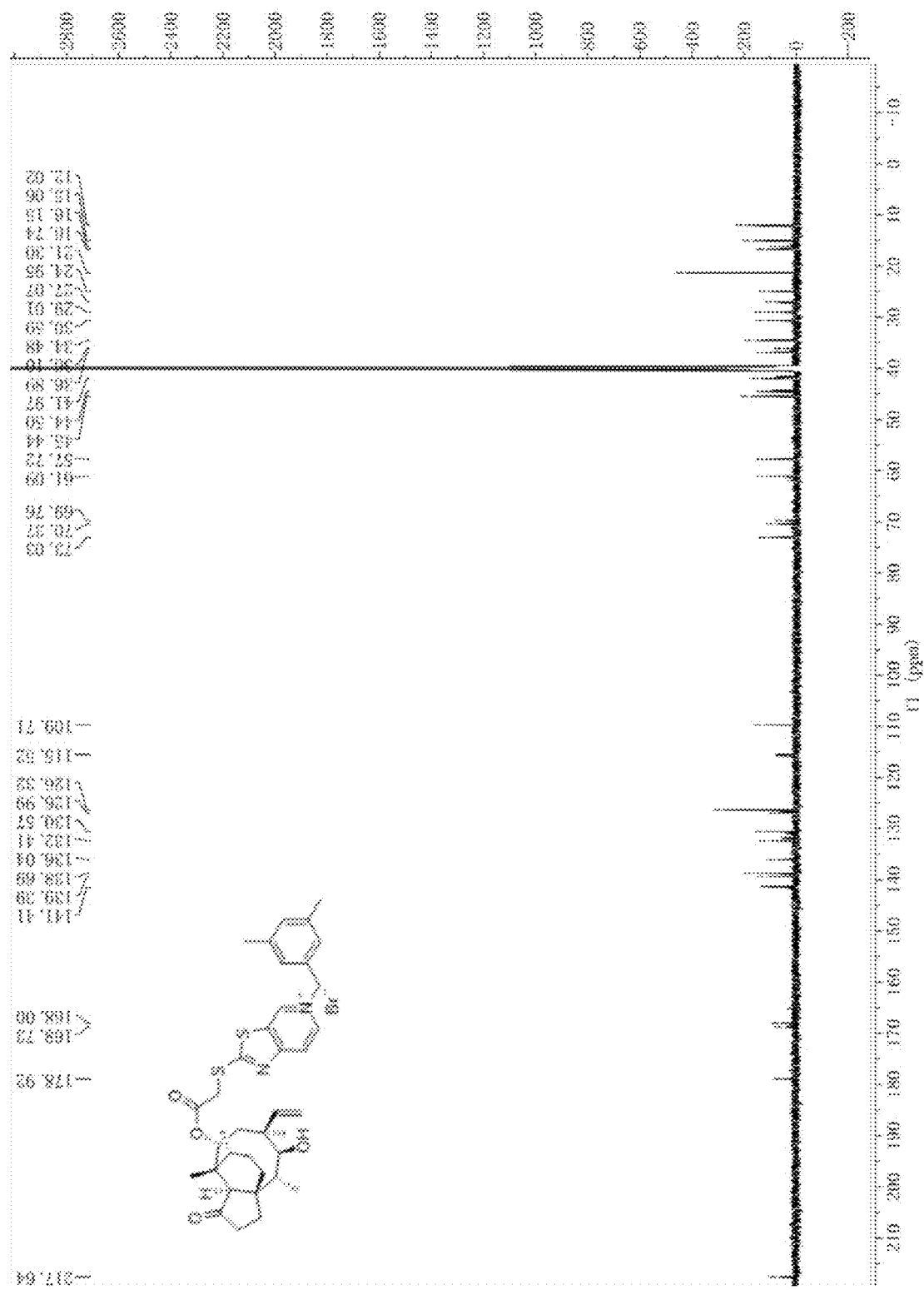
FIG. 24 is a $^{13}$C NMR spectrum of Compound I-12 of the present invention in deuterated DMSO.

The preparation method was as described in Example 1, except that the corresponding raw materials were replaced. Yield of Compound I-12 obtained: 89%. The $^1$H NMR spectrum of compound I-12 in deuterated DMSO is shown in FIG. 23, and the $^{13}$C NMR spectrum in deuterated DMSO is shown in FIG. 24.

$^1$H NMR (600 MHZ, DMSO-d6) δ 8.74-8.55 (m, 1H), 8.30-8.20 (m, 1H), 7.25-7.21 (m, 1H), 7.18-7.14 (m, 1H), 7.12-7.08 (m, 1H), 7.06-6.90 (m, 1H), 6.19-6.03 (m, 1H), 5.57 (q, J=11.9 Hz, 1H), 5.78 (s, 1H), 5.34 (d, J=17.9 Hz, 1H), 5.10-4.99 (m, 2H), 4.54 (dt, J=5.5, 2.6 Hz, 1H), 3.79-3.52 (m, 2H), 3.47-3.40 (m, 1H), 2.43 (dd, J=22.2, 11.8 Hz, 1H), 2.29-2.14 (m, 6H), 2.13-1.99 (m, 4H), 1.66 (dd, J=6.6 Hz, 2H), 1.52-1.42 (m, 2H), 1.40-1.33 (m, 4H), 1.32-1.21 (m, 4H), 1.09-1.03 (m, 3H), 0.85-0.78 (m, 3H), 0.64 (d, J=3.5 Hz, 3H).

$^{13}$C NMR (151 MHZ, DMSO-d6) δ 217.64, 178.92, 168.73, 168.00, 141.41, 139.39, 138.69, 136.04, 132.41, 130.57, 126.99, 126.32, 115.52, 109.71, 73.03, 70.37, 69.76, 61.09, 57.72, 45.44, 44.50, 41.97, 36.89, 36.10, 34.48, 30.59, 29.01, 27.07, 24.95, 21.30, 16.74, 16.15, 15.06, 12.02.

Example 13

Preparation of Compound I-13:5-(2-cyano-5-fluorobenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8] cyclo-5-yl)oxy)-2-oxoethyl)thio)thiazolo[5,4-c]pyridin-5-ium

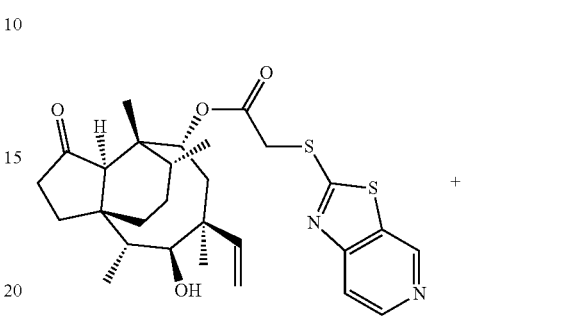

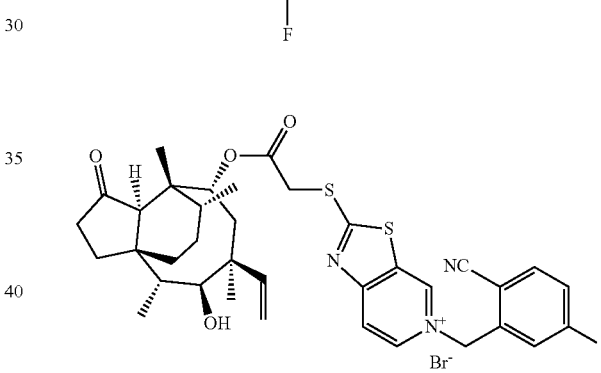

Figure 25:
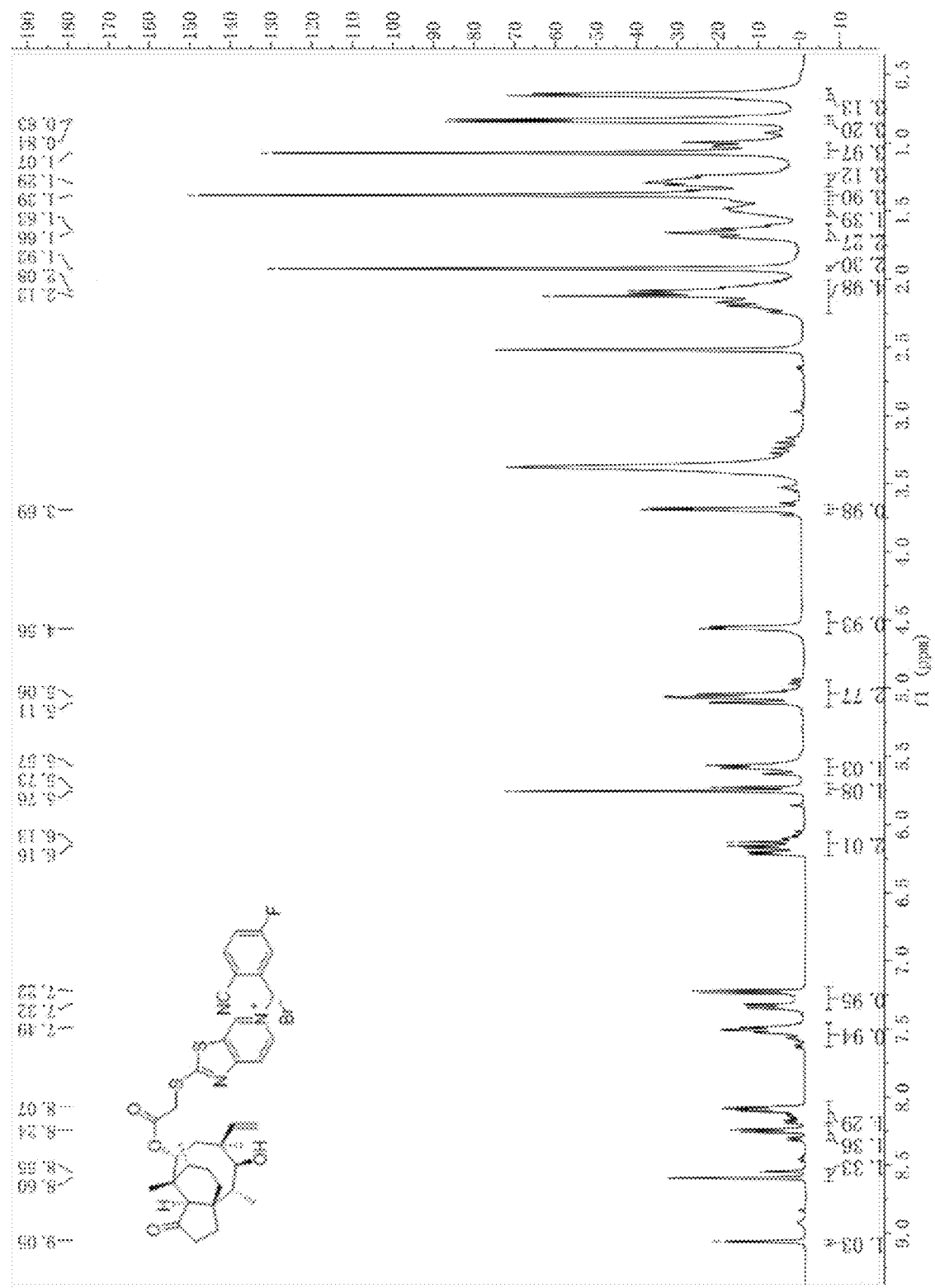
FIG. 25 is a $^1$H NMR spectrum of Compound I-13 of the present invention in deuterated DMSO.
Figure 26:
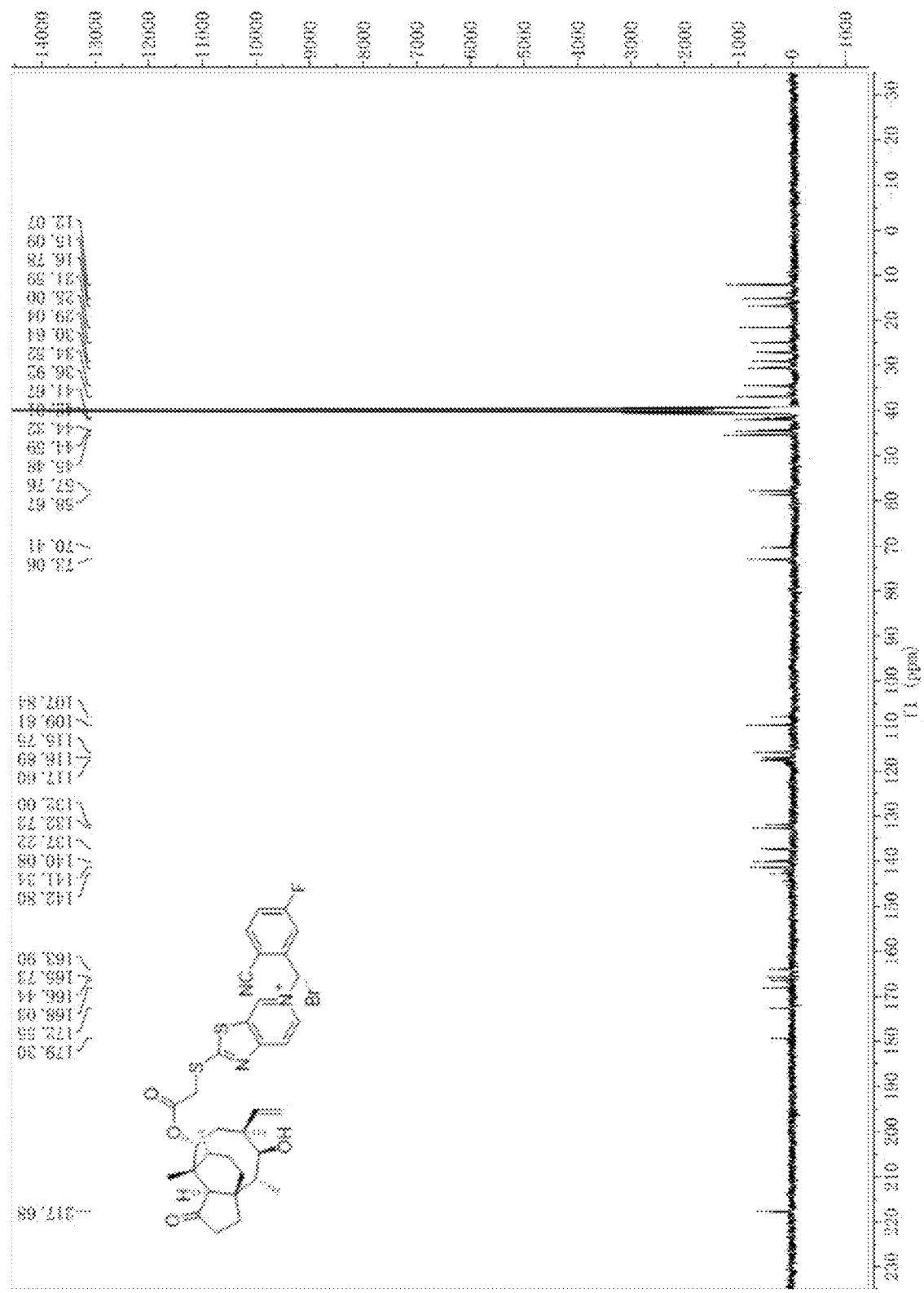
FIG. 26 is a $^{13}$C NMR spectrum of Compound I-13 of the present invention in deuterated DMSO.

The preparation method was as described in Example 1, except that the corresponding raw materials were replaced. Yield of Compound I-13 obtained: 85%. The $^1$H NMR spectrum of compound I-13 in deuterated DMSO is shown in FIG. 25, and the $^{13}$C NMR spectrum in deuterated DMSO is shown in FIG. 26.

$^1$H NMR (600 MHZ, DMSO-d6) δ 9.06 (d, J=7.0 Hz, 1H), 8.57 (dd, J=19.2, 1.8 Hz, 1H), 8.34-8.11 (m, 1H), 7.61-7.46 (m, 1H), 7.33 (dd, J=9.3, 2.7 Hz, 1H), 7.23 (d, J=7.0 Hz, 1H), 6.24-6.06 (m, 2H), 5.74 (d, J=10.4 Hz, 1H), 5.59 (p, J=9.1 Hz, 1H), 5.13-4.99 (m, 3H), 4.56 (d, J=5.9 Hz, 1H), 3.75-3.61 (m, 1H), 2.18-1.97 (m, 5H), 1.82 (s, 2H), 1.65 (q, J=11.7 Hz, 2H), 1.47 (m, 1H), 1.38-1.32 (d, J=4.7 Hz, 4H), 1.29-1.19 (d, J=4.7 Hz, 3H), 1.07 (s, 4H), 0.83 (d, J=7.0 Hz, 3H), 0.66 (td, J=8.0, 4.5 Hz, 3H).

$^{13}$C NMR (151 MHz, DMSO-d6) δ 217.68, 179.30, 172.55, 168.03, 166.44, 165.73, 163.90, 142.80, 141.34, 140.08, 137.22, 132.72, 132.00, 117.60, 116.89, 115.75, 109.81, 107.84, 73.06, 70.41, 58.67, 57.76, 45.48, 44.59, 44.32, 42.01, 41.67, 36.92, 34.52, 30.64, 29.04, 25.00, 21.59, 16.78, 15.09, 12.07.

Example 14

Preparation of Compound I-14:5-(3,5-dimethoxybenzyl)-2-((2-(((3aR,4R,5R,7S,8S,9R,9aS,12R)-8-hydroxy-4,7,9,12-tetramethyl-3-oxo-7-vinyldecahydro-4,9a-propancyclopenta[8] cyclo-5-yl)oxy)-2-oxoethyl)thio)thiazolo[5,4-c]pyridin-5-ium

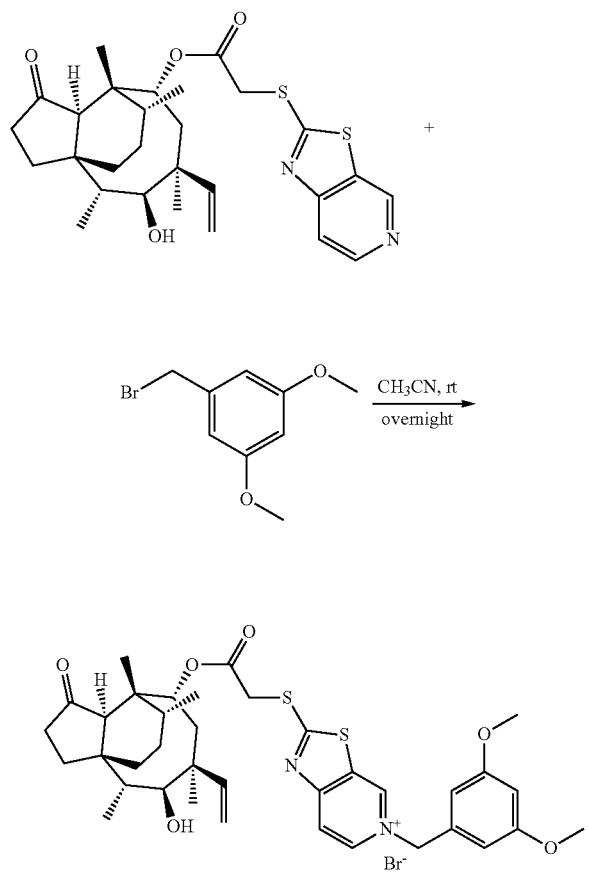

Figure 27:
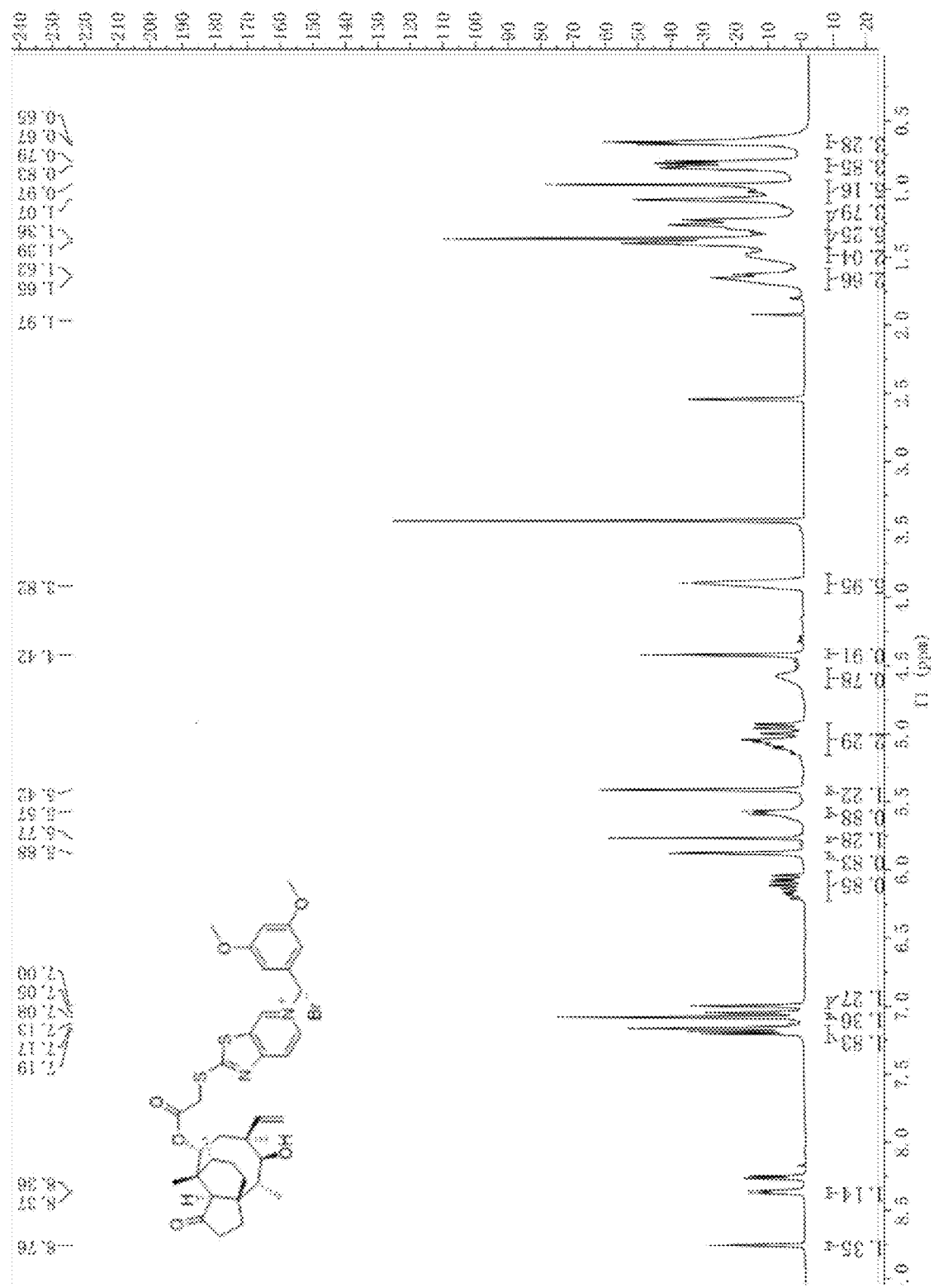
FIG. 27 is a $^1$H NMR spectrum of Compound I-14 of the present invention in deuterated DMSO.
Figure 28:
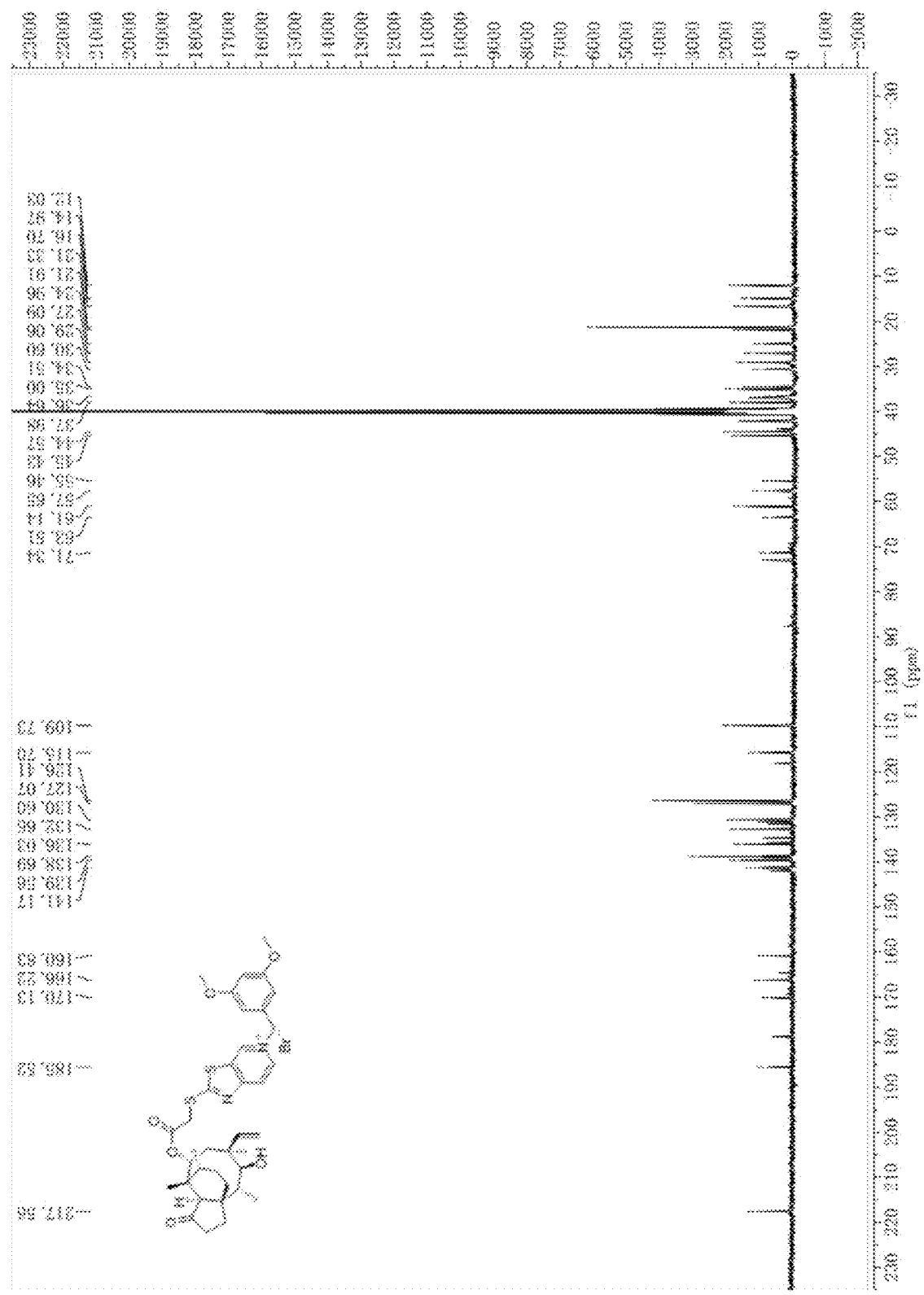
FIG. 28 is a $^{13}$C NMR spectrum of Compound I-14 of the present invention in deuterated DMSO.

The preparation method was as described in Example 1, except that the corresponding raw materials were replaced. Yield of Compound I-14 obtained: 92%. The $^1$H NMR spectrum of compound I-14 in deuterated DMSO is shown in FIG. 27, and the $^{13}$C NMR spectrum in deuterated DMSO is shown in FIG. 28.

$^1$H NMR (600 MHZ, DMSO-d6) δ 8.75 (d, J=2.6 Hz, 1H), 8.36 (d, J=6.8 Hz, 1H), 7.25-7.18 (d, J=9.6 Hz, 2H), 7.12 (s, 1H), 7.08 (s, 1H), 6.18-6.02 (m, 1H) 5.88 (s, 1H), 5.77 (s, 1H), 5.59 (t, J=6.6 Hz, 1H), 5.46 (s, 1H), 5.21-4.96 (d, J=2.3 Hz, 2H), 4.63 (s, 1H) 4.42 (s, 1H), 3.82 (s, 3H), 0.97 (m, 5H), 0.86-0.78 (m, 4H), 0.66 (t, J=5.9 Hz, 3H).

$^{13}$C NMR (151 MHZ, DMSO-d6) δ 217.56, 185.52, 170.13, 166.22, 160.83, 141.17, 139.56, 138.69, 136.03, 132.66, 130.60, 127.07, 126.41, 115.70, 109.73, 71.34, 63.51, 61.14, 57.65, 55.46, 45.43, 44.57, 37.98, 36.64, 35.00, 34.51, 30.60, 29.06, 27.09, 24.96, 21.91, 21.33, 16.70, 14.97, 12.03.

Example 15

In Vitro Antibacterial Activity Assay of Compounds

The minimum inhibitory concentrations (MIC) of pleuromutilin derivatives and their raw material pleuromutilin were tested by the broth microdilution method with tiamulin, valnemulin and retapamulin as positive control drugs.

The experimental strains included drug-resistant Gram-positive bacteria: Methicillin-resistant *S. aureus* ATCC 33591; Methicillin-resistant *S. aureus* ATCC 43300; *S. aureus* ATCC 29213; Methicillin-resistant *S. epidermidis* ATCC 51625. Drug-resistant Gram-negative bacteria: *A. baumannii* ATCC 19606; *S. enterica* ATCC14028; *E. coli* ATCC 25922; *E. coli* CMCC 44103. 9 clinically isolated resistant strains: MRSA-171; MRSA-575; MRSA-206; MRSA-222; MRSA-596; VRE-80; MDR-PA-126; MDR-KP-893; CR-AB-882.

The experimental strains were provided by Huashan Hospital Affiliated to Fudan University (Institute of Antibiotics, Fudan University) and used after identification by conventional methods.

The Specific Steps are as Follows:

(1) Preparation of MHB medium: Weigh 18.0 g of MHB medium, and add it to 1 L of distilled water. Heat to boiling until completely dissolved, divide it into conical bottles, sterilize it by high pressure at 121° C. for 15 minutes, and set aside.

(2) Cultivate the experimental strain to the logarithmic growth phase: Under sterile conditions, inoculate the experimental strain into fresh MHB medium and incubate at 37° C. in a constant temperature and humidity incubator for 24 hours. Adjust the bacterial solution concentration to $1.5 \times 10^8$ CFU/mL and then dilute it 200 times for later use.

(3) Preparation of storage solution: Weigh the sample to be tested, and dissolve it in 1% DMSO solution to prepare a storage solution with a concentration of 2560 μg/mL. Weigh the positive control, and dissolve it in sterile distilled water to prepare a storage solution with a concentration of 2560 μg/mL.

(4) Preparation of bacterial suspension: Under sterile conditions, the experimental strain cultured to the logarithmic growth phase was calibrated to a 0.5 McFarland unit turbidity standard using MHB medium and then diluted at a ratio of 1:200 to prepare a bacterial suspension with a concentration of $5 \times 10^5$ CFU/mL for later use.

(5) Determination of MIC by two-fold microdilution method: Take a sterile 96-well plate, add 10 μL of the test compound at a concentration of 2560 μg/mL, and perform serial dilutions by the two-fold dilution method. A negative control group without the drug is set simultaneously. Then, add 190 μL of diluted bacterial solution to each well, so that the final bacterial solution concentration in each well is $5 \times 10^5$ CFU/mL. Incubate in a 37° C. constant temperature and humidity chamber for 24 hours.

Figure 30:
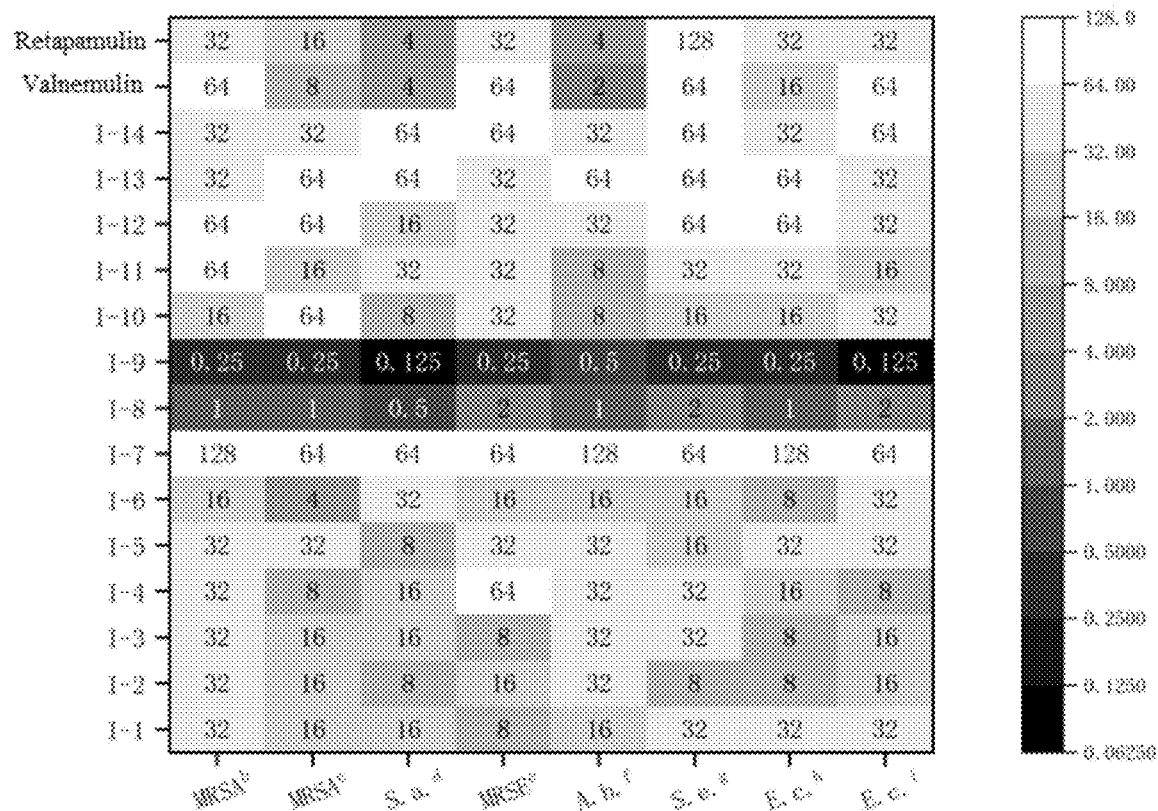
FIG. 30 is a heat map showing the correlation between the minimum inhibitory concentrations of the compounds of the present invention and the positive control drugs.

(6) MIC endpoint interpretation: Under a black background, visually observe the 96-well plate and identify the concentration that completely inhibits bacterial growth as the MIC of the sample against the bacteria. The recorded results are shown in TABLE 1 and FIG. 30.

TABLE 1

Minimum inhibitory concentration of the drug of the
present invention and the positive control drugs (μg · mL$^{-1}$)

| Compound | Gram-positive bacteria | | | | Gram-negative bacteria | | | |
|---|---|---|---|---|---|---|---|---|
| | MRSA$^b$ | MRSA$^c$ | S.a.$^d$ | MRSE$^e$ | A.b.$^f$ | S.e.$^g$ | E.c.$^h$ | E.c.$^i$ |
| I-1 | 32 | 16 | 16 | 8 | 16 | 32 | 32 | 32 |
| I-2 | 32 | 16 | 8 | 16 | 32 | 8 | 8 | 16 |
| I-3 | 32 | 16 | 16 | 8 | 32 | 32 | 8 | 16 |
| I-4 | 32 | 8 | 16 | 64 | 32 | 32 | 16 | 8 |
| I-5 | 32 | 32 | 8 | 32 | 32 | 16 | 32 | 32 |
| I-6 | 16 | 4 | 32 | 16 | 16 | 16 | 8 | 32 |
| I-7 | 128 | 64 | 64 | 64 | 128 | 64 | 128 | 64 |
| I-8 | 1 | 1 | 0.5 | 2 | 1 | 2 | 1 | 2 |
| I-9 | 0.25 | 0.25 | 0.125 | 0.25 | 0.5 | 0.25 | 0.25 | 0.125 |
| I-10 | 16 | 64 | 8 | 32 | 8 | 16 | 16 | 32 |
| I-11 | 64 | 16 | 32 | 32 | 8 | 32 | 32 | 16 |
| I-12 | 64 | 64 | 16 | 32 | 32 | 64 | 64 | 32 |
| I-13 | 32 | 64 | 64 | 32 | 64 | 64 | 64 | 32 |
| I-14 | 32 | 32 | 64 | 64 | 32 | 64 | 32 | 64 |
| Valnemulin | 64 | 8 | 4 | 64 | 2 | 64 | 16 | 64 |
| Retapamulin | 32 | 16 | 4 | 32 | 4 | 128 | 32 | 32 |

MRSA$^b$: $^b$Methicillin-resistant *S. aureus* ATCC 33591;
MRSA$^c$: $^c$Methicillin-resistant *S. aureus* ATCC 43300;
S.a.$^d$: $^d$*S. aureus* ATCC 29213;
MRSE$^e$: $^e$Methicillin-resistant *S. epidermidis* ATCC 51625;
A.b.$^f$: $^f$*A. baumannii* ATCC 19606;
S.e.$^g$: $^g$*S. enterica* ATCC14028;
E.c.$^h$: $^h$*E. coli* ATCC 25922;
E.c.$^i$: $^i$*E. coli* CMCC 44103.

TABLE 2

Antibacterial activity of compounds I-8 and
I-9 against 9 clinically isolated strains (μg · mL$^{-1}$)

| Compound | Clinical isolates | | | | | | | | |
|---|---|---|---|---|---|---|---|---|---|
| | MRSA$^b$ | MRSA$^c$ | MRSA$^d$ | MRSE$^e$ | MRSA$^f$ | VRE$^g$ | MDR-PA$^h$ | MDR-KP$^i$ | CR-AB$^j$ |
| I-8 | 16 | 32 | 64 | 16 | 8 | 16 | 32 | 16 | 64 |
| I-9 | 8 | 4 | 2 | 4 | 8 | 8 | 8 | 2 | 4 |
| Retapamulin | 128 | 32 | 64 | 128 | 32 | >128 | 64 | 128 | 64 |

MRSA$^b$: methicillin-resistant *Staphylococcus aureus*-171;
MRSA$^c$: methicillin-resistant *Staphylococcus aureus*-575;
MRSA$^d$: methicillin-resistant *Staphylococcus aureus*-206;
MRSA$^e$: methicillin-resistant *Staphylococcus aureus*-222;
MRSA$^f$: methicillin-resistant *Staphylococcus aureus*-596;
VRE$^g$: vancomycin-resistant *Enterococcus*-80;
MDR-PA$^h$: multidrug-resistant *Pseudomonas aeruginosa*-126;
MDR-KP$^i$: multidrug-resistant *Klebsiella pneumoniae*-893;
CR-AB$^j$: carbapenem-resistant *Acinetobacter baumannii*-882.

As shown in TABLE 1, the minimum values of 14 target compounds (I-1~I-14), along with retapamulin and valnemulin, the results show that under the conditions of quaternization with benzyl bromide, the pleuromutilin derivatives containing thiazolo[5,4-C]pyridine side chains exhibit excellent activity. Compounds such as I-2, I-3, I-4, I-6, and I-10 show similar potency and nearly equivalent antibacterial activity compared to valnemulin and retapamulin. Notably, in comparison to the antibacterial activity of valnemulin and retapamulin, I-8 demonstrates good antibacterial activity, while I-9 exhibits the most advantageous antibacterial activity. Both I-8 and I-9 show significant efficacy against both Gram-positive and Gram-negative bacteria. Derivatives I-1 to I-11 were synthesized by introducing various electron-withdrawing and electron-donating groups at the para position on the benzene ring. The results showed that the para-substituted groups (I-1~I-11) not only enhance the antibacterial efficacy against Gram-positive bacteria, but also significantly improve the antibacterial activity against Gram-negative bacteria such as *E. coli* and *A. baumannii*, with activity superior to the positive control drugs. Notably, para-substituted methyl compound I-9 became the most active compound in the series, showing significant antibacterial activity with MIC values ranging from 0.125 to 0.5 μg/mL. Similarly, the derivative I-8, containing a cyano substituent, displays excellent activity with MIC values ranging from 0.5 to 2 μg/mL.

Figure 31:
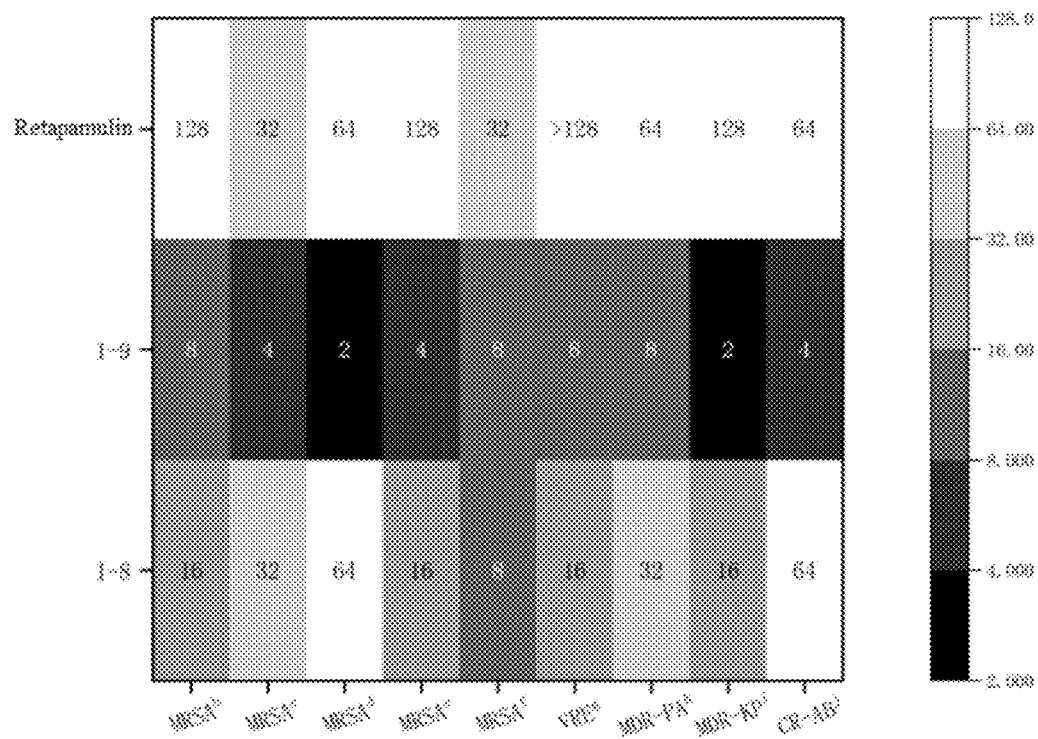
FIG. 31 shows the antibacterial activity of the compounds of the present invention against clinically isolated strains.

In addition, the active compounds I-8 and I-9 were further tested against 9 clinical isolated strains, including MRSA, vancomycin-resistant enterococci (VRE), and multidrug-resistant *Pseudomonas aeruginosa* (MDRPA). The results are shown in TABLE 2 and FIG. 31. Notably, compound I-9 exhibited effective anti-VRE and anti-CR-AB activities, with MIC values of compound I-9 against VRE and CR-AB being 8 and 4 μg/mL, respectively.

Compound I-9 showed superior activity against clinically common Gram-negative pathogens, including MDR PA, MDR KP, and CR AB, compared to retapamulin. Specifically, I-9 showed excellent antibacterial activity against five clinical MRSA isolates, including MRSA-171, MRSA-575, MRSA-206, MRSA-222, and MRSA-596 (MIC of 2-8 µg/mL), especially against MRSA-206 strain, with MIC values ranging from 2 to 8 µg/mL, particularly demonstrating outstanding activity against the MRSA-206 strain, with an MIC of 2 µg/mL.

Example 16

Molecular Docking Study of Compounds I-8 and I-9 with Target Proteins (1) Data preparation: First, the three-dimensional structure of the macromolecular receptor (PDB ID: 5HL7) was collected and prepared, which was downloaded from the RCSB database based on the crystal structure of S. aureus in complex with lefamulin. Additionally, the structural data of the small molecule drugs (ligands) were obtained.

(2) Protein preparation: The structure of the target protein is processed, which includes removing water molecules, ions and other non-protein parts.

(3) Ligand preparation: The selected small-molecule drug compounds were optimized and prepared, involving geometric optimization and charge distribution.

(4) Grid generation: A three-dimensional grid was generated the active site of the protein to accelerate the calculation of the docking algorithm. This step is crucial to computational efficiency, and the grid required for efficient docking calculations is generated by professional software.

(5) Docking calculation: AutoDock molecular docking software was used to perform calculations to predict the binding mode between ligand and protein.

(6) Binding mode analysis: After obtaining the docking results, an analysis of the binding modes is conducted to identify the most stable interactions. The binding mode with the lowest energy is selected based on the energy scoring.

Figure 29:
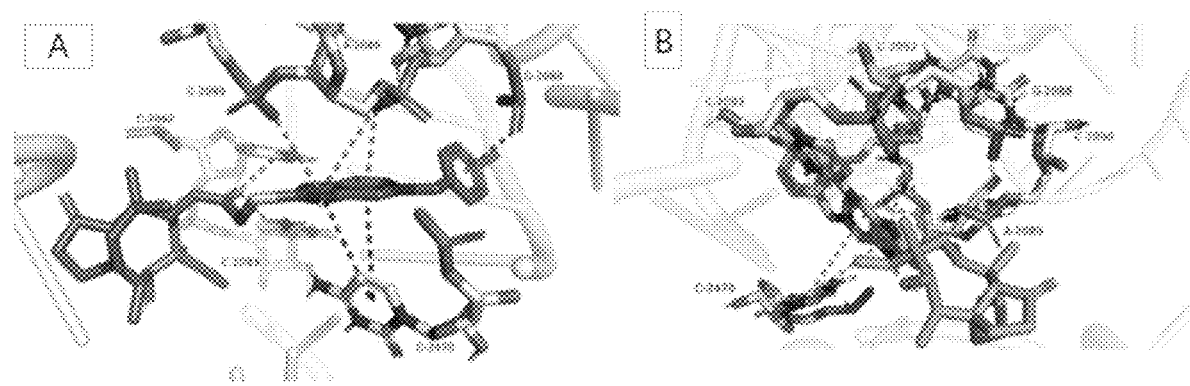
FIG. 29 is the docking diagram of Compounds I-8, I-9 and 5HL7; A shows a docking diagram of Compound I-8 with 5HL7, and B shows a docking diagram of Compound I-9 with 5HL7.

(7) Evaluate the results: The docking results were statistically analyzed to assess binding affinity and predict the ligands with the highest affinity. This step was combined with experimental data and other computational results to ensure the reliability of the outcomes. Molecular visualization tools, such as PyMOL and Chimera, were used to visualize the final docking results, as shown in FIG. 29.

The results showed that the compound molecule bound tightly to the cavity containing residues near the center of peptidyl transferase, and the binding energy was low, providing a basis for the antibacterial ability of the compound.

Example 17

Solubility Experiment

The solubility of compounds I-1~I-14, tiamulin and valnemulin was determined.

(1) Preparation: Several samples of the compounds to be tested were prepared as a series of solutions ranging from unsaturated to saturated. The solutions were placed under constant temperature conditions and shaken until equilibrium was reached. After filtration through a membrane filter, the filtrate was analyzed.

(2) Measurement: The actual concentration(S) of the drug in the solution was measured, and a plot was made of the concentration (c) of the prepared solution. The inflection point of the curve was taken as the equilibrium solubility of the drug. The solubility of compounds I-1 to I-14, tiamulin, and valnemulin is shown in TABLE 3 and FIG. 32.

TABLE 3

Solubility of compounds I-1~I-14, tiamulin, and valnemulin

| Compound | Solubility (nM) |
| --- | --- |
| I-1 | 0.45 |
| I-2 | 0.327 |
| I-3 | 0.561 |
| I-4 | 0.247 |
| I-5 | 0.623 |
| I-6 | 0.887 |
| I-7 | 0.656 |
| I-8 | 0.634 |
| I-9 | 0.812 |
| I-10 | 0.513 |
| I-11 | 0.611 |
| I-12 | 0.549 |
| I-13 | 0.231 |
| I-14 | 0.126 |
| Tiamulin | 0.259 |
| Valnemulin | 0.386 |

Figure 32:
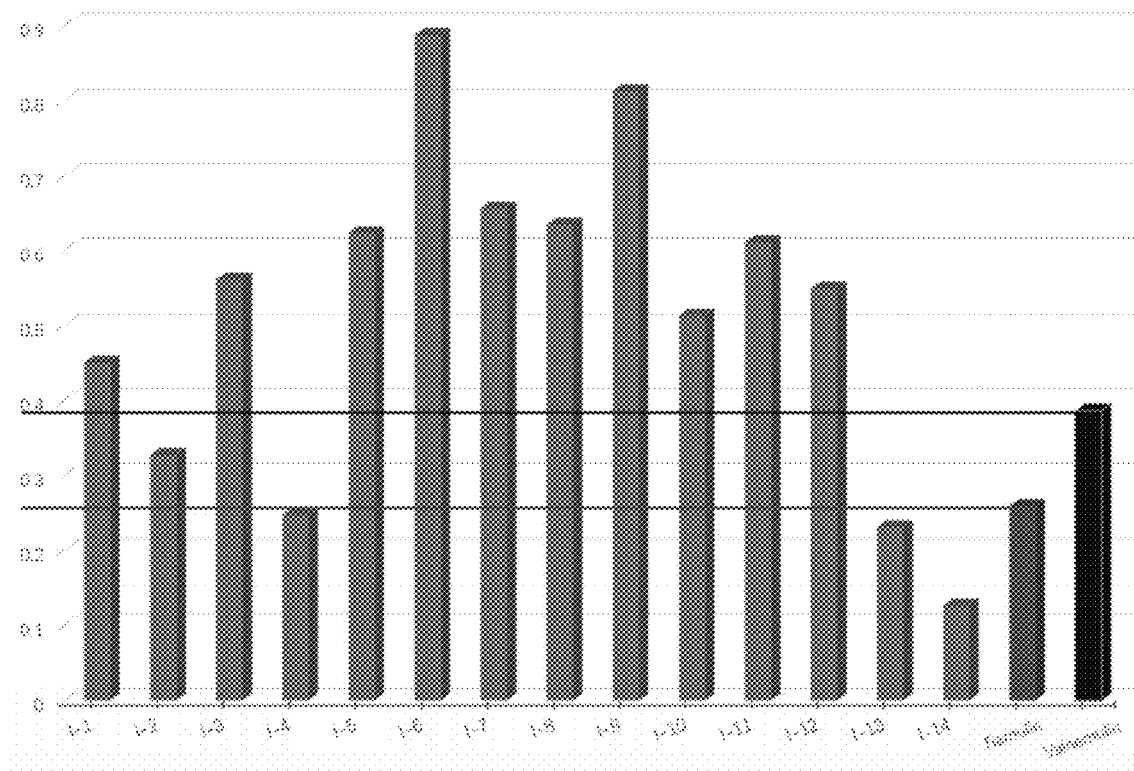
FIG. 32 shows the solubility of Compound I-14, tiamulin and valnemulin.

As shown in TABLE 3 and FIG. 32, the solubility of the modified pleuromutilin compounds is significantly improved compared with the control drug.

Example 18

Safety Evaluation of Compounds
Cell Counting Kit-8 was Used to Evaluate the Cytotoxicity of the Compounds.

(1) Preparation: 10 mM PBS buffer: Dissolve 8.00 g NaCl, 0.20 g KCl, 1.44 g $Na_2HPO_4$, and 0.24 g $KH_2PO_4$ in 800 mL distilled water and adjust the pH to 7.4. Then, dilute the solution to a total volume of 1 L with distilled water and sterilize for 40 minutes. Set aside for use.

(2) Preparation of bottom agar medium: Dissolve 6.00 g of agar powder in 400 mL of distilled water. Stir well and then autoclave for 40 minutes to ensure the sterility of the medium. Then, when the solution cools to 60-70° C., add 8 mL of VS solution and 8 mL of GS solution. After adding each solution, mix thoroughly to ensure uniform distribution. Finally, pour the mixed agar solution into a plate to prepare the bottom agar medium.

(3) Preparation of top agar medium: First, dissolve 1.20 g agar powder and 1.00 g NaCl in 200 mL of distilled water. After mixing, autoclave for 40 minutes to ensure the sterility of the medium. Next, when the solution cools to 60° C., add 1.00 mL of HBT solution and mix thoroughly. Finally, aliquot 2 mL of the mixture into sterile test tubes. Keep the medium warm before use, typically by maintaining it in a water bath at 45° C.

(4) Cell culture: HepG2, HEK293 and A549 cells were evenly dispersed in culture medium, seeded into 96-well plates, and cultured under appropriate environmental conditions to ensure complete attachment of the cells to the well walls.

(5) Compound treatment: Add different concentrations of compounds I-8 and I-9 to each well (concentrations of 0.78, 1.56, 3.13, 6.25, 12.5, 25, 50, and 100 µM, with six parallel experiments). Set up blank control group and normal control group. After incubation for 24 hours, observe the cell condition, which may be observed under a microscope.

(6) CCK-8 solution treatment: Add CCK-8 solution to each well and incubate for 4 hours to allow it to react with the cells.

(7) Absorbance determination: Use a full-wavelength scanning multifunctional reader to measure absorbance at 490 nm. Place the 96-well plate into the instrument and oscillate to mix the color evenly before reading the absorbance value.

(8) Data analysis: Based on the measured absorbance values, the cell survival rate at different concentrations can be calculated. The median cytotoxic concentration ($CC_{50}$) was used to evaluate the cytotoxicity of the compound to A549, HEK293 and HepG2 cells. The experimental results are shown in TABLE 4.

TABLE 4

Cytotoxicity test results of compounds I-8, I-9, retapamulin and valnemulin

| Compound | $CC_{50}$ (μM) | | |
|---|---|---|---|
| | HepG2 Cells | HEK293 Cells | A549 Cells |
| I-8 | 78.50 | 79.18 | >100 |
| I-9 | 66.41 | 82.14 | >100 |
| Retapamulin | 61.14 | 57.47 | 71.53 |
| Valnemulin | 77.26 | 65.38 | 53.74 |

As shown in TABLE 4, in the safety evaluation experiment, at a concentration of 100 μM, compounds I-8 and I-9 showed low toxicity to the tested cells. The tested cells included: HepG2 cells, HEK293 cells and A549 cells. Compared with the control drugs retapamulin and valnemulin, compounds I-8 and I-9 demonstrated lower toxicity to the tested cells.

The invention claimed is:

1. A compound of formula I, a pharmaceutically acceptable salt, or a tautomer thereof:

Formula I

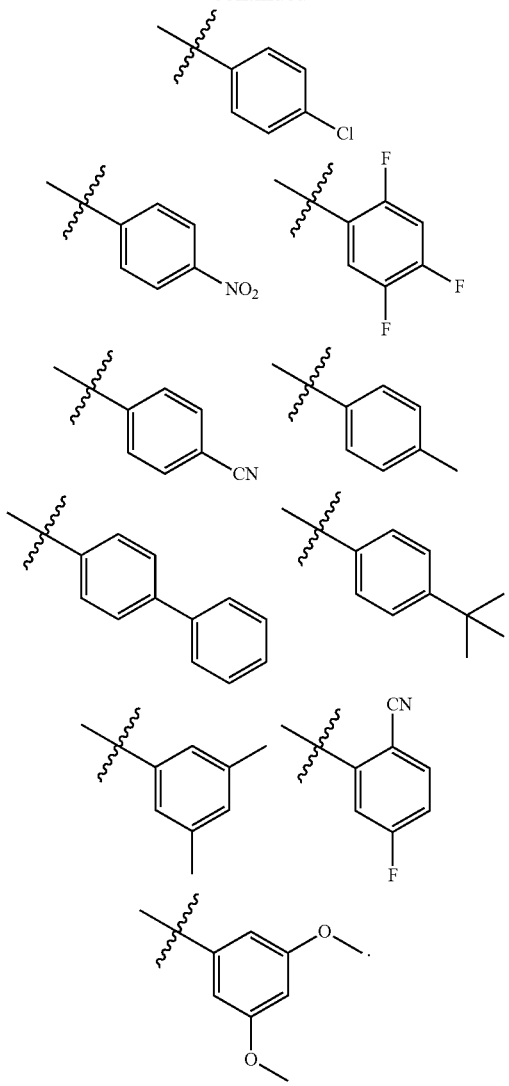

wherein R is a phenyl group substituted with an electron withdrawing group or a phenyl group substituted with an electron donating group.

2. The compound according to claim 1, wherein the R is one of the following phenyl groups:

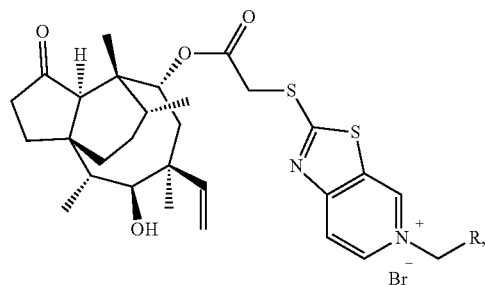

3. The compound according to claim 2, wherein the R is one of the following phenyl groups:

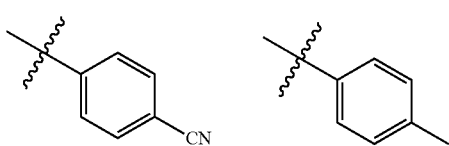

4. The compound according to claim 3, wherein the R is:

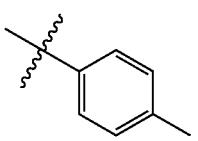

5. The compound according to claim 1, wherein the compound is selected from the group consisting of:

-continued
I-1
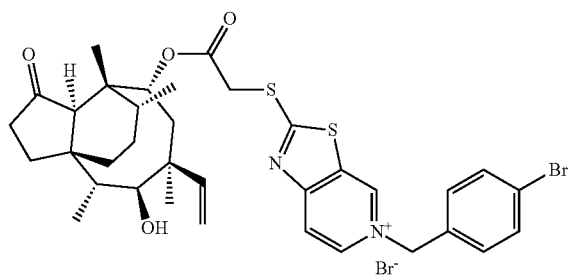
I-6
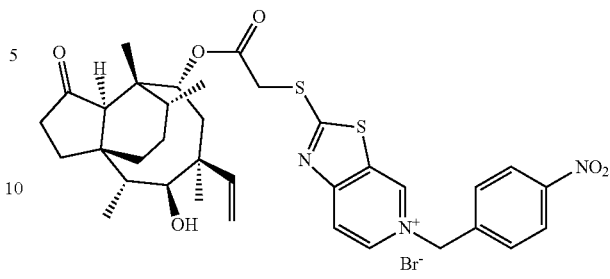
I-2
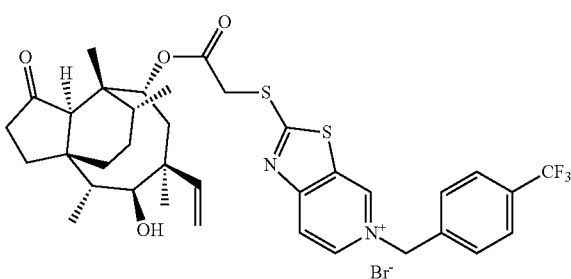
I-7
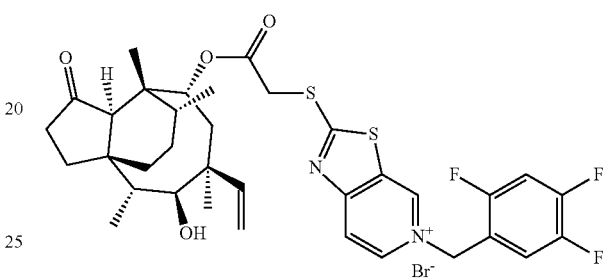
I-3
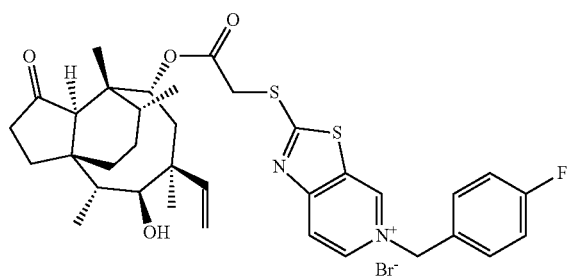
I-8
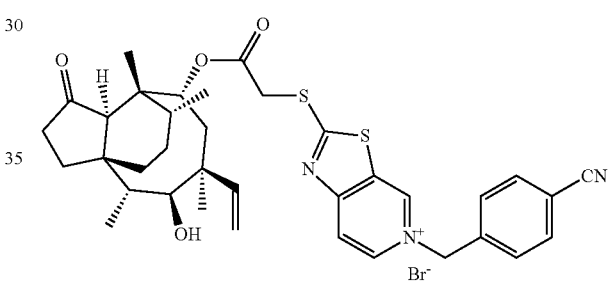
I-4
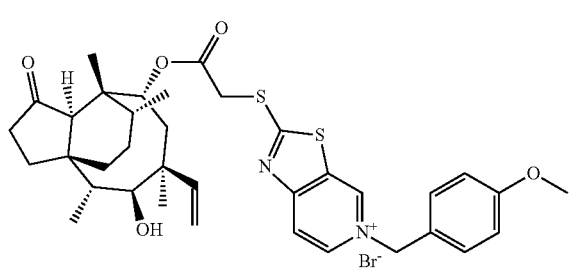
I-9
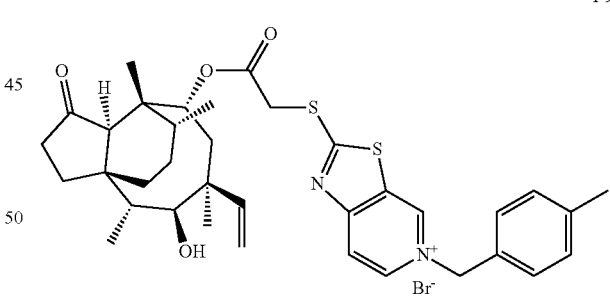
I-5
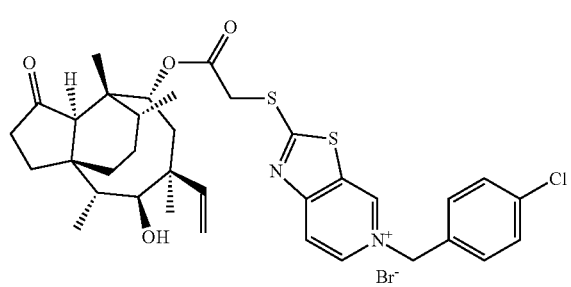
I-10
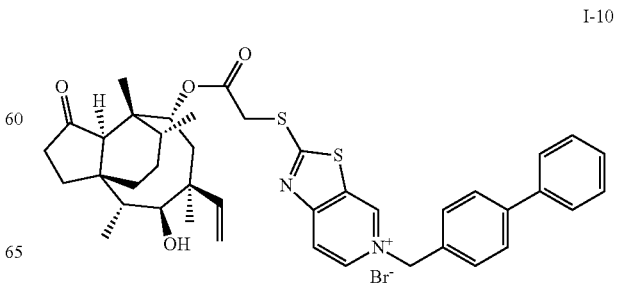

-continued

I-11

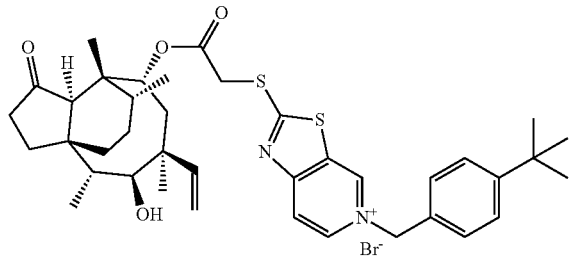

I-12

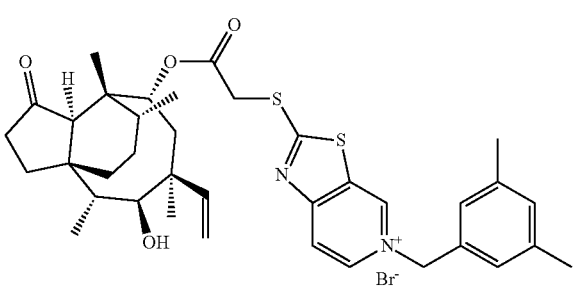

I-13

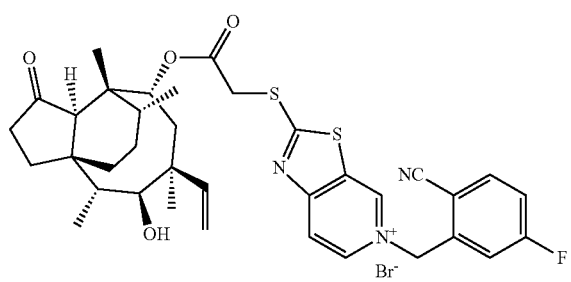

I-14

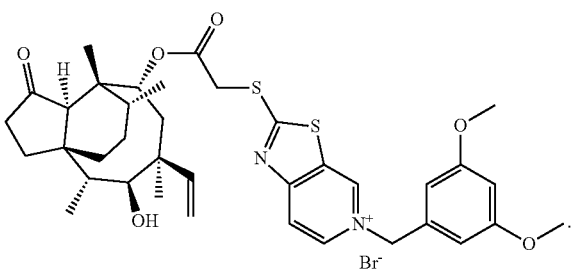

6. The compound according to claim 1, wherein the pharmaceutically acceptable salt comprises one selected from the group consisting of hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid, and aspartic acid.

7. A method for preparing the compound according to claim 1, comprising the following steps:

(1) reacting pleuromutilin with tosyl chloride to obtain an intermediate I, wherein the intermediate I is

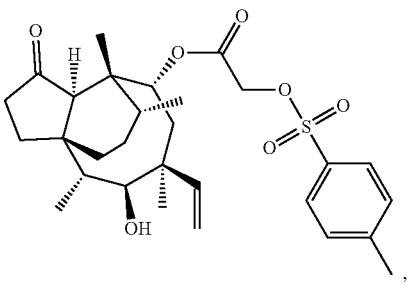 [SMILES: C=C[C@]1(C)C[C@@H](OC(=O)COS(=O)(=O)c2ccc(C)cc2)[C@]2(C)[C@H](C)CC[C@]3(CCC(=O)[C@H]32)[C@@H](C)[C@@H]1O]

(2) reacting 4-amino-3-fluoropyridine with potassium ethyl xanthate to obtain an intermediate II, wherein the intermediate II is

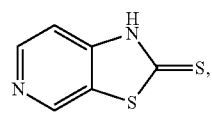

(3) reacting the intermediate I with an intermediate II to obtain the intermediate III, wherein the intermediate III is

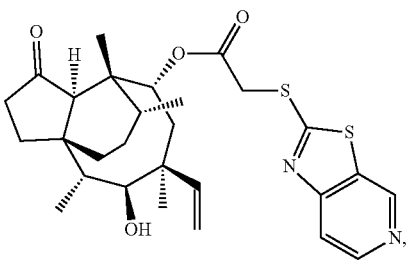 [SMILES: C=C[C@]1(C)C[C@@H](OC(=O)CSc2nc3ccncc3s2)[C@]2(C)[C@H](C)CC[C@]3(CCC(=O)[C@H]32)[C@@H](C)[C@@H]1O]

(4) reacting the intermediate III with a substituted benzene ring compound to obtain the compound of formula I, wherein the formula I is Formula I

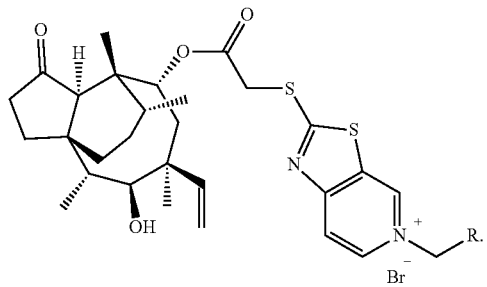

8. The method according to claim 6, wherein the b substituted benzene ring compound is p-bromobenzyl bromide, 4-(trifluoromethyl)benzyl bromide, p-fluorobenzyl bromide, 4-methoxybenzyl bromide, 4-chlorobenzyl bromide, p-nitrobenzyl bromide, 1-bromo-2,4,5-trifluorobenzene, 4-cyanobenzyl bromide, p-methylbenzyl bromide, 4-bromomethylbiphenyl, 4-tert-butylbenzyl bromide, 3,5-dimethylbenzyl bromide, 2-cyano-5-fluorobenzyl bromide or 3,5-dimethoxybenzyl bromide.

9. An application of the compound according to claim 1 in preparing drugs for the treatment of an infectious disease caused by a pathogenic microorganism.

10. The application according to claim 8, wherein the pathogenic microorganism is Gram-positive bacteria, Gram-negative bacteria, drug-resistant bacteria, or *mycoplasma*.

11. A pharmaceutical composition comprising the compound of claim 1 and a pharmaceutically acceptable excipient.

* * * * *